US007498353B2

(12) United States Patent
Singh et al.

(10) Patent No.: US 7,498,353 B2
(45) Date of Patent: Mar. 3, 2009

(54) HETEROCYCLIC ANTI-VIRAL COMPOUNDS COMPRISING METABOLIZABLE MOIETIES AND THEIR USES

(75) Inventors: Rajinder Singh, Belmont, CA (US); Dane Goff, Redwood City, CA (US); Ihab S. Darwish, San Mateo, CA (US); Rao S. S. Kolluri, Foster City, CA (US); Henry Lu, Foster City, CA (US); Gary Park, Moss Beach, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 11/381,215

(22) Filed: May 2, 2006

(65) Prior Publication Data

US 2006/0247287 A1 Nov. 2, 2006

Related U.S. Application Data

(60) Provisional application No. 60/677,374, filed on May 2, 2005.

(51) Int. Cl.
A01N 43/80 (2006.01)
A61K 31/42 (2006.01)

(52) U.S. Cl. .................... 514/378; 514/236.8; 514/332; 514/333; 514/340; 548/100; 548/112; 548/247; 548/240; 546/208; 546/255; 546/256; 546/268.1; 546/269.7; 544/137

(58) Field of Classification Search ................. 514/378, 514/236.8, 332, 333, 340; 548/112, 247, 548/100, 240; 546/208, 255, 256, 268.1, 546/269.7; 544/137
See application file for complete search history.

(56) References Cited

U.S. PATENT DOCUMENTS

| 2,852,503 | A |   | 9/1958 | Edward et al. |
| 3,189,447 | A |   | 6/1965 | Neugebauer et al. |
| 3,257,203 | A |   | 6/1966 | Klupfel et al. |
| 3,335,149 | A |   | 8/1967 | Preston |
| 3,910,942 | A |   | 10/1975 | Narayanan et al. |
| 3,964,896 | A |   | 6/1976 | Neidermyer et al. |
| 4,087,409 | A |   | 5/1978 | Preston |
| 4,405,793 | A |   | 9/1983 | Fuchs et al. |
| 4,743,521 | A |   | 5/1988 | Hoffmann et al. |
| 4,752,324 | A |   | 6/1988 | Thomas et al. |
| 4,777,258 | A |   | 10/1988 | Sitzmann |
| 5,151,441 | A |   | 9/1992 | Mueller et al. |
| 5,256,666 | A |   | 10/1993 | Mueller et al. |
| 5,463,071 | A |   | 10/1995 | Himmelsbach et al. |
| 5,814,627 | A |   | 9/1998 | Schwab et al. |
| 5,962,685 | A | * | 10/1999 | Ueda et al. .................. 544/300 |
| 6,277,830 | B1 |  | 8/2001 | Ganguly et al. |
| 6,355,669 | B1 |  | 3/2002 | Yamauchi et al. |
| 6,403,564 | B1 |  | 6/2002 | Ganguly et al. |
| 6,579,880 | B2 |  | 6/2003 | Weidner-Wells et al. |
| 6,759,538 | B2 |  | 7/2004 | Singh et al. |
| 7,115,642 | B2 | * | 10/2006 | Singh et al. .................. 514/378 |
| 7,153,880 | B2 | * | 12/2006 | Singh et al. .................. 514/378 |
| 7,157,473 | B2 | * | 1/2007 | Singh et al. .................. 514/332 |
| 7,220,745 | B2 | * | 5/2007 | Singh et al. .............. 514/236.2 |
| 7,326,790 | B2 | * | 2/2008 | Singh et al. .................. 548/240 |
| 7,332,602 | B2 | * | 2/2008 | Singh et al. .................. 544/124 |
| 2002/0035156 | A1 |  | 3/2002 | Roniker et al. |
| 2005/0239751 | A1 |  | 10/2005 | Singh et al. |

FOREIGN PATENT DOCUMENTS

| CH | 392 520 | 10/1965 |
| CH | 559 195 | 2/1975 |
| DE | 21 37 719 | 2/1973 |
| DE | 27 21 955 | 11/1978 |
| DE | 100 32 874 | 1/2002 |
| DE | 101 48 598 | 10/2002 |
| EP | 563686 | 3/1993 |
| EP | 0 776 894 | 6/1997 |
| EP | 0 927 922 | 7/1999 |
| EP | 1 180 518 | 2/2002 |
| EP | 1 348 706 | 10/2003 |
| FR | 1 459 375 | 4/1966 |
| JP | 3-122652 | 5/1991 |
| JP | 04124178 | 4/1992 |
| JP | 2-146048 | 8/2007 |

(Continued)

OTHER PUBLICATIONS

Zhou et al., {An Antibody-Catalyzed Allylic Sulfoxide-Sulfenate Rearrangement, Journal of Organic Chemistry (1999), 64(22), 8334-8341}.*
Gatta, et al., Synthesis of [1, 2, 4] Triazoloquinazoline and [1, 2, 4] Triazolo-1, 4-benzodiazepine derivatives. Journal of Heterocyclic Chemistry, 1993, vol. 30, pp. 11-16.
Maybridge Hts, Order No. BTB 09742; RN 247059-16 Maybridge PLC, Trevillett, Tintagel Cornwall, PL 340HW, UK, Jan. 8, 2004, XP002297442.
STN File CA, Abstract 135:46129 & V.M. Barot et al, Asian Journal of Chemistry, 2001, 13(1), pp. 341-343.
STN File CA, Abstract 132:265141 & S.V. Damle et al., Indian Journal of Heterocyclic Chemistry, 1999, 9(2), pp. 81-86.
STN File CA, Abstract 132:180505 & V.R. Naik et al., Asian Journal of Chemistry, 2000, 12(1), pp. 305-307.

(Continued)

Primary Examiner—Chukwuma O. Nwaonicha
(74) Attorney, Agent, or Firm—McDonnell Boehnen Hulbert & Berghoff LLP

(57) ABSTRACT

The present invention relates to prodrugs and compositions thereof useful for treating or preventing Hepatitis C virus (HCV) infections. In particular, the present invention relates to prodrugs of substituted diphenyl-, diheteroaryl- and mixed phenyl heteroaryl substituted five-membered heterocycle compounds, compositions comprising the compounds and the use of such compounds and compositions to inhibit HCV replication and/or proliferation as a therapeutic approach towards the treatment and/or prevention of HCV infections in humans and animals.

24 Claims, 4 Drawing Sheets

FOREIGN PATENT DOCUMENTS

| WO | 93-17671 | 9/1993 |
| WO | 94-17059 | 8/1994 |
| WO | 95-24397 | 9/1995 |
| WO | 98-17652 | 4/1998 |
| WO | 98-47509 | 10/1998 |
| WO | 99-04390 | 1/1999 |
| WO | 99-20309 | 4/1999 |
| WO | 00/23454 A1 | 4/2000 |
| WO | 00-40242 | 7/2000 |
| WO | 00-45799 | 8/2000 |
| WO | 00-78726 | 12/2000 |
| WO | 01-74811 | 10/2001 |
| WO | 01-78648 | 10/2001 |
| WO | 02-20436 | 3/2002 |
| WO | 02-46186 | 6/2002 |
| WO | 02-055025 | 7/2002 |
| WO | 03-029210 | 4/2003 |
| WO | 03-040112 | 5/2003 |
| WO | 03/040112 A1 | 5/2003 |
| WO | 2004-018463 | 3/2004 |
| WO | 2004/099164 A1 | 11/2004 |
| WO | 2004/099165 A2 | 11/2004 |
| WO | 2004-103366 | 12/2004 |
| WO | 2005/000308 A2 | 1/2005 |
| WO | 2005/097760 A1 | 10/2005 |

OTHER PUBLICATIONS

STN File CA, Abstract 129:216539 & S.M. Naik et al, Oriental Journal of Chemistry (1998), 14(1), pp. 167-168.

STN File CA, Abstract 126:74789 & M. Shah et al., Indian Journal of Chemistry, Section B: Organic Chemistry Including Medicinal Chemistry (1996), 35B(12), pp. 1282-1286.

STN File CA, Abstract 122:81186 & S.R. Modi et al, Oriental Journal of Chemistry, 1994, 10(1), pp. 85-86.

STN File CA, Abstract 118:191597 & T. Bandiera et al, Journal of Heterocyclic Chemistry (1992), 29(6), pp. 1423-1428.

Roth, et al., "Zur Kondensation von Chalkonoxyden mit Hydroxylamin," Arch. Pharm. vol. 94, pp. 769-774, 1961.

Samula, "Oksymowanic Azachalkonow," Roczniki Chemll, Ann. Soc. Chim. Polonorum, vol. 45, p. 2063, 1971.

Samula, "Cyclization of Azachalcones and B-Hydroxyketones Oximes," Roczniki ChemLL, Ann soc. Chim, Polonorum, vol. 48, pp. 959-964, 1974.

Howe, et al., "Nitrile Oxide Cycloaddition Routes to 2-(Isoxazoly)-benzoates and 2-(1, 2, 4-Oxadiazol-3-yl) benzoates," Heterocycl. Chem., vol. 19, No. 4, pp. 721-726, 1982.

Belgodere et al., "Studies on Isomeric Pyridylisoxazoles," Heterocycles, vol. 20, No. 3, pp. 501-504, 1983.

Batori et al., "Photoinduced Ring Transformation of Pyrido [1, 2-b] pyridazinium-r-olate," Tetrehedron, vol. 50, No. 16, pp. 4699-4708, 1994.

Kanbara et al., "Preparation of Soluble and Fluorescent Poly(arylene)s by 1,3-Dipolar Polycycloaddition and Properties of the Polymers," Polymer Bulletin, vol. 36, pp. 673-679, 1996.

Ku et al., "Use of Lodoacetylene as a Dipolarphile in the Synthesis of 5-Iodoisoxazole Derivatives," Organic Letters, vol. 3, No. 26, pp. 4185-4187, 2001.

Maybridge, plc, Trevillett, Tintagel, Catalogue No. RF01972, Cornwall PL34 OHW, England.

Maybridge, plc, Trevillett, Tintagel, Catalog No. RF01996, Cornwall PL34 OHW, England.

Hacks Chemical Dictionary, Fourth Edition, Julius Grant, 1972, p. 203.

* cited by examiner

HETEROCYCLIC ANTI-VIRAL COMPOUNDS COMPRISING METABOLIZABLE MOIETIES AND THEIR USES

BACKGROUND OF THE INVENTION

1. Field of Invention

The present invention relates to prodrug and compositions thereof useful for treating or preventing Hepatitis C virus (HCV) infections. In particular, the present invention relates to prodrugs of substituted diphenyl-, diheteroaryl- and mixed phenyl heteroaryl substituted five-membered heterocycle compounds, compositions comprising the compounds and the use of such compounds and compositions to inhibit HCV replication and/or proliferation as a therapeutic approach towards the treatment and/or prevention of HCV infections in humans and animals.

2. Summary of the Related Art

Hepatitis C virus (HCV) infection is a global human health problem with approximately 150,000 new reported cases each year in the United States alone. HCV is a single stranded RNA virus, which is the etiological agent identified in most cases of non-A, non-B post-transfusion and post-transplant hepatitis and is a common cause of acute sporadic hepatitis (Choo et al., *Science* 244:359, 1989; Kuo et al., *Science* 244:362, 1989; and Alter et al., in *Current Perspective in Hepatology*, p. 83, 1989).

It is estimated that more than 50% of patients infected with HCV become chronically infected and 20% of those develop cirrhosis of the liver within 20 years (Davis et al., *New Engl. J. Med.* 321:1501, 1989; Alter et al., in *Current Perspective in Hepatology*, p. 83, 1989; Alter et al., *New Engl. J. Med.* 327:1899, 1992; and Dienstag *Gastroenterology* 85:430, 1983). Moreover, the only therapy available for treatment of HCV infection is interferon-α (INTRON® A, PEG-INTRON® A, Schering-Plough; ROFERON-A®, PEGASys®, Roche). Most patients are unresponsive, however, and among the responders, there is a high recurrence rate within 6-12 months after cessation of treatment (Liang et al., *J. Med. Virol.* 40:69, 1993). Ribavirin, a guanosine analog with broad spectrum activity against many RNA and DNA viruses, has been shown in clinical trials to be effective against chronic HCV infection when used in combination with interferon-α (see, e.g., Poynard et al., *Lancet* 352:1426-1432, 1998; Reichard et al., *Lancet* 351:83-87, 1998), and this combination therapy has been recently approved (REBETRON, Schering-Plough; see also Fried et al., 2002, N. Engl. J. Med. 347:975-982). However, the response rate is still at or below 50%. Therefore, additional compounds for treatment and prevention of HCV infection are needed.

SUMMARY OF THE INVENTION

The invention provides compounds, compositions and methods comprising substituted heterocyclic prodrugs that are metabolized into potent inhibitors of Hepatitis C virus ("HCV") replication and/or proliferation.

In a first aspect, the invention provides compound of the structural formula $$A\text{-}B\text{-}C\text{-}N(R^{11})\text{-}C(O)\text{-}CX_2\text{-}H \quad (I)$$

or a pharmaceutically acceptable salt, hydrate, solvate or N-oxide thereof, wherein A, B, C, $R^{11}$ and X are as defined below.

In a second aspect, the invention provides methods of making the prodrugs of formula (I). Specific embodiments of the methods are illustrated in Scheme 1 to 8. In one embodiment, a method for synthesizing compounds according to formula (I) comprises an aza-Michael addition reaction. Aza-Michael addition is described in Basu, Basudeb; Das, Pralay; Hossain, Ismail, "Synthesis of β-amino esters via Aza-Michael addition of amines to alkenes promoted on silica. A useful and recyclable surface.", Synlett (2004); 14:2630-2632, and in Prieto, Auxiliadora; Fernandez, Rosario; Lassaletta, Jose M.; Vazquez, Juan; Alvarez, Eleuterio, "Aza-Michael addition of chiral hydrazines to alkylidene malonates.", Tetrahedron (2005); 61(19):4609-4613. Both of these references are incorporated by reference in their entirety.

In a third aspect, the invention provides prodrug compositions. The compositions generally comprise prodrugs of the invention, or salts, hydrates, solvates, or N-oxides thereof and a suitable excipient, carrier or diluent. The composition may be formulated for veterinary uses or for use in humans.

The prodrugs of the invention, the resultant active drug transformed from the prodrug, or the active compound produced after metabolism are potent inhibitors of HCV replication and/or proliferation. Accordingly, in still a fourth aspect, the invention provides methods of inhibiting HCV replication and/or proliferation, comprising contacting a Hepatitis C virion with an amount of a prodrug or composition of the invention effective to inhibit its replication or proliferation. The methods may be practiced either in vitro or in vivo, and may be used as a therapeutic approach towards the treatment and/or prevention of HCV infections.

In a fifth aspect, the invention provides methods of treating, preventing, and/or inhibiting HCV infections. The methods generally involve administering to a subject that has an HCV infection or that is at risk of developing an HCV infection with an amount of a prodrug or composition of the invention effective to treat or prevent the HCV infection. The method may be practiced in animals in veterinary contexts or in humans.

BRIEF DESCRIPTION OF THE FIGURES

FIG. 1A shows the the portal vein levels of the parent compound and inactive metabolite following oral administration of 5 mg/kg of the parent compound to rats. FIG. 1B shows the dose normalized AUC values for the parent compound following oral administration of 2, 5 and 10 mg/kg of the parent compound.

FIG. 4A shows the prodrug levels in the bile of rats administered an oral dose of 5 mg/kg of prodrug. FIG. 4B shows the concentrations of the parent compound in the bile following administration of either 5 mg/kg of prodrug or 30 mg/kg of the parent compound.

DETAILED DESCRIPTION OF THE INVENTION

Figure 1A:
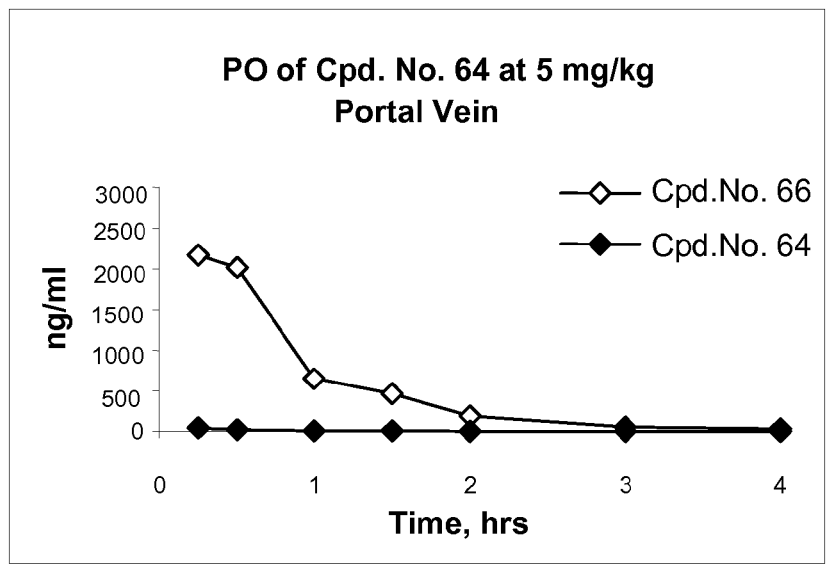
FIGS. 1A and 1B show the portal vein levels of the parent compound and inactive metabolite.

The invention provides compounds, compositions and methods comprising substituted heterocyclic prodrugs that are potent inhibitors of Hepatitis C virus ("HCV") replication and/or proliferation.

In the first aspect, the invention provides compound of the structural formula

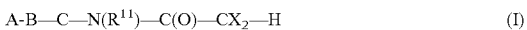

$$A\text{-}B\text{---}C\text{---}N(R^{11})\text{---}C(O)\text{---}CX_2\text{---}H \quad (I)$$

or a pharmaceutically acceptable salt, hydrate, solvate or N-oxide thereof, wherein A is a phenyl or six-membered heteroaryl ring having from one to five of the same or different $R^{20}$ substituents, provided that at least one of the substituents is positioned ortho to ring B;

B is a saturated cycloheteroalkyl, partially unsaturated cycloheteroalkyl, or heteroaryl ring having from one to three annular heteroatoms selected from N, O, and S, where the A and C moieties are attached to non-adjacent ring atoms of B, provided that when B includes more than one annular oxygen atom, the oxygen atoms are not adjacent;

C is a phenyl or a heteroaryl ring, wherein when C is phenyl, it is substituted relative to the B moiety at the meta position with the —N($R^{11}$)—C(O)—$CX_2$—H, or when C is a heteroaryl group, the B moiety and the —N($R^{11}$)—C(O)—$CX_2$—H moiety are positioned on C with only one ring atom of C between them;

$R^{11}$ is selected from the group consisting of —$C_1$-$C_6$ alkyl-C(O)—$OR^9$, —$C_2$-$C_6$ alkenyl-C(O)—O—$R^9$, —(CH$R^{10}$)$_n$-J and $C_1$-$C_6$ alkyl optionally substituted with one or more groups selected from $C_1$-$C_6$ alkyl, —CN and —$NH_2$;

each X is independently —H or halo, provided both X are not H;

n is 0, 1, 2, 3 or 4;

$R^9$ is —H, $C_1$-$C_6$ alkyl, aryl, arylalkyl, heteroaryl, or heteroaralkyl;

each $R^{10}$ is independently —H or lower alkyl;

J is selected from the group consisting of —O—C(O)—O—$R^9$, —O—C(O)—N(H)—CH($R^{13}$)—C(O)—O—$R^9$, —O—$R^9$, —P(O)(O$R^{18}$)O$R^{19}$, —C(=O)—(CH$_2$)$_{0-3}$CH($R^{13}$)—$R^{14}$, —C(=O)—CH($R^{13}$)—NH—C(O)—$R^{14}$, —C(=O)—O$R^9$, —N(H)—C(O)—$R^{21}$, and —N(H)—C(O)—(CH($R^{22}$))$_{1-3}$—N($R^{13}$)—$R^{21}$;

$R^{13}$ is selected from the group consisting of —H, —$NH_2$ and $C_1$-$C_6$ alkyl;

$R^{14}$ is selected from the group consisting of —H, —$NH_2$, $C_1$-$C_6$ alkyl, —$C_0$-$C_6$ alkyl-C(O)—$OR^9$, —P(O)(O$R^{18}$)O$R^{19}$ and —CH($R^{15}$)—N(H)—$R^{21}$;

$R^{15}$ is selected from the group consisting of —H, $C_1$-$C_6$ alkyl, and —$C_1$-$C_6$ alkyl-C(O)—$OR^9$; or $R^{15}$ together with the carbon atom to which it is attached and the nitrogen atom adjacent to the carbon atom form a cycloheteroalkyl group optionally substituted with —OH;

$R^{18}$ is —H, lower alkyl, aryl or arylalkyl;

$R^{19}$ is —H, lower alkyl, aryl or arylalkyl;

$R^{21}$ is selected from the group consisting of —H, $C_1$-$C_6$ alkyl, —O—$R^9$ and —C(O)—O—$R^9$;

$R^{22}$ is selected from the group consisting of —H, aryl, $C_1$-$C_6$ alkyl, and —$C_1$-$C_6$ alkyl-C(O)—$OR^9$; or $R^{22}$ together with the carbon to which it is attached and $R^{13}$ together with the nitrogen to which it is attached form a cycloheteroalkyl group optionally substituted with OH; and each $R^{20}$ is, independently of the other, selected from the group consisting of —OH, —SH, —CN, —C(O)H, —$NO_2$, halo, fluoro, chloro, bromo, iodo, lower alkyl, substituted lower alkyl, lower heteroalkyl, substituted lower heteroalkyl, cycloalkyl, substituted cycloalkyl, cycloheteroalkyl, substituted cycloheteroalkyl, lower haloalkyl, monohalomethyl, dihalomethyl, trihalomethyl, trifluoromethyl, lower alkylthio, substituted lower alkylthio, lower alkoxy, substituted lower alkoxy, methoxy, substituted methoxy, lower heteroalkoxy, substituted lower heteroalkoxy, cycloalkoxy, substituted cycloalkoxy, cycloheteroalkoxy, substituted cycloheteroalkoxy, lower haloalkoxy, monohalomethoxy, dihalomethoxy, trihalomethoxy, trifluoromethoxy, amino, lower di- or monoalkylamino, substituted lower di- or monoalkylamino, aryl, substituted aryl, aryloxy, substituted aryloxy, phenoxy, substituted phenoxy, arylalkyl, substituted arylalkyl, arylalkyloxy, substituted arylalkyloxy, benzyl, benzyloxy, heteroaryl, substituted heteroaryl, heteroaryloxy, substituted heteroaryloxy, heteroarylalkyl, substituted heteroarylalkyl, heteroarylalkyloxy, substituted heteroarylalkyloxy, carboxyl, lower alkoxycarbonyl, substituted lower alkoxycarbonyl, aryloxycarbonyl, substituted aryloxycarbonyl, arylalkyloxycarbonyl, substituted arylalkyloxycarbonyl, carbamate, substituted carbamate, carbamoyl, substituted carbamoyl, thiocarbamoyl, substituted thiocarbamoyl, ureas, substituted ureas, thioureas, substituted thioureas, sulfamoyl, substituted sulfamoyl and a group of the formula -L-$R^3$, where "L" is a linker and $R^8$ is cycloalkyl, substituted cycloalkyl, cycloheteroalkyl or substituted cycloheteroalkyl.

In Embodiment A, the invention provides compounds according to formula (I), wherein A is a phenyl substituted with at least two $R^{20}$ groups selected from the group consisting of halo, lower alkoxy, lower alkyl, lower haloalkyl, wherein at least one of the $R^{20}$ is positioned ortho to ring B;

B is an partially unsaturated cycloheteroalkyl ring having two annular heteroatoms selected from N and O, where the A and C moieties are attached to non-adjacent ring atoms of B;

C is a phenyl substituted relative to the B moiety at the meta position with the —N($R^{11}$)—C(O)—$CX_2$—H;

$R^{11}$ is selected from the group consisting of —(CH$R^{10}$)$_n$-J and $C_1$-$C_6$ alkyl optionally substituted with one or more groups selected from —CN and —$NH_2$;

each X is halo;

n is 1 or 2;

$R^9$ is —H or $C_1$-$C_6$ alkyl;

each $R^{10}$ is independently —H or lower alkyl;

J is selected from the group consisting of —O—$R^9$, —P(O)(O$R^{18}$)O$R^{19}$, —C(=O)—O$R^9$, —N(H)—C(O)—$R^{21}$, and —N(H)—C(O)—CH($R^{22}$)—N($R^{13}$)—$R^{21}$;

$R^{13}$ is selected from the group consisting of —H, and $C_1$-$C_6$ alkyl;

$R^{18}$ is —H or lower alkyl;

$R^{19}$ is —H or lower alkyl;

$R^{21}$ is selected from the group consisting of —H, $C_1$-$C_6$ alkyl, —O—$R^9$, and —C(O)—O—$R^9$;

$R^{22}$ is selected from the group consisting of —H, aryl, $C_1$-$C_6$ alkyl, and —$C_1$-$C_6$ alkyl-C(O)—$OR^9$; and $R^{22}$ together with the carbon to which it is attached and $R^{13}$ together with the nitrogen to which it is attached form a cycloheteroalkyl group optionally substituted with OH.

In Embodiment B, the invention provides compounds according to Embodiment A, except that B is a group of the formula

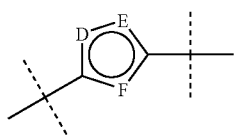

wherein D, E and F are each, independently of one another, selected from N, O and CH, provided that at least two of D, E and F are other than CH and D and E are not both simultaneously O. Preferably, D is O, E is N and F is CH, or D is N, E is O and F is CH. More preferably, B is isoxazolyl, pyrazolyl, oxadiazolyl or triazolyl ring. Still more preferably, B is isoxazolyl.

In Embodiment C, the invention provides compounds according to Embodiment B, wherein X is chloro, and A is substituted at the 2- and 6-positions with the same or different $R^{20}$ substituent. Preferably, one $R^{20}$ is halo and the other $R^{20}$ is lower alkoxy, or lower haloalkyl. More preferably, both $R^{20}$ are halo, wherein halo is chloro.

In Embodiment D, the invention provides compounds according to Embodiment C having the formula

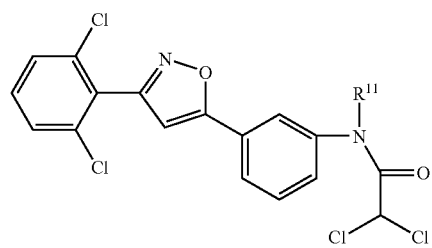

(Ia)

or a pharmaceutically acceptable salt, hydrate, solvate or N-oxide thereof, wherein $R^{11}$ is selected from the group consisting of:

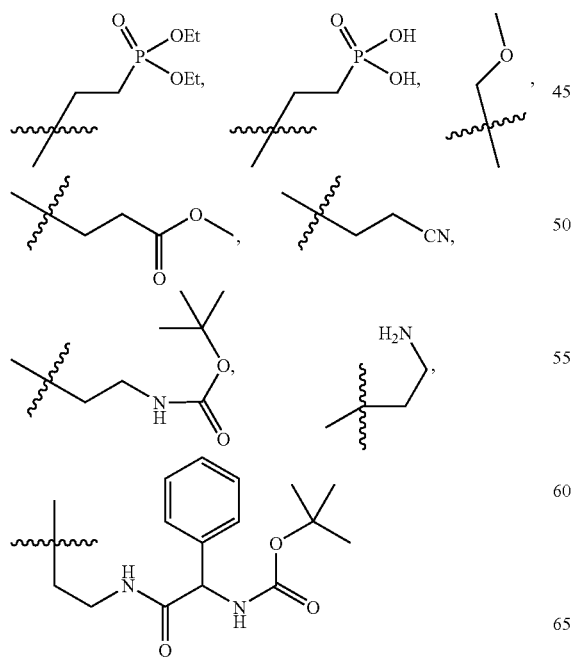

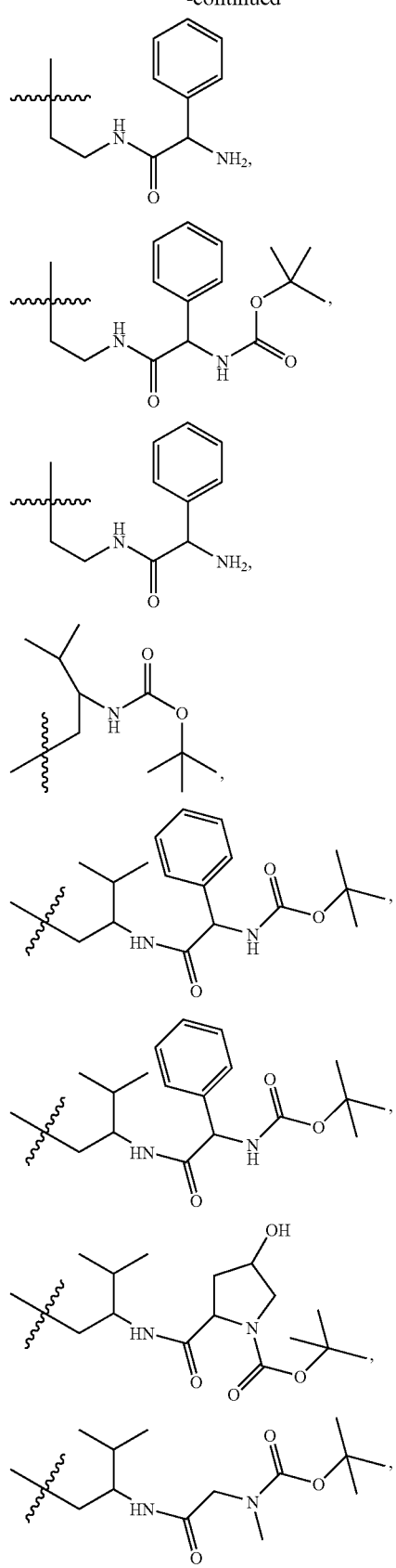

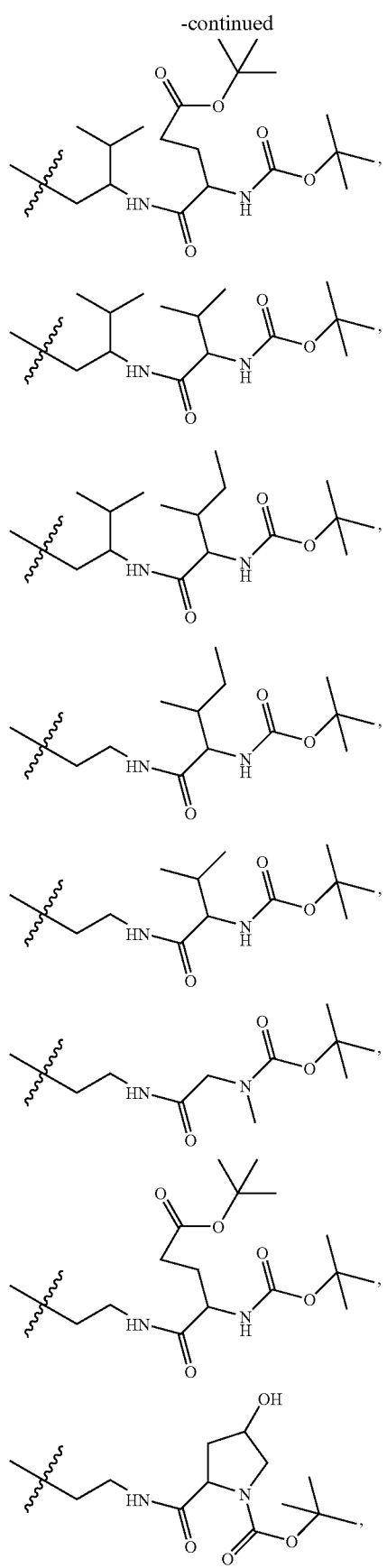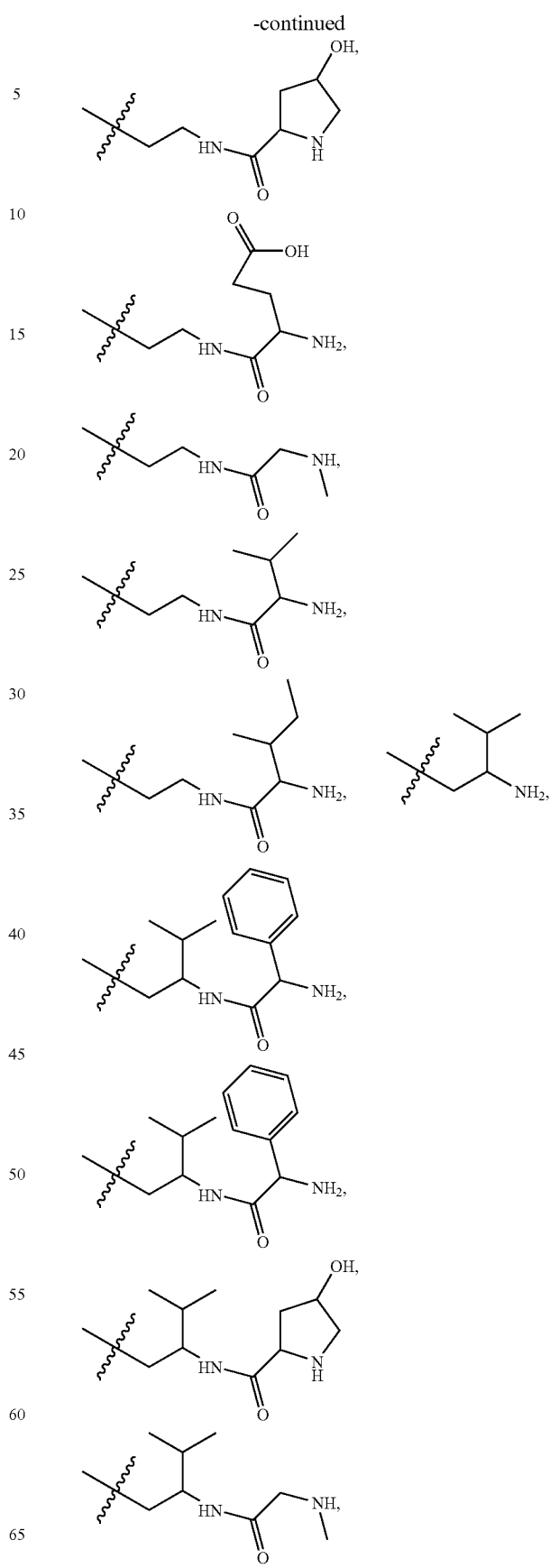

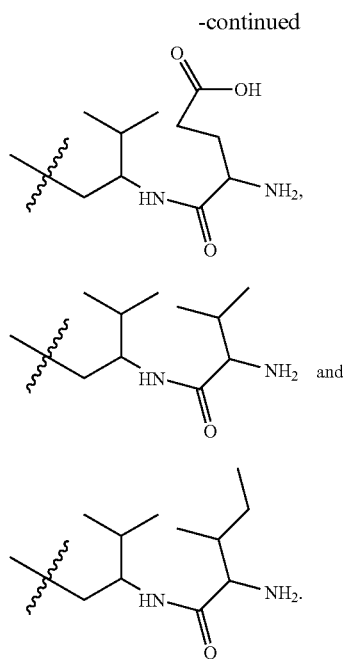
In Embodiment D1, the invention provides compounds according to Embodiment D, wherein $R^{11}$ is selected from the group consisting of:
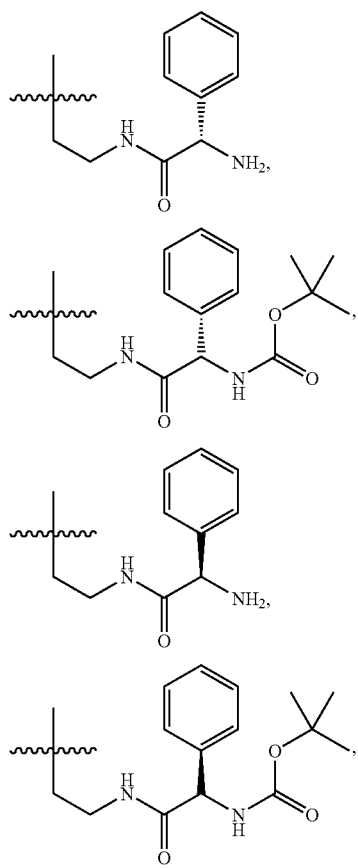
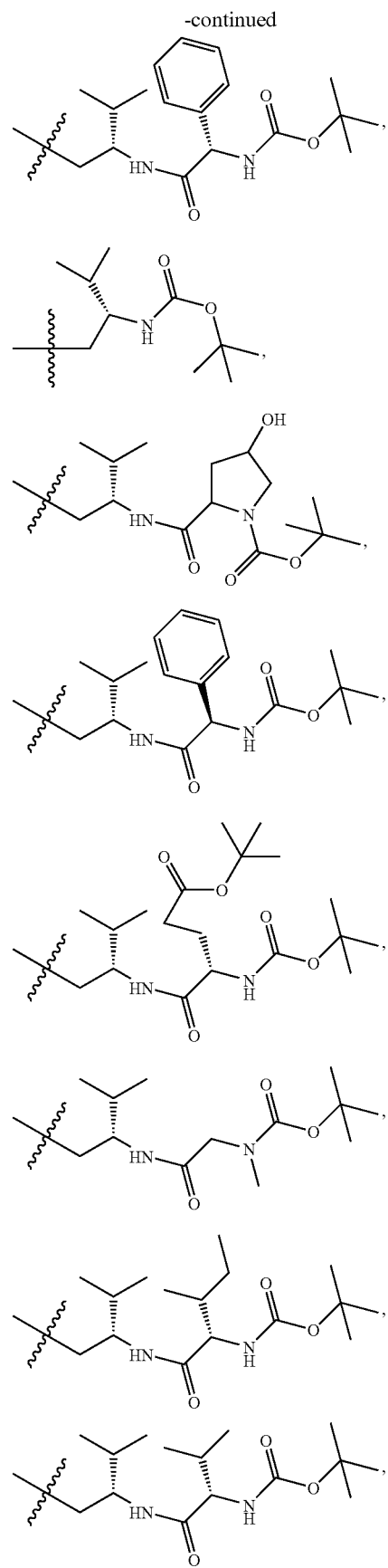

-continued

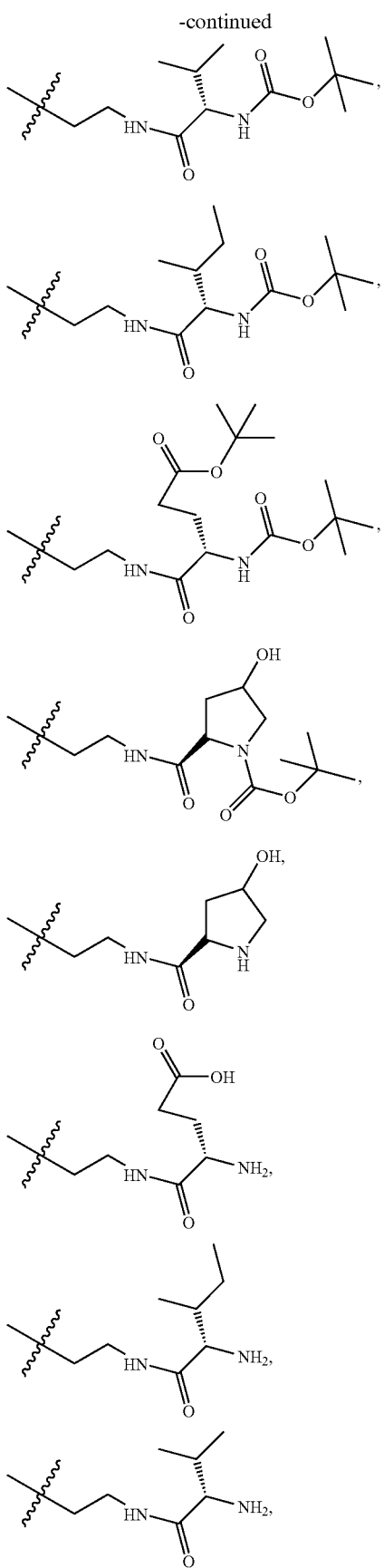

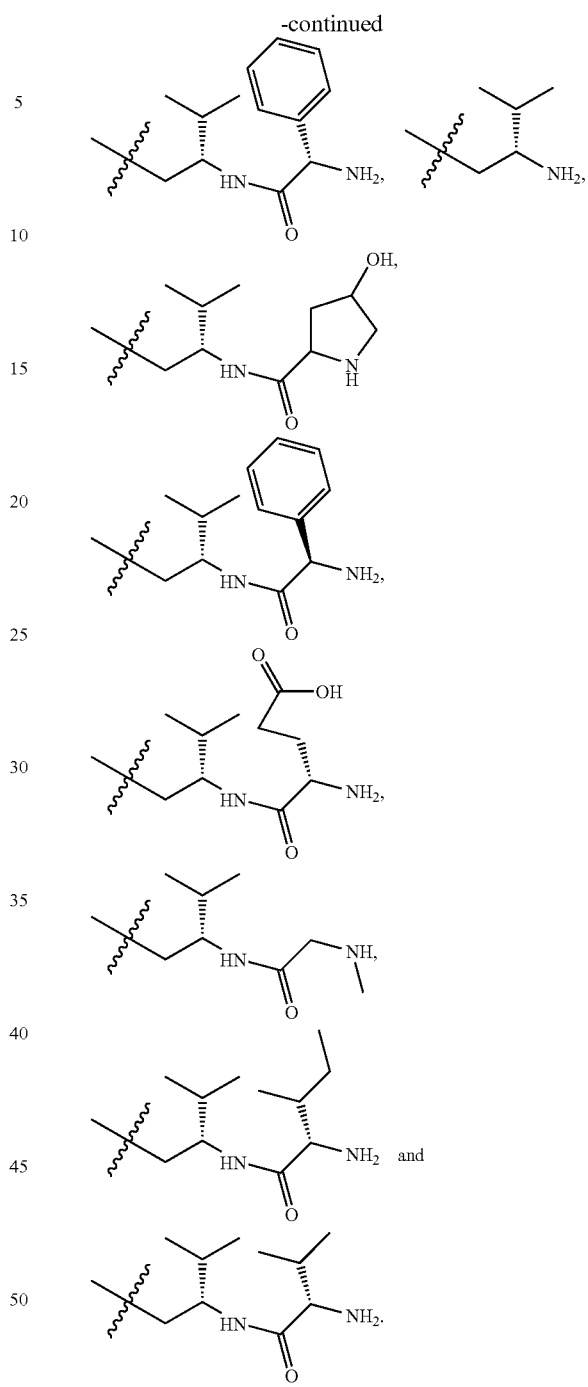

In Embodiment E, the invention provides compounds according to formula (I), wherein A is a phenyl substituted with at least two $R^{20}$ groups selected from the group consisting of halo, lower alkoxy, lower alkyl, lower haloalkyl, wherein at least one of the $R^{20}$ is positioned ortho to ring B;

B is an unsaturated heteroatomic ring having two annular heteroatoms selected from N and O, where the A and C moieties are attached to non-adjacent ring atoms of B, provided that when B includes two annular oxygen atoms they are not adjacent;

C is a pyridinyl wherein the B moiety and the —N(R$^{11}$)—C(O)—CX$_2$—H moiety are positioned on C with only one ring atom of C between them;

R$^{11}$ is selected from the group consisting of —C$_2$-C$_6$ alkenyl-C(O)—O—R$^9$, and —(CHR$^{10}$)$_n$-J;

each X is halo;

n is 1 or 2;

R$^9$ is —H or C$_1$-C$_6$ alkyl;

R$^{10}$ is hydrogen;

J is selected from the group consisting of —O—C(O)—O—R$^9$, —O—C(O)—N(H)—CH(R$^{13}$)—C(O)—O—R$^9$, —O—R$^9$, —C(=O)—(CH$_2$)$_{0-3}$CH(R$^{13}$)—R$^{14}$, —C(=O)—CH(R$^{13}$)—NH—C(O)—R$^{14}$ and —C(=O)—OR$^9$;

R$^{13}$ is selected from the group consisting of —H, —NH$_2$ and C$_1$-C$_6$ alkyl;

R$^{14}$ is selected from the group consisting of —NH$_2$, C$_1$-C$_6$ alkyl, —C$_0$-C$_6$ alkyl-C(O)—OR$^9$, —P(O)(OR$^{18}$)OR$^{19}$ and —CH(R$^{15}$)—N(H)—R$^{21}$;

R$^{15}$ is selected from the group consisting of —H, C$_1$-C$_6$ alkyl, and —C$_1$-C$_6$ alkyl-C(O)—OR$^9$; or R$^{15}$ together with the carbon atom to which it is attached and the nitrogen atom adjacent to the carbon atom form a cycloheteroalkyl group optionally substituted with —OH;

R$^{18}$ is lower alkyl;

R$^{19}$ is lower alkyl; and

R$^{21}$ is selected from the group consisting of —H, —O—R$^9$ and —C(O)—O—R$^9$.

In Embodiment F, the invention provides compounds according to Embodiment E, except that B is a group of the formula

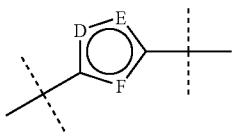

wherein D, E and F are each, independently of one another, selected from N, O and CH, provided that at least two of D, E and F are other than CH and D and E are not both simultaneously O. Preferably, D is O, E is N and F is CH, or D is N, E is O and F is CH. More preferably, B is isoxazolyl, pyrazolyl, oxadiazolyl or triazolyl ring. Still more preferably, B is isoxazolyl.

In Embodiment G, the invention provides compounds according to Embodiment F, wherein X is chloro, and A is substituted at the 2- and 6-positions with the same or different R$^{20}$ substituent. Preferably, one R$^{20}$ is halo and the other R$^{20}$ is lower alkoxy, or lower haloalkyl. More preferably, both R$^{20}$ are halo, wherein halo is chloro.

In Embodiment H, the invention provides compounds according to Embodiment E of the formula

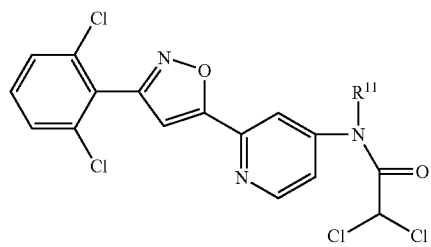

or a pharmaceutically acceptable salt, hydrate, solvate or N-oxide thereof, wherein R$^9$ is —H or C$_1$-C$_6$ alkyl;

R$^{11}$ is selected from the group consisting of —(CH$_2$)$_2$—C(=O)—CH(R$^{13}$)—R$^{14}$, —(CH$_2$)$_2$—C(=O)—(CH$_2$)$_{1-3}$CH(R$^{13}$)—R$^{14}$ and —(CH$_2$)$_2$—C(=O)—CH(R$^{13}$)—NH—C(O)—R$^{14}$;

R$^{13}$ is selected from the group consisting of —H, —NH$_2$ and C$_1$-C$_6$ alkyl;

R$^{14}$ is selected from the group consisting of C$_1$-C$_6$ alkyl, —C$_0$-C$_6$ alkyl-C(O)—OR$^9$ and —CH(R$^{15}$)—N(H)—R$^{21}$;

R$^{15}$ is selected from the group consisting of —H, C$_1$-C$_6$ alkyl, and —C$_1$-C$_6$ alkyl-C(O)—OR$^9$; or R$^{15}$ together with the carbon atom to which it is attached and the nitrogen atom adjacent to the carbon atom form a cycloheteroalkyl group optionally substituted with —OH; and R$^{21}$ is selected from the group consisting of —H and —C(O)—O—R$^9$.

In Embodiment I, the invention provides compounds according to Embodiment H, wherein R$^{11}$ is —(CH$_2$)$_2$—C(=O)—CH(R$^{13}$)—R$^{14}$. Preferably, R$^{13}$ is —H or —NH$_2$ and R$^{14}$ is —NH$_2$, C$_1$-C$_3$ alkyl or —C$_1$-C$_5$ alkyl-C(O)—OH. Preferably, R$^{14}$ is isopropyl or isobutyl or —(CH$_2$)—C(O)—OH.

In Embodiment J, the invention provides compounds according to Embodiment H, wherein R$^{11}$ is —(CH$_2$)$_2$—C(=O)—(CH$_2$)$_2$CH(R$^{13}$)—R$^{14}$. Preferably, R$^{13}$ is —NH$_2$ and R$^{14}$ is —C$_0$-C$_3$ alkyl-C(O)—OH. Preferably, R$^{14}$ is —C(O)—OH.

In Embodiment K, the invention provides compounds according to Embodiment H, wherein R$^{11}$ is —(CH$_2$)$_2$—C(=O)—CH(R$^{13}$)—NH—C(O)—R$^{14}$. Preferably, R$^{13}$ is —H or C$_1$-C$_4$ alkyl, and R$^{14}$ is —CH(R$^{15}$)—N(H)—R$^{21}$. Preferably, R$^{13}$ is isopropyl, and R$^{14}$ is —CH(R$^{15}$)—N(H)—R$^{21}$. More preferably, R$^{15}$ is isopropyl, and R$^{21}$ is —H or —C(O)—O—C$_1$-C$_5$ alkyl. Still more preferably, R$^{21}$ is —C(O)—O-tert-butyl.

In Embodiment L, the invention provides compounds according to Embodiment K, wherein R$^{15}$ is —H, and R$^{21}$ is —H or —C(O)—O—C$_1$-C$_5$ alkyl. Preferably, R$^{21}$ is —C(O)—O-tert-butyl.

In Embodiment M, the invention provides compounds according to Embodiment K, wherein R$^{15}$ together with the carbon atom to which it is attached and the nitrogen atom adjacent to the carbon atom form a pyrrolidinyl group substituted with —OH, and R$^{21}$ is —C(O)—O-tert-butyl.

In Embodiment N, the invention provides compounds according to Embodiment K, wherein R$^{15}$ is —C$_1$-C$_3$ alkyl-C(O)—OR$^9$, and R$^{21}$ is —H or —C(O)—O—C$_1$-C$_5$ alkyl. Preferably, R$^{15}$ is —(CH$_2$)$_2$—C(O)—OR$^9$, and R$^{21}$ is —H or —C(O)—O-tert-butyl. More preferably, R$^9$ is -tert-butyl or —H.

In Embodiment O, the invention provides compounds according to Embodiment E of the formula

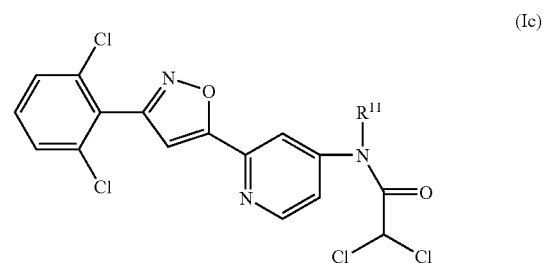

or a pharmaceutically acceptable salt, hydrate, solvate or N-oxide thereof, wherein $R^{11}$ is selected from the group consisting of:
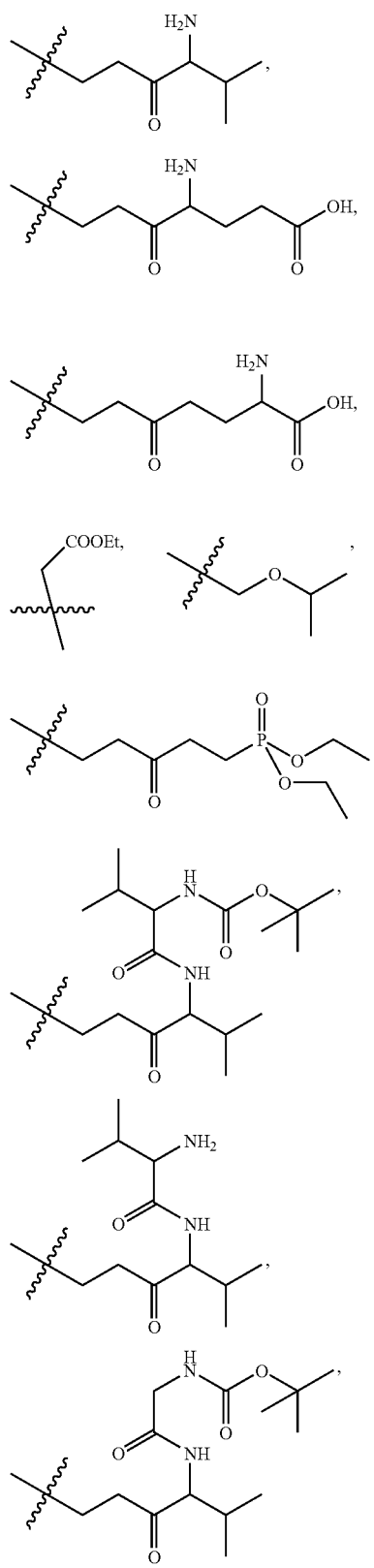
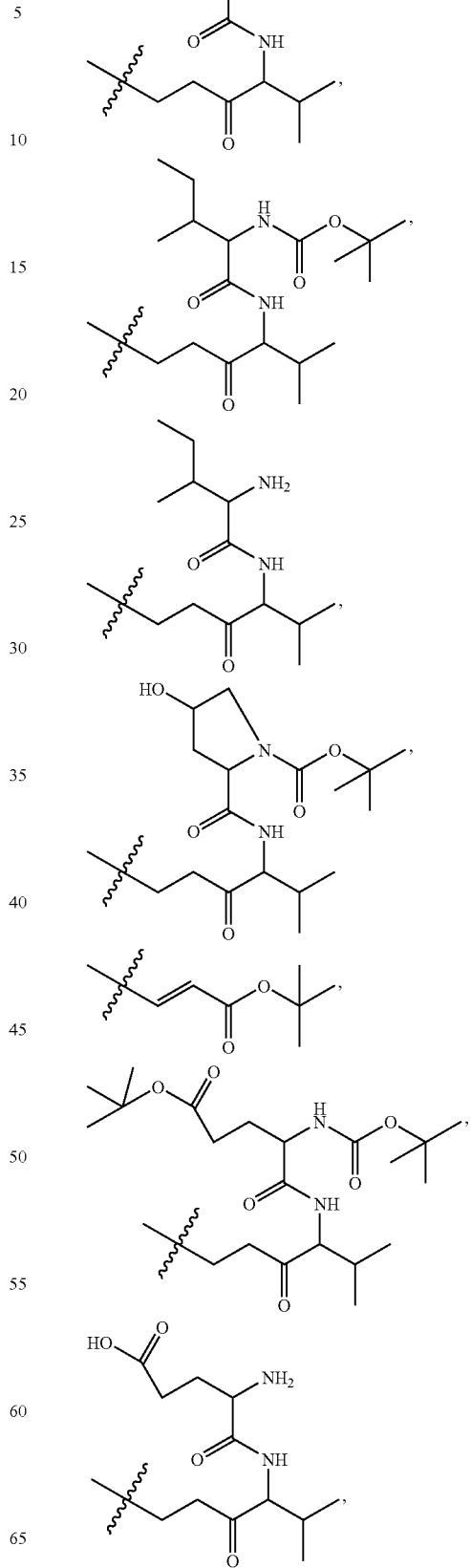

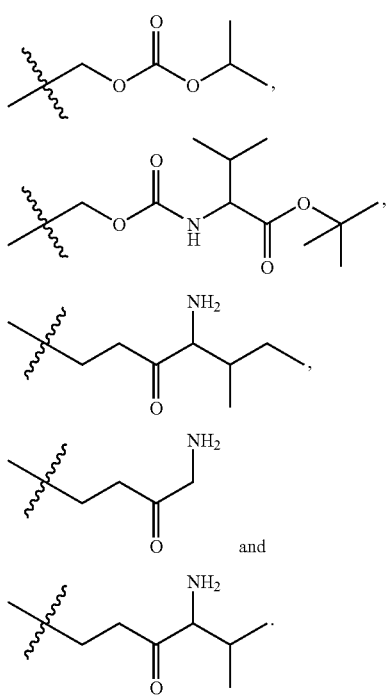

In Embodiment O1, the invention provides compounds according to Embodiment O, wherein $R^{11}$ is selected from the group consisting of:

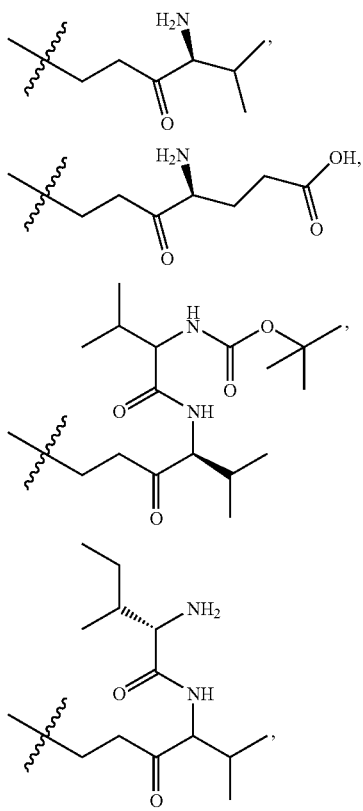
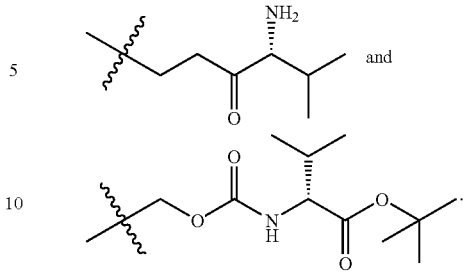

In Embodiment P, the invention provides compounds according to formula (I), wherein when administered to a cell comprising a hepatitis C virion, the compound inhibits HCV replication and/or proliferation and has an IC50 of 10 μM or less, as measured in an in vitro assay.

In Embodiment Q, the invention provides compounds according to Embodiment A of the formula

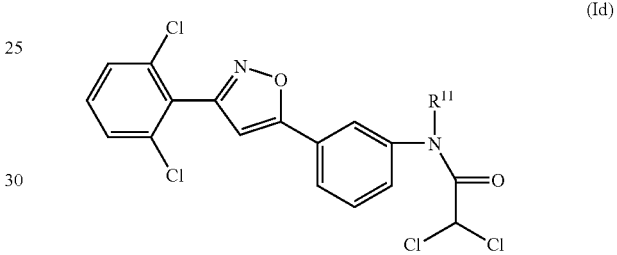

or a pharmaceutically acceptable salt, hydrate, solvate or N-oxide thereof, wherein $R^{11}$ is selected from the group consisting of —(CH$_2$)$_2$—N(H)—C(O)—R$^{21}$, —(CHR$^{10}$)$_n$—N(H)—C(O)—R$^{21}$, and —(CHR$^{10}$)$_n$—N(H)—C(O)—CH(R$^{22}$)—N(R$^{13}$)—R$^{21}$;

n is 2;

$R^{10}$ is —H or $C_1$-$C_6$ alkyl;

$R^{13}$ is —H or $C_1$-$C_6$ alkyl;

$R^{18}$ is —H or $C_1$-$C_6$ alkyl;

$R^{19}$ is —H or $C_1$-$C_6$ alkyl;

$R^{21}$ is selected from the group consisting of —H, $C_1$-$C_6$ alkyl, and —C(O)—O—$C_1$-$C_6$ alkyl;

$R^{22}$ is selected from the group consisting of —H, aryl, $C_1$-$C_6$ alkyl, —$C_1$-$C_6$ alkyl-C(O)—OH, and —$C_1$-$C_6$ alkyl-C(O)—O—$C_1$-$C_6$ alkyl; and $R^{22}$ together with the carbon to which it is attached and $R^{13}$ together with the nitrogen to which it is attached form a cycloheteroalkyl group substituted with —OH.

In Embodiment R, the invention provides compounds according to Embodiment Q, wherein $R^{11}$ is —(CH$_2$)$_2$—N(H)—C(O)—R$^{21}$. Preferably, $R^{21}$ is —C(O)—O-tert-butyl.

In Embodiment S, the invention provides compounds according to Embodiment Q, wherein $R^{11}$ is —(CHR$^{10}$)$_2$—N(H)—C(O)—R$^{21}$. Preferably, $R^{10}$ is $C_1$-$C_4$ alkyl, and $R^{21}$ is —C(O)—O—$C_1$-$C_5$ alkyl. More preferably, $R^{10}$ is isopropyl and $R^{21}$ is —C(O)—O-tert-butyl.

In Embodiment T, the invention provides compounds according to Embodiment Q, wherein $R^{11}$ is —(CH$_2$)$_2$—N(H)—C(O)—CH(R$^{22}$)—N(R$^{13}$)—R$^{21}$. Preferably, $R^{22}$ is aryl, —H, $C_1$-$C_5$ alkyl, —$C_1$-$C_3$ alkyl-C(O)—OH or —$C_1$-$C_3$ alkyl-C(O)—O—$C_1$-$C_5$ alkyl, $R^{13}$ is —H or $C_1$-$C_3$ alkyl, and $R^{21}$ is —H, $C_1$-$C_3$ alkyl or —C(O)—O—$C_1$-$C_5$ alkyl. More preferably, $R^{22}$ is phenyl, isobutyl, isopropyl, —$(CH_2)_2$—C(O)—OH, or —$(CH_2)_2$—C(O)—O-tert-butyl, $R^{13}$ is —$CH_3$, and $R^{21}$ is —$CH_3$ or —C(O)—O-tert-butyl.

In Embodiment U, the invention provides compounds according to Embodiment Q, wherein $R^{11}$ is —$CH_2$—$(CHR^{10})$—N(H)—C(O)—CH($R^{22}$)—N($R^{13}$)—$R^{21}$. Preferably, $R^{10}$ is $C_1$-$C_4$ alkyl, $R^{22}$ is aryl, —H, $C_1$-$C_5$ alkyl, —$C_1$-$C_3$ alkyl-C(O)—OH or —$C_1$-$C_3$ alkyl-C(O)—O—$C_1$-$C_5$ alkyl, $R^{13}$ is —H or $C_1$-$C_3$ alkyl, and $R^{21}$ is —H, $C_1$-$C_3$ alkyl or —C(O)—O—$C_1$-$C_5$ alkyl. More preferably, $R^{10}$ is isopropyl, $R^{22}$ is phenyl, isobutyl, isopropyl, —$(CH_2)_2$—C(O)—OH or —$(CH_2)_2$—C(O)—O-tert-butyl, $R^{13}$ is —$CH_3$, and $R^{21}$ is —$CH_3$ or —C(O)—O-tert-butyl.

In the third aspect, the invention provides a composition comprising a pharmaceutically acceptable vehicle and a compound according to the first aspect or any one of Embodiments A to U.

In the fourth aspect, the invention provides a method of inhibiting replication and/or proliferation of a hepatitis C ("HC") virion, comprising the step of contacting an HC virion with an amount of a compound according to the first aspect or any one of Embodiments A to U effective to inhibit replication and/or proliferation of the HC virion. Preferably, the method is practiced in vitro. More preferably, the method is practised in vivo.

In the fifth aspect, the invention provides a method of treating or preventing an HCV infection, comprising the step of administering to a subject an amount of a compound according to the first aspect or any one of Embodiments A to U effective to treat or prevent an HCV infection. Preferably, the subject is a human. Preferably, the compound is administered in an amount of about 0.01 mg/kg/day to 200 mg/kg/day. More preferably, the compound is administered in an amount of about 1 mg/kg/day to 100 mg/kg/day. Also preferred is wherein the compound is administered orally, intravenously or subcutaneously. Still more preferably, the methods is practiced therapeutically in a subject having an HCV infection. Also preferred is wherein the method is practiced prophylactically in a subject at risk of developing an HCV infection.

Prodrugs having the structural formulae (I) can be prepared from heterocyclic compounds described in U.S. Ser. No. 10/286,017, filed Nov. 1, 2002, 60/467,650, filed May 2, 2003, 60/467,811, filed May 2, 2003, Ser. No. 10/440,349, filed May 15, 2003, Ser. No. 10/646,348, filed Aug. 22, 2003, the contents of which are incorporated herein in their entirety.

In Embodiment W according to the second aspect, some starting materials used for making compounds of the invention according to formula (I) are according to structural formula (III) wherein A, B and C are as previously defined. Compounds of formula (III) are used to make, for example, corresponding halo acetamide "parent" compounds (IIa), via acylation of the —$NH_2$ group. Alternatively, Compounds of formula (III) are used to make intermediate compounds (IIb), via reaction with the —$NH_2$ group, where $R^{11}$ is as previously defined, or in this case, precursors to those groups defined for $R^{11}$. Compounds (IIa) and (IIb) are converted to prodrugs of the invention according to formula (I). Conversion of (IIa) and (IIb) to prodrugs of the invention can be accomplished by, for example, alkylation chemistry, hemi-aminal formation, acylation with amino acids and then reduction, reductive amination chemistry and 1,4-addition reactions to unsaturated systems. Further details of these chemistries are described in the specific examples below.

A-B—C—$NH_2$ (III)

A-B—C—NH—C(=O)CH$X_2$ (IIa)

A-B—C—NH—$R_{11}$ (IIb)

In Embodiment X, according to the second aspect, pro-groups $R^{11}$ or halo acetamide groups of the invention may be pre-incorporated into, for example, an intermediate containing ring C. In one example, such intermediates contain an alkynyl group that is used in conjunction with another intermediate containing ring A. When combined, for example in a [3+2] cycloaddition reaction to form ring B, compounds according to (IIa) or (IIb), or precursors thereto, are formed.

Also specifically described are combinations of the above specific embodiments.

Definitions

"Alkl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as t-butyl, isopropyl, propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. Preferably, an alkyl group comprises from 1 to 15 carbon atoms ($C_1$-$C_{15}$ alkyl), more preferably from 1 to 10 carbon atoms ($C_1$-$C_{10}$ alkyl) and even more preferably from 1 to 6 carbon atoms ($C_1$-$C_6$ alkyl or lower alkyl).

The term "lower" when used as a modifer of alkyl or an alkyl containing moiety such as alkoxy, alkylthio, etc., means that the that the "alkyl" portion of the moiety consists of from 1 to 6 carbon atoms, except for "lower heteroalkyl", which refers to a straight or branched chain moiety of from 2-6 backbone atoms in which one or more are heteroatoms and the reminaing are carbon. So for example, "lower alkyl" refers to a $C_1$-$C_6$-alkyl, "lower alkoxy" refers to $C_1$-$C_6$-alkyl-O—, "lower monoalkylamino" refers to ($C_1$-$C_6$-alkyl)NH—, etc.

"Alkanyl," by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkyldiyl" by itself or as part of another substituent refers to a saturated or unsaturated, branched, straight-chain or cyclic divalent hydrocarbon group derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. In preferred embodiments, the alkyldiyl group comprises from 1 to 6 carbon atoms (C1-C6 alkyldiyl). Also preferred are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenos, defined infra).

"Alkyleno," by itself or as part of another substituent, refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkyleno is indicated in square brackets. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkyleno group is $(C_1$-$C_6)$ or $(C_1$-$C_3)$ alkyleno. Also preferred are straight-chain saturated alkano groups, e.g., methano, ethano, propano, butano, and the like.

"Alkoxy," by itself or as part of another substituent, refers to a radical of the formula —OR, where R is an alkyl or cycloalkyl group as defined herein. Representative examples alkoxy groups include, but are not limited to, methoxy, ethoxy, propoxy, isopropoxy, butoxy, tert-butoxy, cyclopropyloxy, cyclopentyloxy, cyclohexyloxy and the like.

"Alkoxycarbonyl," by itself or as part of another substituent, refers to a radical of the formula —C(O)-alkoxy, where alkoxy is as defined herein.

"Alkylthio," by itself or as part of another substituent, refers to a radical of the formula —SR, where R is an alkyl or cycloalkyl group as defined herein. Representative examples of Alkylthio groups include, but are not limited to, methylthio, ethylthio, propylthio, isopropylthio, butylthio tert-butylthio, cyclopropylthio, cyclopentylthio, cyclohexylthio, and the like.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Preferably, an aryl group comprises from 6 to 20 carbon atoms ($C_6$-$C_{20}$ aryl), more preferably from 6 to 15 carbon atoms ($C_6$-$C_{15}$ aryl) and even more preferably from 6 to 10 carbon atoms ($C_6$-$C_{10}$ aryl).

"Arylalkyl," by itself or as part of another substituent, refers to an acyclic alkyl group in which one of the hydrogen atoms bonded to a carbon atom, typically a terminal or sp carbon atom, is replaced with an aryl group as, as defined herein. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. Preferably, an arylalkyl group is ($C_6$-$C_{30}$) arylalkyl, e.g., the alkanyl, alkenyl or alkynyl moiety of the arylalkyl group is ($C_1$-$C_{10}$) alkyl and the aryl moiety is ($C_6$-$C_{20}$) aryl, more preferably, an arylalkyl group is ($C_6$-$C_{20}$) arylalkyl, e.g., the alkanyl, alkenyl or alkynyl moiety of the arylalkyl group is ($C_1$-$C_8$) alkyl and the aryl moiety is ($C_6$-$C_{12}$) aryl, and even more preferably, an arylalkyl group is ($C_6$-$C_{15}$) arylalkyl, e.g., the alkanyl, alkenyl or alkynyl moiety of the arylalkyl group is ($C_1$-$C_5$) alkyl and the aryl moiety is ($C_6$-$C_{10}$) aryl.

"Aryloxy," by itself or as part of another substituent, refers to a radical of the formula —O-aryl, where aryl is as defined herein.

"Arylalkyloxy" by itself or as part of another substituent, refers to a radical of the formula —O-arylalkyl, where arylalkyl is as defined herein.

"Aryloxycarbonyl," by itself or as part of another substituent, refers to a radical of the formula —C(O)—O-aryl, where aryl is as defined herein.

"Carbamoyl," by itself or as part of another substituent, refers to a radical of the formula —C(O)NR'R", where R' and R" are each, independently of one another, selected from the group consisting of hydrogen, alkyl and cycloalkyl as defined herein, or alternatively, R' and R", taken together with the nitrogen atom to which they are bonded, form a 5-, 6- or 7-membered cycloheteroalkyl ring as defined herein, which may optionally include from 1 to 4 of the same or different additional heteroatoms selected from the group consisting of O, S and N.

"Cycloalkyl," by itself or as part of another substituent, refers to a saturated or unsaturated cyclic alkyl radical, as defined herein. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. Preferably, the cycloalkyl group comprises from 3 to 10 ring atoms ($C_3$-$C_{10}$ cycloalkyl) and more preferably from 3 to 7 ring atoms ($C_3$-$C_7$ cycloalkyl). The cycloalkyl group also includes polycyclic groups such as, but not limited to, adamantane, and the like.

"Cycloheteroalkyl" by itself or as part of another substituent, refers to a saturated or unsaturated cyclic alkyl radical in which one or more carbon atoms (and optionally any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidone, quinuclidine, and the like. Preferably, the cycloheteroalkyl group comprises from 3 to 10 ring atoms (3-10 membered cycloheteroalkyl) and more preferably from 5 to 7 ring atoms (5-7 membered cycloheteroalkyl).

A cycloheteroalkyl group may be substituted at a heteroatom, for example, a nitrogen atom, with a lower alkyl group. As specific examples, N-methyl-imidazolidinyl, N-methyl-morpholinyl, N-methyl-piperazinyl, N-methyl-piperidinyl, N-methyl-pyrazolidinyl and N-methyl-pyrrolidinyl are included within the definition of "cycloheteroalkyl." A cycloheteralkyl group may be attached to the remainder of the molecule via a ring carbon atom or a ring heteroatom.

The term "heterocycle" as used herein mean a cycloheteroalkyl, heteroaryl or parent heteroaromatic ring system. Heterocycle includes groups that are, for example, saturated, unsaturated, or aromatic heteroatomic ring systems.

"Dialkylamino" or "Monoalkylamino," by themselves or as part of other substituents, refer to radicals of the formula —NRR and —NHR, respectively, where each R is independently selected from the group consisting of alkyl and cycloalkyl, as defined herein. Representative examples of dialkylamino groups include, but are not limited to, dimethylamino, methylethylamino, di-(1-methylethyl)amino, (cyclohexyl)(methyl)amino, (cyclohexyl)(ethyl)amino, (cyclohexyl)(propyl)amino and the like. Representative examples of monalkylamino groups include, but are not limited to, methylamino, ethylamino, propylamino, isopropylamino, cyclohexylamino, and the like.

"Halogen" or "Halo," by themselves or as part of another substituent, refer to a fluoro, chloro, bromo and/or iodo radical.

"Haloalkyl," by itself or as part of another substituent, refers to an alkyl group as defined herein in which one or more of the hydrogen atoms is replaced with a halo group. The term "haloalkyl" is specifically meant to include monohaloalkyls, dihaloalkyls, trihaloalkyls, etc. up to perhaloalkyls. The halo groups substituting a haloalkyl can be the same, or they can be different. For example, the expression "($C_1$-$C_2$) haloalkyl" includes 1-fluoromethyl, 1-fluoro-2-chloroethyl, difluoromethyl, trifluoromethyl, 1-fluoroethyl, 1,1-difluoroethyl, 1,2-difluoroethyl, 1,1,1-trifluoroethyl, perfluoroethyl, etc.

"Haloalkyloxy," by itself or as part of another substituent, refers to a group of the formula —O-haloalkyl, where haloalkyl is as defined herein.

"Heteroalkyl," "Heteroalkanyl," "Heteroalkenyl," "Heteroalkynyl," "Heteroalkyldiyl" and "Heteroalkyleno," by themselves or as part of other substituents, refer to alkyl, alkanyl, alkenyl, alkynyl, alkyldiyl and alkyleno groups, respectively, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, O, S, N, Si, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Examples of such heteroalkyl, heteroalkanyl, heteroalkenyl and/or heteroalkynyl groups include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$, —CH$_2$—CH$_2$—S(O)—CH$_3$, —CH$_2$—CH$_2$—S(O)$_2$—CH$_3$, —CH=CH—O—CH$_3$, —CH$_2$—CH=N—O—CH$_3$, and —CH$_2$—CH$_2$—O—C≡CH. For heteroalkyldiyl and heteroalkyleno groups, the heteratom or heteratomic group can also occupy either or both chain termini. For such groups, no orientation of the group is implied.

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, □-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group comprises from 5 to 20 ring atoms (5-20 membered heteroaryl), more preferably from 5 to 10 ring atoms (5-10 membered heteroaryl). Preferred heteroaryl groups are those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylakenyl and/or heteroarylalkynyl is used. In preferred embodiments, the heteroarylalkyl group is a 6-21 membered heteroarylalkyl, e.g., the alkanyl, alkenyl or alkynyl moiety of the heteroarylalkyl is (C1-C6) alkyl and the heteroaryl moiety is a 5-15-membered heteroaryl. In particularly preferred embodiments, the heteroarylalkyl is a 6-13 membered heteroarylalkyl, e.g., the alkanyl, alkenyl or alkynyl moiety is (C1-C3) alkyl and the heteroaryl moiety is a 5-10 membered heteroaryl.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" refers to a parent aromatic ring system in which one or more carbon atoms (and optionally any associated hydrogen atoms) are each independently replaced with the same or different heteroatom. Typical heteroatoms to replace the carbon atoms include, but are not limited to, N, P, O, S, Si, etc. Specifically included within the definition of "parent heteroaromatic ring system" are fused ring systems in which one or more of the rings are aromatic and one or more of the rings are saturated or unsaturated, such as, for example, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Pharmaceutically acceptable salt" refers to a salt of a compound of the invention which is made with counterions understood in the art to be generally acceptable for pharmaceutical uses and which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like; or (2) salts formed when an acidic proton present in the parent compound is replaced by a metal ion, e.g., an alkali metal ion, an alkaline earth ion, or an aluminum ion; or coordinates with an inorganic base such as ammonium hydroxide, lithium hydroxide, potassium hydroxide, sodium hydroxide, calcium hydroxide, magnesium hydroxide and the like; or an organic base such as ethanolamine, diethanolamine, triethanolamine, N-methylglucamine, morpholine, piperidine, dimethylamine, diethylamine and the like. Also included are salts of amino acids such as arginates and the like, and salts of organic acids like glucurmic or galactunoric acids and the like (see, e.g., Berge et al., 1977, *J. Pharm. Sci.* 66:1-19).

"Pharmaceutically acceptable vehicle" refers to a diluent, adjuvant, excipient or carrier that is acceptable for human use.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, $3^{rd}$ Ed., 1999, John Wiley & Sons, NY and Harrison et al., *Compendium of Synthetic Organic Methods*, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (e.g., methyl and ethyl esters, acetate or propionate groups or glycol esters) or alkylated such as benzyl and trityl ethers, as well as alkyl ethers, tetrahydropyranyl ethers, trialkylsilyl ethers (e.g., TMS or TIPPS groups) and allyl ethers.

"Progroup" refers to a type of protecting group that, when used to mask a functional group within an active drug to form a promoiety, converts the drug into a prodrug. Progroups are typically attached to the functional group of the drug via bonds that are cleavable under specified conditions of use. Thus, a progroup is that portion of a promoiety that cleaves to release the functional group under the specified conditions of use.

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$CH_2$—$P(O)(OR^b)(OR^b)$, —O—$P(O)(OR^b)(OR^b)$, $P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$'s are taken together with the nitrogen atom to which they are bonded form a 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl.

Similarly, substituent groups useful for substituting unsaturated carbon atoms in the specified group or radical include, but are not limited to, —$R^a$ optionally substituted with $C_1$-$C_4$- alkyl or C(O)OR$^b$, halo, —O$^-$, —O—(CH$_2$)$_{0\text{-}4}$—R$^b$, —SR$^b$, —S$^-$, —NR$^c$R$^c$, trihalomethyl, —CF$_3$, —CN, —OCN, —SCN, —NO, —NO$_2$, —N$_3$, —S(O)$_2$R$^b$, —S(O)$_2$O$^-$, —S(O)$_2$OR$^b$, —OS(O)$_2$R$^b$, —OS(O)$_2$O$^-$, —OS(O)$_2$OR$^b$, —P(O)(O$^-$)$_2$, —P(O)(OR$^b$)(O$^-$), —P(O)(OR$^b$)(OR$^b$), —C(O)R$^b$, —C(S)R$^b$, —C(NR$^b$)R$^b$, —C(O)O$^-$, —C(O)OR$^b$, C(S)OR$^b$, —C(O)NR$^c$R$^c$, —C(NR$^b$)NR$^c$R$^c$, —OC(O)R$^b$, —OC(S)R$^b$, —OC(O)O$^-$, —OC(O)OR$^b$, —O—C(O)—NH—R$^b$, —OC(S)OR$^b$, —NR$^b$C(O)R$^b$, —NR$^b$C(S)R$^b$, —NR$^b$C(O)O$^-$, —NR$^b$C(O)OR$^b$, —NR$^b$C(S)OR$^b$, —NR$^b$C(O)NR$^c$R$^c$, —NR$^b$C(NR$^b$)R$^b$ and —NR$^b$C(NR$^b$)NR$^c$R$^c$, where R$^a$, R$^b$ and R$^c$ are as previously defined. Additional substituent groups for substituting unsaturated carbon atoms are C$_1$-C$_4$-alkyl moieties substituted with one of the foregoing moieties.

Substituent groups useful for substituting nitrogen atoms in heteroalkyl and cycloheteroalkyl groups include, but are not limited to, —R$^a$, —O$^-$, —OR$^b$, —SR$^b$, —S$^-$, —NR$^c$R$^c$, trihalomethyl, —CF$_3$, —CN, —NO, —NO$_2$, —S(O)$_2$R$^b$, —S(O)$_3$O$^-$, —S(O)$_2$OR$^b$, —OS(O)$_2$R$^b$, —OS(O)$_2$O$^-$, —OS(O)$_2$OR$^b$, —P(O)(O$^-$)$_2$, —P(O)(OR$^b$)(O$^-$), —P(O)(OR$^b$)(OR$^b$), —C(O)R$^b$, —C(S)R$^b$, —C(NR$^b$)R$^b$, —C(O)OR$^b$, —C(S)OR$^b$, —C(O)NR$^c$R$^c$, —C(NR$^b$)NR$^c$R$^c$, —OC(O)R$^b$, —OC(S)R$^b$, —OC(O)OR$^b$, —OC(S)OR$^b$, —NR$^b$C(O)R$^b$, —NR$^b$C(S)R$^b$, —NR$^b$C(O)OR$^b$, —NR$^b$C(S)OR$^b$, —NR$^b$C(O)NR$^c$R$^c$, —NR$^b$C(NR$^b$)R$^b$ and —NR$^b$C(NR$^b$)NR$^c$R$^c$, where R$^a$, R$^b$ and R$^c$ are as previously defined.

Substituent groups from the above lists useful for substituting other specified groups or atoms will be apparent to those of skill in the art.

The substituents used to substitute a specified group can be further substituted, typically with one or more of the same or different groups selected from the various groups specified above.

"Sulfamoyl," by itself or as part of another substituent, refers to a radical of the formula —S(O)$_2$NR'R", where R' and R" are each, independently of one another, selected from the group consisting of hydrogen, alkyl and cycloalkyl as defined herein, or alternatively, R' and R", taken together with the nitrogen atom to which they are bonded, form a 5-, 6- or 7-membered cycloheteroalkyl ring as defined herein, which may optionally include from 1 to 4 of the same or different additional heteroatoms selected from the group consisting of O, S and N.

The term "linker" refers to any combination of atoms or groups useful for spacing one molecular moiety from another selected from the following and having a total molecular weight of 200 amu or less: acyclic hydrocarbon bridge (e.g., a saturated or unsaturated, and/or bridged, alkyleno such as methano, ethano, etheno, propano, prop[1]eno, butano, but[1]eno, but[2]eno, buta[1,3]dieno), a mono-, bi- or tri-cyclic hydrocarbon bridge (e.g., [1,2]benzeno, [2,3]naphthaleno, cyclohexane-1,4-diyl), a acyclic heteroatomic or heteroalkyldiyl bridge (e.g., —O—, —S—, —S—O—, —NH—, —PH—, —C(O)—, —C(O)NH—, —OC(O)NH—, —S(O)—, —S(O)$_2$—, —S(O)NH—, —S(O)$_2$NH—, —O—CH$_2$—, —CH$_2$—O—CH$_2$—, —O—CH=CH—CH$_2$—), a mono-, di-, or tri-cyclic heteroaryl bridge (e.g., [3,4]furano, pyridino, thiopheno, piperidino, piperazino, pyrizidino, pyrrolidino) and combinations of such bridges.

The term "PyBOP" refers to benzotriazole-1-yl-oxy-tris-pyrrolidino-phosphonium hexafluorophosphate (Chemical Formula: C$_{18}$H$_{28}$F$_6$N$_6$OP$_2$; Molecular Weight: 520.39). The structure of PyBOP is

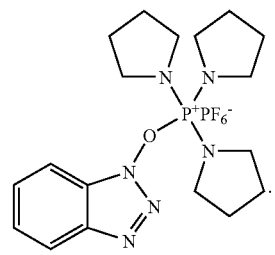

Some examples of prodrugs of the invention are provided in TABLE 1 and TABLE 1A. These examples merely serve to illustrate some embodiments of the invention and in no way limit the scope of the invention. When the stereochemistry is not specifically denoted, the stereochemistry of the compounds of TABLE 1, TABLE 1A and the compounds according to formula I includes all racemates, enantiomers and diastereomers of the compounds. Also included are the natural and non-natural amino acid moieties, such as L-amino acids and D-amino acids. In one embodiment, compounds of the invention comprise L-amino acid moieties. The invention also includes the various regioisomers and hydro-isomers of the prodrugs described herein, including the various regioisomers and hydro-isomers of the prodrugs of structural formulae (I) through (Id) and TABLE 1 and TABLE 1A. For example, when a bond is denoted as "———", it includes "◀▬▬" or "⁗⁗⁗⁗" (that is, both S and R configurations). Further, when a compound includes one or more chiral centers, each chiral center may assume any configuration independently of the others.

TABLE 1

| Cpd. No. | Structure |
|---|---|
| 1 | ![structure] |

TABLE 1-continued
| Cpd. No. | Structure |
|---|---|
| 2 | 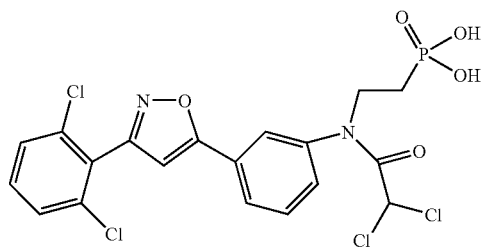 |
| 3 | 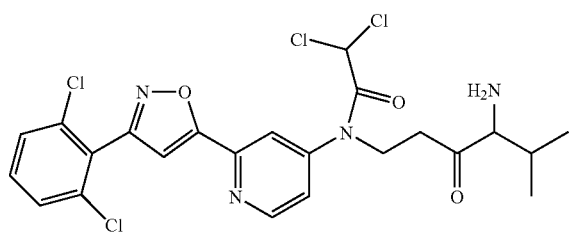 |
| 4 | 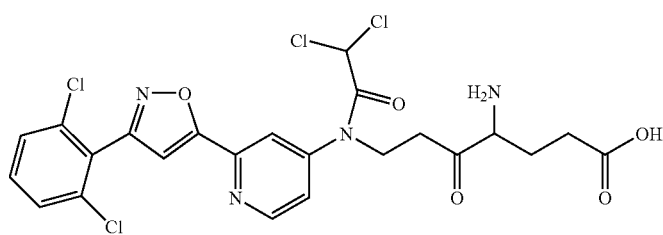 |
| 5 | 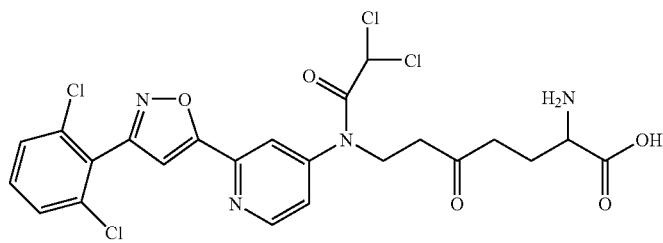 |
| 6 | 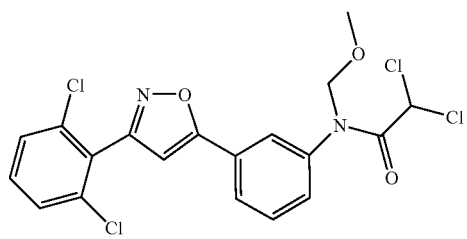 |
| 7 | 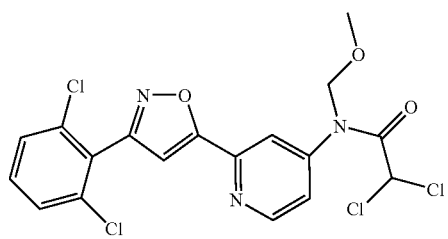 |

TABLE 1-continued
| Cpd. No. | Structure |
| --- | --- |
| 8 | 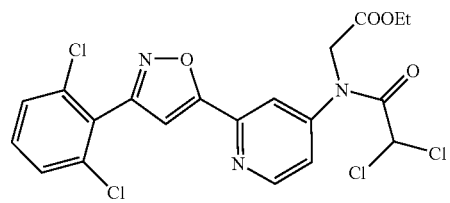 |
| 9 | 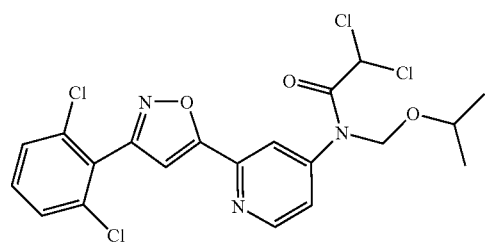 |
| 10 | 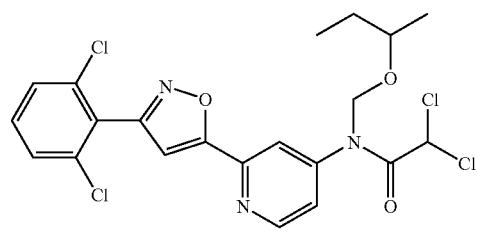 |
| 11 | 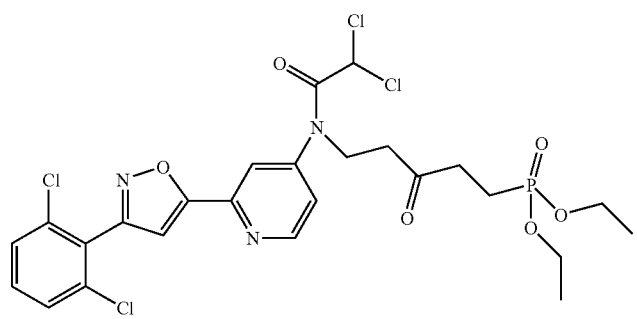 |
| 12 | 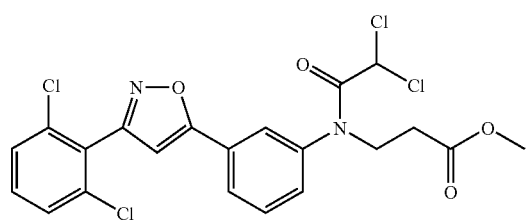 |
| 13 | 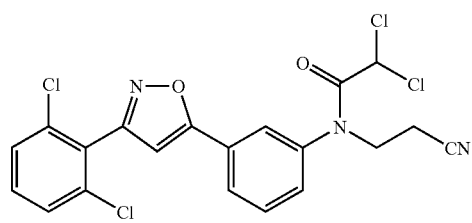 |

TABLE 1-continued
| Cpd. No. | Structure |
|---|---|
| 14 | 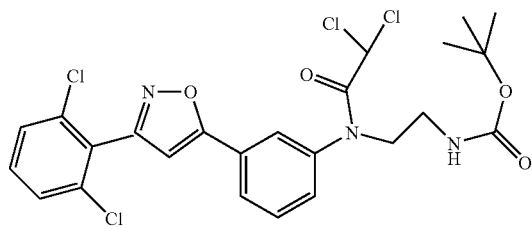 |
| 16 | 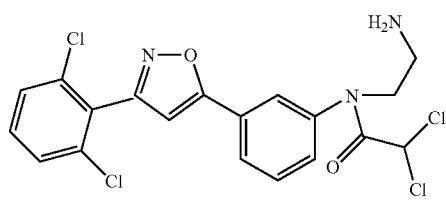 |
| 17 | 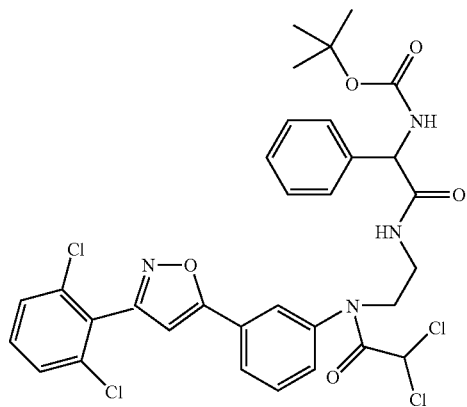 |
| 18 | 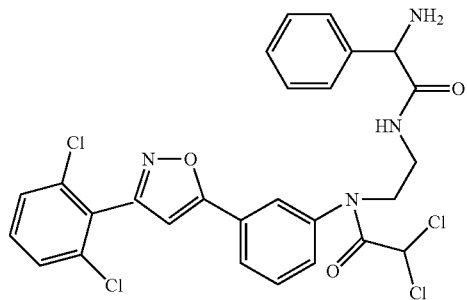 |
| 19 | 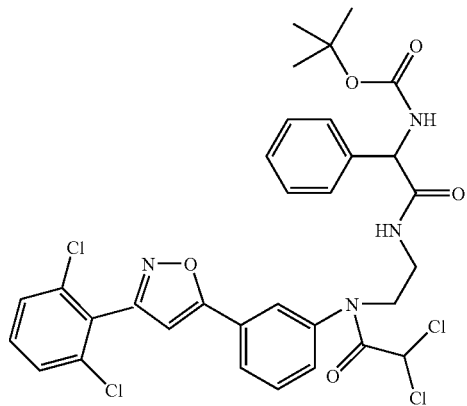 |

TABLE 1-continued
| Cpd. No. | Structure |
|---|---|
| 20 | 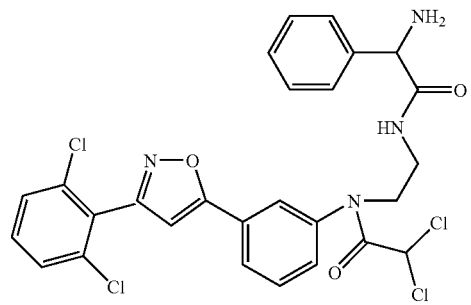 |
| 21 | 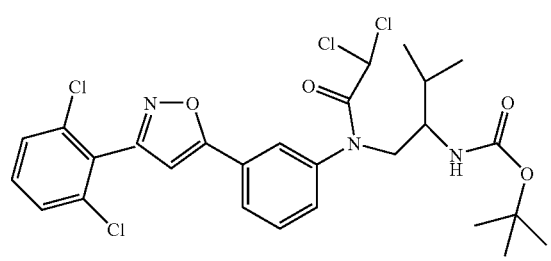 |
| 22 | 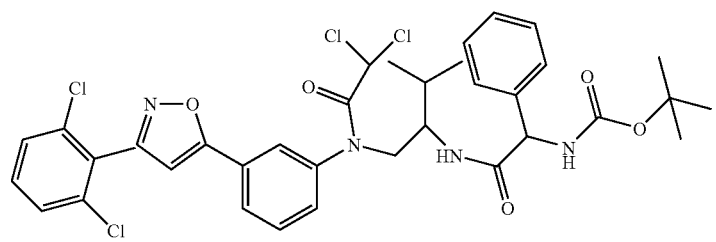 |
| 23 | 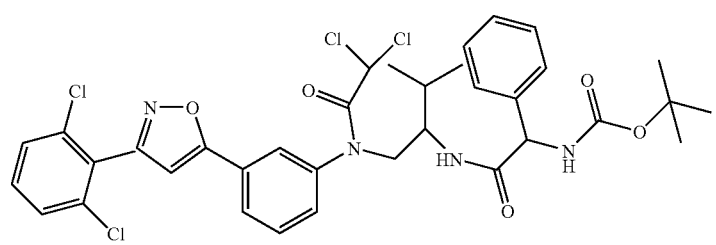 |
| 24 | 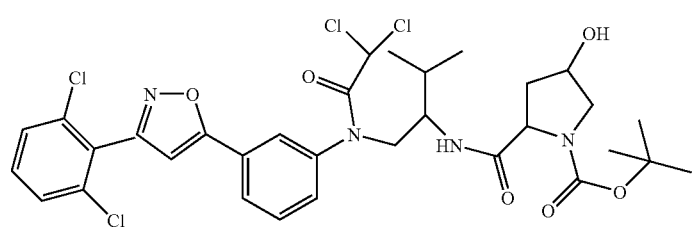 |
| 25 | 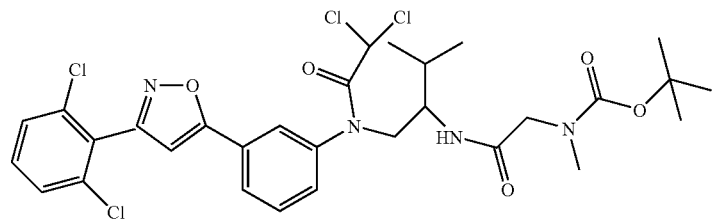 |

TABLE 1-continued

| Cpd. No. | Structure |
|---|---|
| 26 | 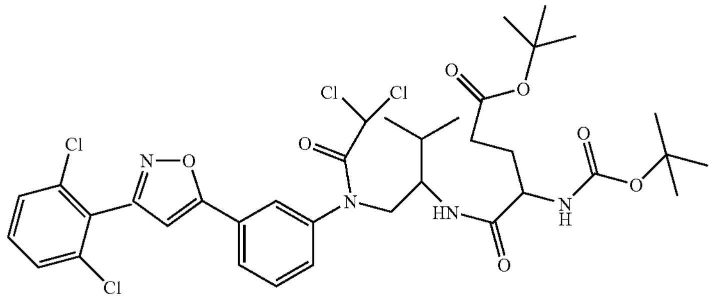 |
| 27 | 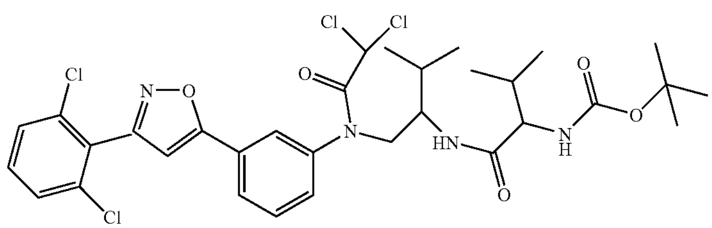 |
| 28 | 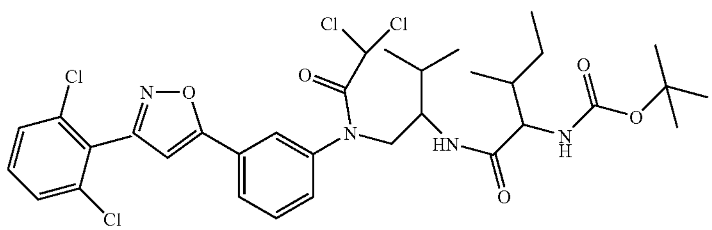 |
| 29 | 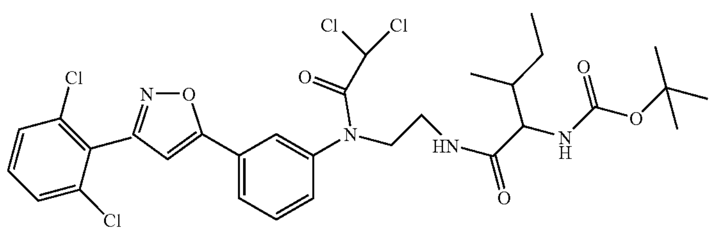 |
| 30 | 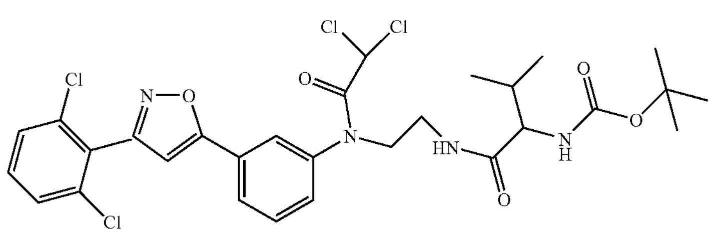 |
| 31 | 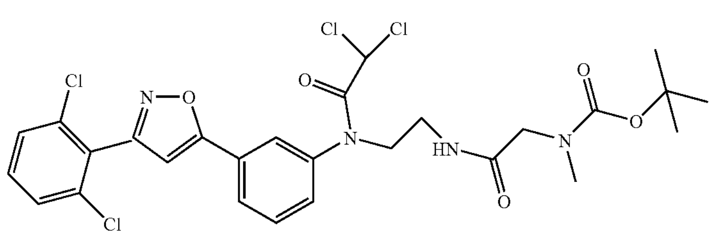 |

TABLE 1-continued
| Cpd. No. | Structure |
|---|---|
| 32 | 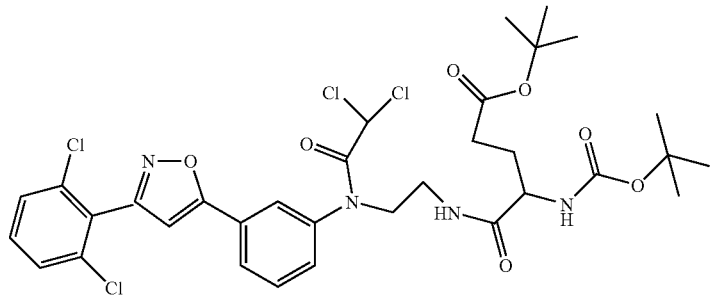 |
| 33 | 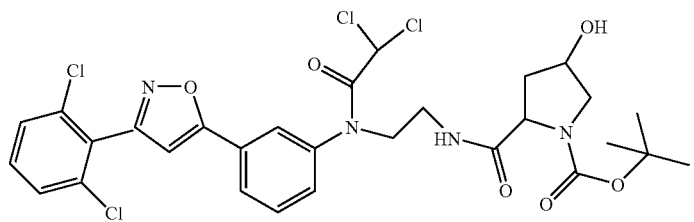 |
| 34 | 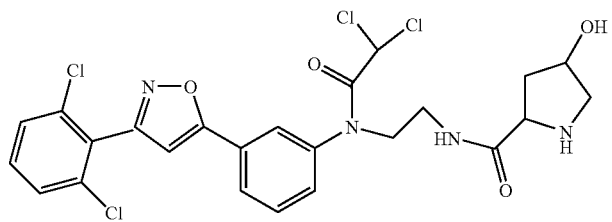 |
| 35 | 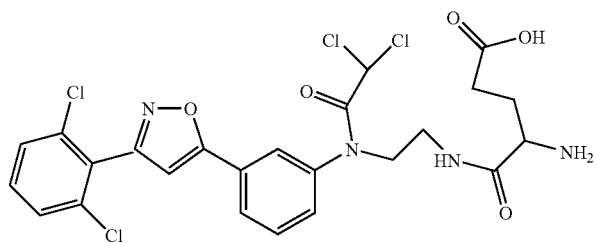 |
| 36 | 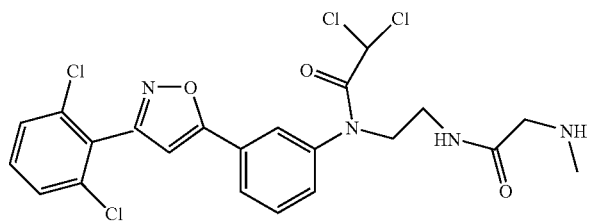 |
| 37 | 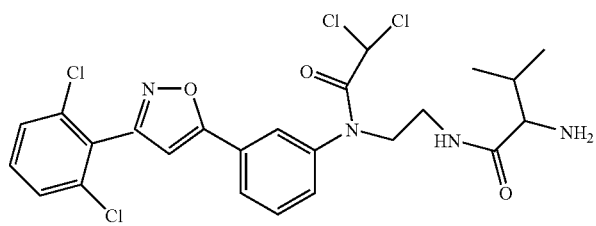 |

TABLE 1-continued
| Cpd. No. | Structure |
|---|---|
| 38 | 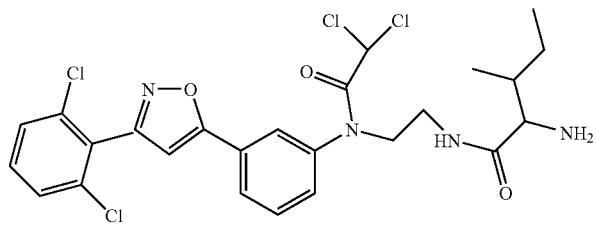 |
| 39 | 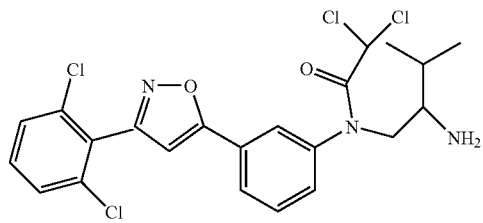 |
| 40 | 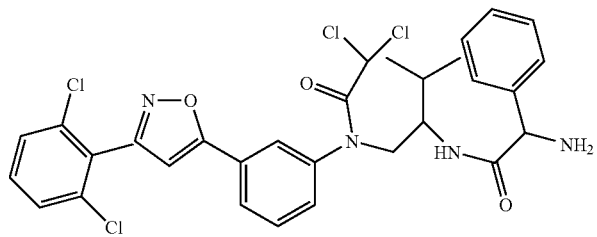 |
| 41 | 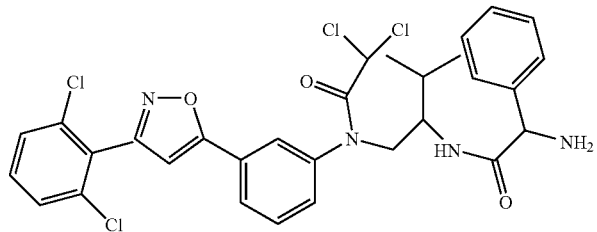 |
| 42 | 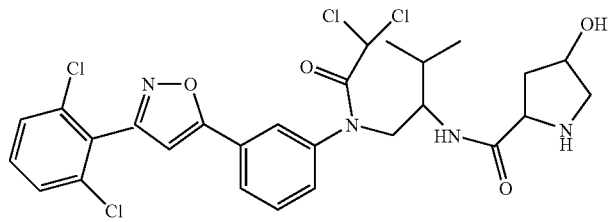 |
| 43 | 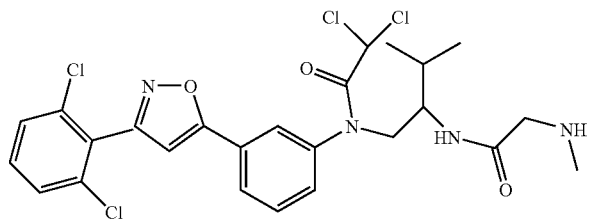 |

TABLE 1-continued

| Cpd. No. | Structure |
|---|---|
| 44 | 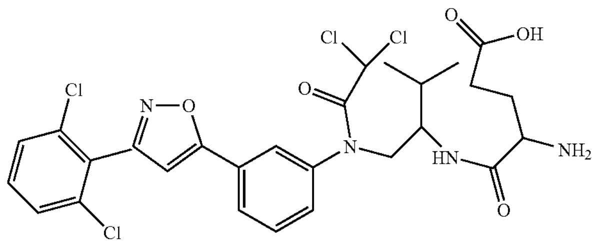 |
| 45 | 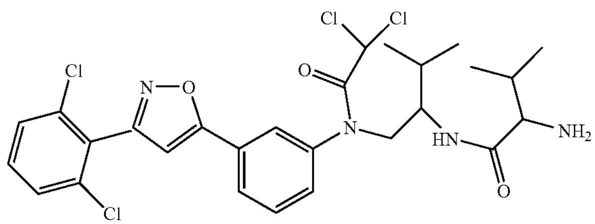 |
| 46 | 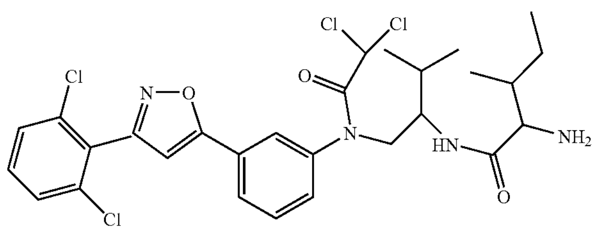 |
| 47 | 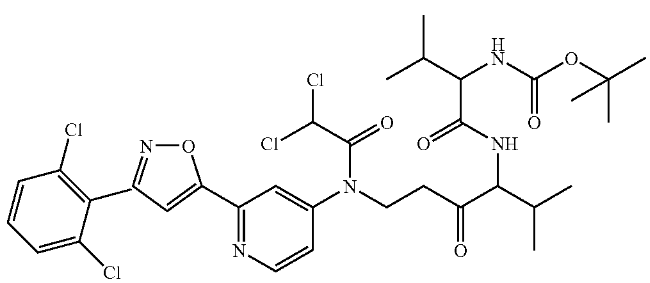 |
| 48 | 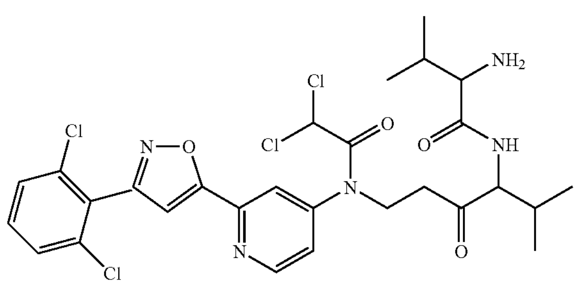 |
| 49 | 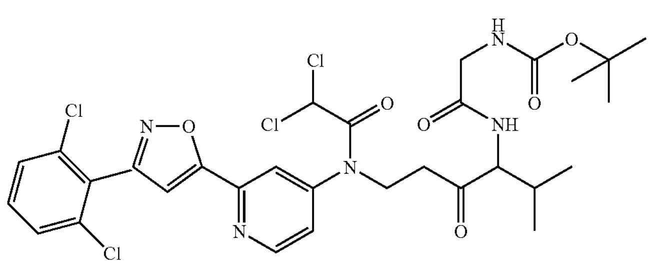 |

TABLE 1-continued
| Cpd. No. | Structure |
|---|---|
| 50 | 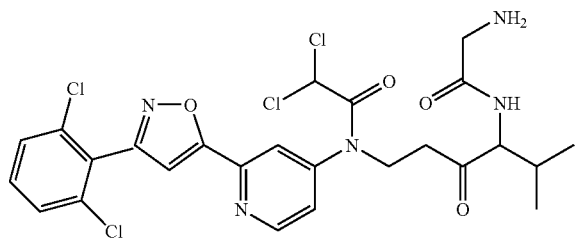 |
| 51 | 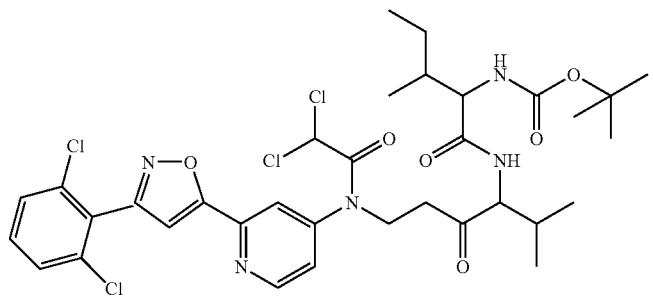 |
| 52 | 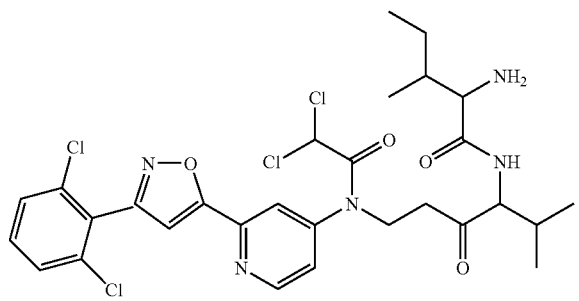 |
| 53 | 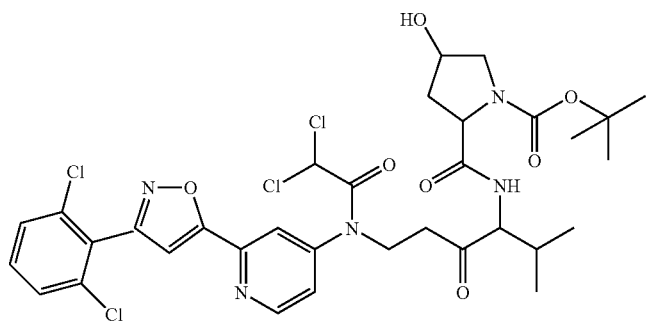 |
| 54 | 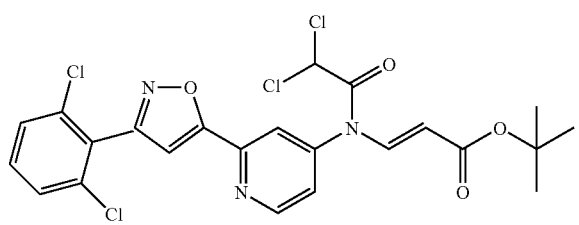 |

TABLE 1-continued
| Cpd. No. | Structure |
|---|---|
| 55 | 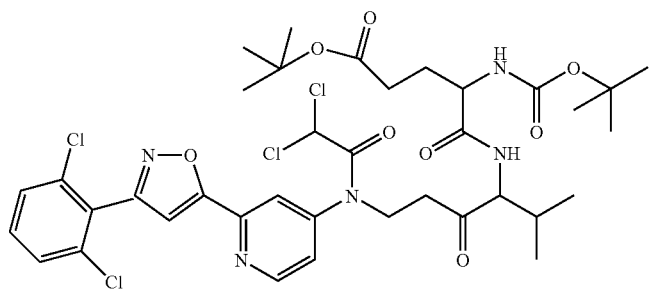 |
| 56 | 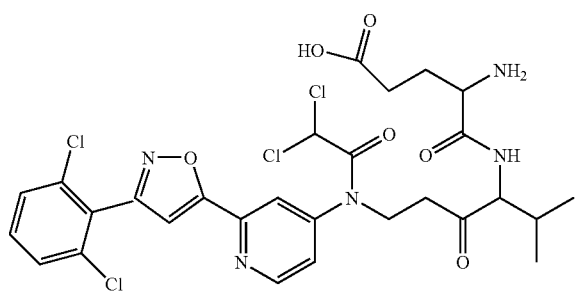 |
| 57 | 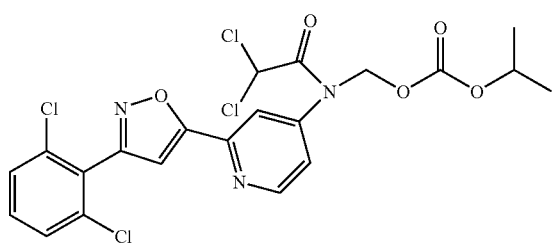 |
| 58 | 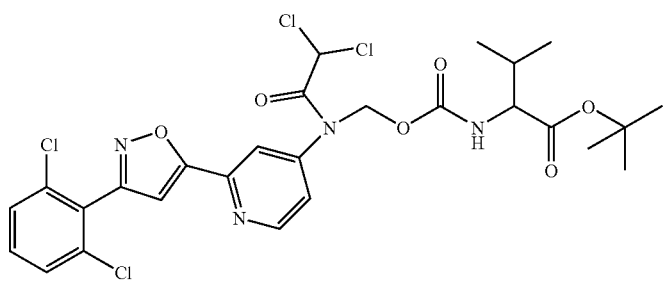 |
| 59 | 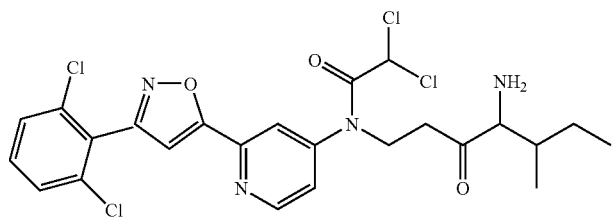 |
| 60 | 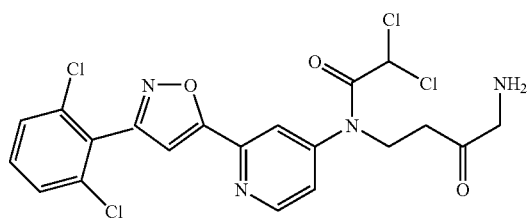 |

TABLE 1-continued

| Cpd. No. | Structure |
|---|---|
| 61 | (structure) |
| 62 | (structure) |
| 63 | (structure) |
| 67 | (structure) |
| 68 | (structure) |

TABLE 1-continued
| Cpd. No. | Structure |
|---|---|
| 69 | 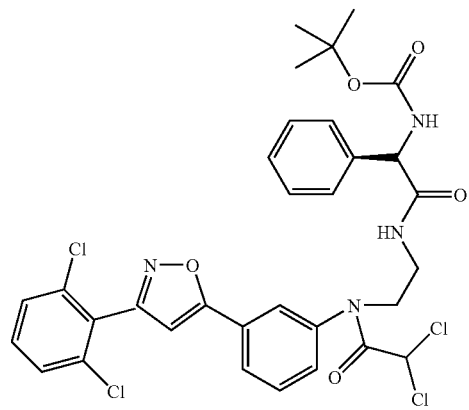 |
| 70 | 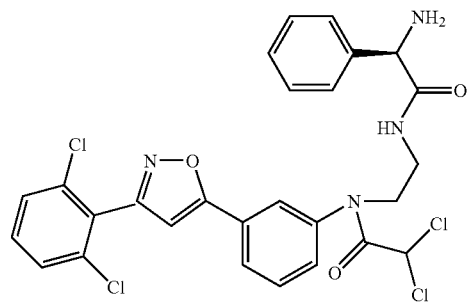 |
| 71 | 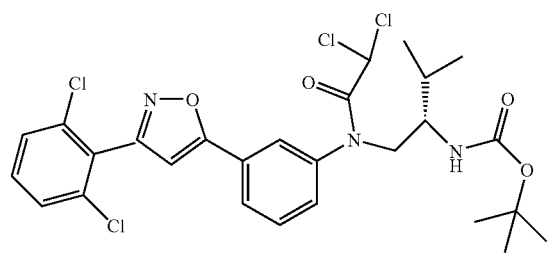 |
| 72 | 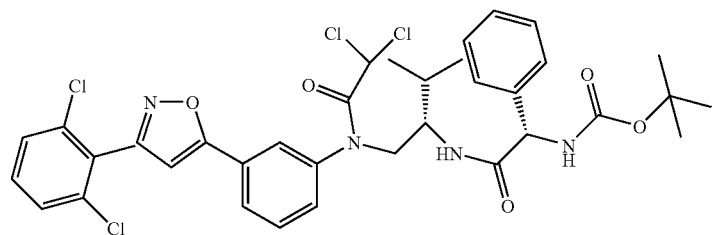 |
| 73 | 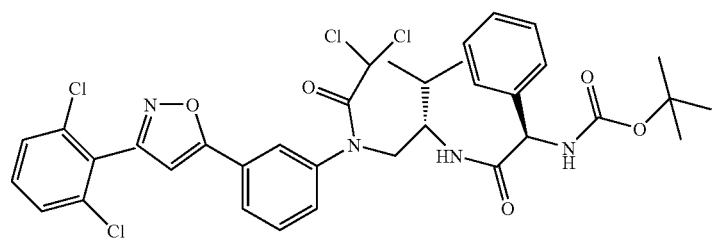 |

TABLE 1-continued
| Cpd. No. | Structure |
|---|---|
| 74 | 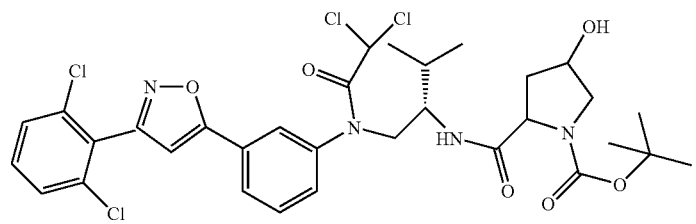 |
| 75 | 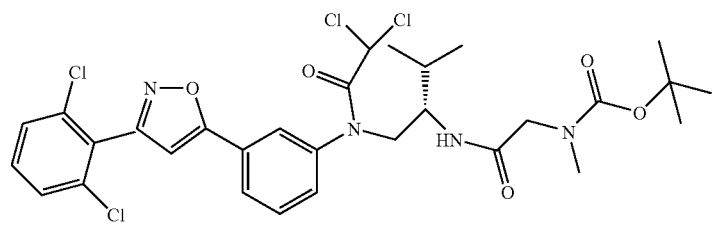 |
| 76 | 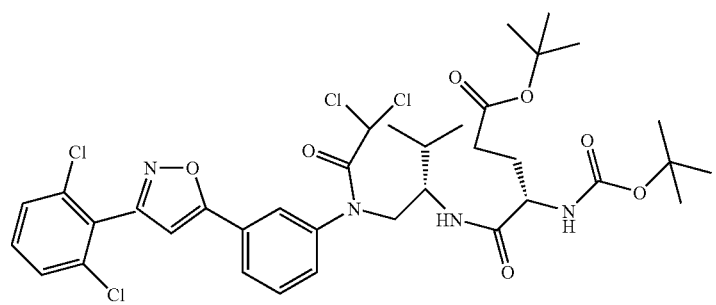 |
| 77 | 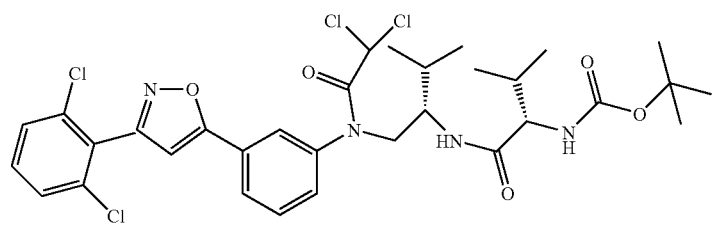 |
| 78 | 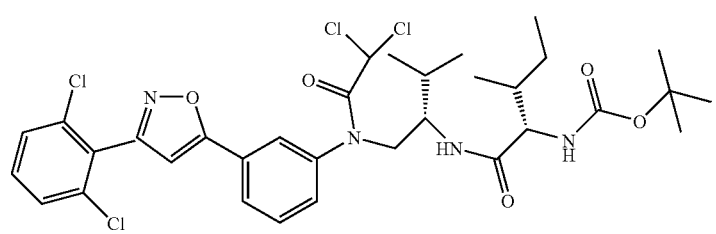 |
| 79 | 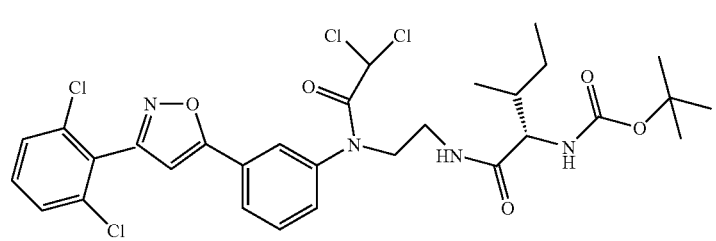 |

TABLE 1-continued

| Cpd. No. | Structure |
| --- | --- |
| 80 | (structure) |
| 82 | (structure) |
| 83 | (structure) |
| 84 | (structure) |
| 85 | (structure) |
| 86 | (structure) |

TABLE 1-continued
| Cpd. No. | Structure |
|---|---|
| 87 | 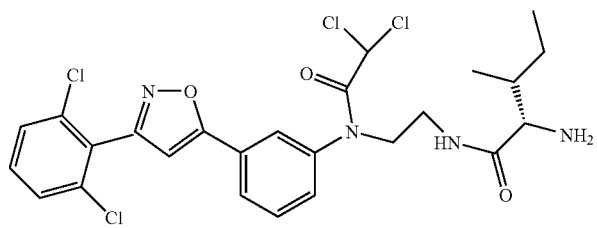 |
| 88 | 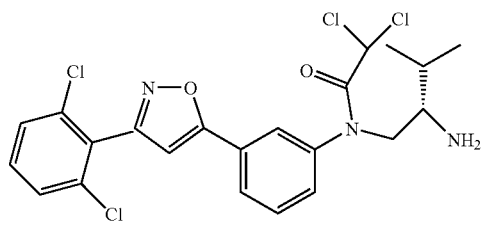 |
| 89 | 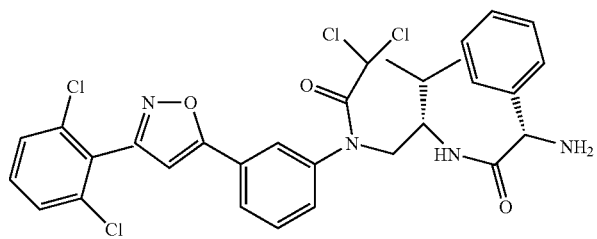 |
| 90 | 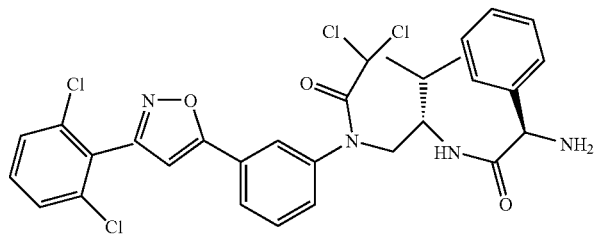 |
| 91 | 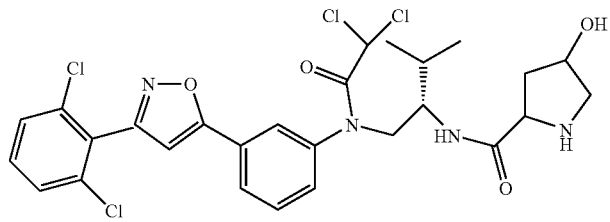 |
| 92 | 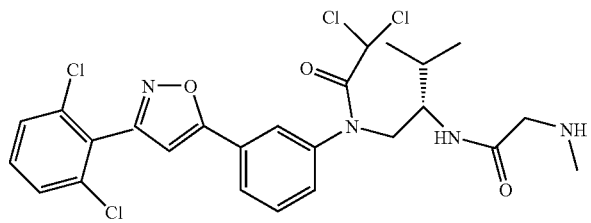 |

TABLE 1-continued
| Cpd. No. | Structure |
|---|---|
| 93 | 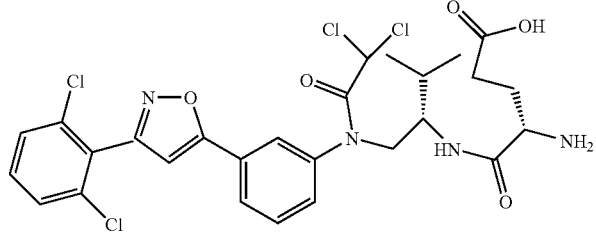 |
| 94 | 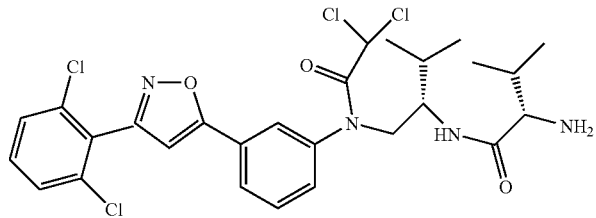 |
| 95 | 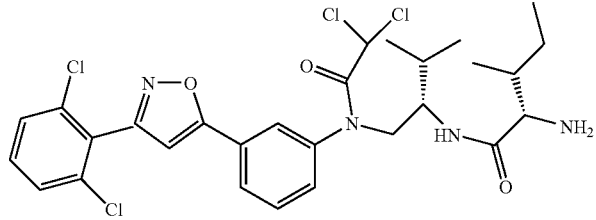 |
| 96 | 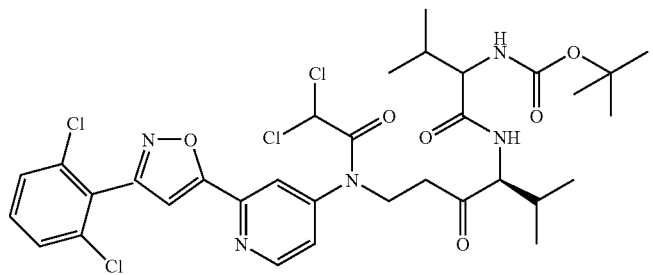 |
| 97 | 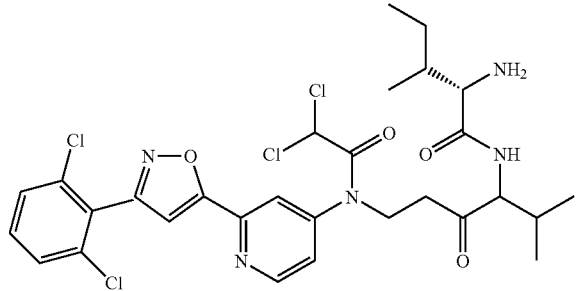 |
| 98 | 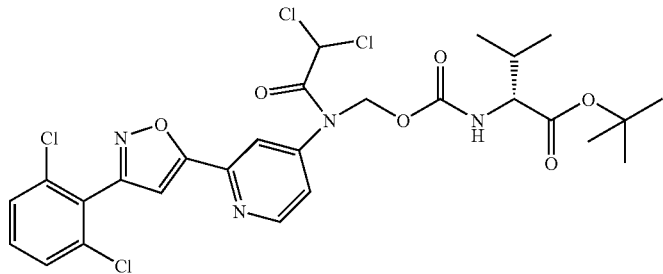 |

TABLE 1-continued

| Cpd. No. | Structure |
|---|---|
| 99 | 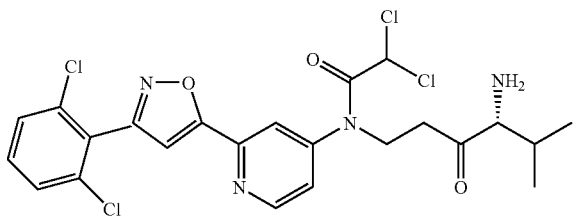 |

Compounds of the invention are drawn using ChemDraw Ultra 8.0 chemical drawing program from CambridgeSoft Corporation of Cambridge Mass. and in some instances named according to application of CambridgeSoft proprietary naming software therein. Compounds of the invention may also be named herein according to systematic application of the nomenclature rules agreed upon by the International Union of Pure and Applied Chemistry (IUPAC), International Union of Biochemistry and Molecular Biology (IUBMB), and the Chemical Abstracts Service (CAS).

Uses and Administration

Owing to their ability to inhibit HCV replication, the metabolically active agents of the prodrugs of the invention and/or compositions thereof can be used in a variety of contexts. For example, the prodrugs of the invention can be used as controls in in vitro assays to identify additional more or less potent anti HCV prodrugs. As another example, the prodrugs of the invention and/or compositions thereof can be used as preservatives or disinfectants in clinical settings to prevent medical instruments and supplies from becoming infected with HCV virus. When used in this context, the prodrugs of the invention and/or composition thereof may be applied to the instrument to be disinfected at a concentration that is a multiple, for example 1×, 2×, 3×, 4×, 5× or even higher, of the measured $IC_{50}$ for the metabolically active agent of the prodrug.

In a specific embodiment, the prodrugs and/or compositions can be used to "disinfect" organs for transplantation. For example, a liver or portion thereof being prepared for transplantation can be perfused with a solution comprising an inhibitory prodrug of the invention prior to implanting the organ into the recipient. This method has proven successful with lamuvidine (3TC, Epivir®, Epivir-HB®) for reducing the incidence of hepatitis B virus (HBV) infection following liver transplant surgery/therapy. Quite interestingly, it has been found that such perfusion therapy not only protects a liver recipient free of HBV infection (HBV−) from contracting HBV from a liver received from an HBV+ donor, but it also protects a liver from an HBV− donor transplanted into an HBV+ recipient from attack by HBV. The prodrugs of the invention may be used in a similar manner prior to organ or liver transplantation.

The prodrugs of the invention and/or compositions thereof find particular use in the treatment and/or prevention of HCV infections in animals and humans. When used in this context, the prodrugs may be administered per se, but are typically formulated and administered in the form of a pharmaceutical composition. The exact composition will depend upon, among other things, the method of administration and will apparent to those of skill in the art. A wide variety of suitable pharmaceutical compositions are described, for example, in Remington's Pharmaceutical Sciences, 20$^{th}$ ed., 2001).

Formulations suitable for oral administration can consist of (a) liquid solutions, such as an effective amount of the prodrugs suspended in diluents, such as water, saline or PEG 400; (b) capsules, sachets or tablets, each containing a predetermined amount of the active ingredient, as liquids, solids, granules or gelatin; (c) suspensions in an appropriate liquid; (d) suitable emulsions; and (e) microcapsules. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The prodrug of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the prodrug of choice with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, subcutaneous administration and intravenous administration are the preferred methods of administration. A specific example of a suitable solution formulation may comprise from about 0.5-100 mg/ml prodrug and about 1000 mg/ml propylene glycol in water. Another specific example of a suitable solution formulation may comprise from about 0.5-100 mg/ml prodrug and from about 800-1000 mg/ml polyethylene glycol 400 (PEG 400) in water.

A specific example of a suitable suspension formulation may include from about 0.5-30 mg/ml prodrug and one or more excipients selected from the group consisting of: about 200 mg/ml ethanol, about 1000 mg/ml vegetable oil (e.g., corn oil), about 600-1000 mg/ml fruit juice (e.g., grape juice), about 400-800 mg/ml milk, about 0.1 mg/ml carboxymethylcellulose (or microcrystalline cellulose), about 0.5 mg/ml benzyl alcohol (or a combination of benzyl alcohol and benzalkonium chloride) and about 40-50 mM buffer, pH 7 (e.g., phosphate buffer, acetate buffer or citrate buffer or, alternatively 5% dextrose may be used in place of the buffer) in water.

A specific example of a suitable liposome suspension formulation may comprise from about 0.5-30 mg/ml prodrug, about 100-200 mg/ml lecithin (or other phospholipid or mixture of phospholipids) and optionally about 5 mg/ml cholesterol in water. For subcutaneous administration of a prodrug, a liposome suspension formulation including 5 mg/ml prodrug in water with 100 mg/ml lecithin and 5 mg/ml prodrug in water with 100 mg/ml lecithin and 5 mg/ml cholesterol provides good results. This formulation may be used for other prodrugs of the invention.

The formulations of prodrugs can be presented in unit-dose or multi-dose sealed containers, such as ampoules and vials. Injection solutions and suspensions can be prepared from sterile powders, granules, and tablets of the kind previously described.

The pharmaceutical preparation is preferably in unit dosage form. In such form the preparation is subdivided into unit doses containing appropriate quantities of the prodrug. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents, discussed in more detail, below.

In therapeutic use for the treatment of HCV infection, the prodrugs utilized in the pharmaceutical method of the invention are administered to patients diagnosed with HCV infection at dosage levels suitable to achieve therapeutic benefit. By therapeutic benefit is meant that the administration of prodrug leads to a beneficial effect in the patient over time. For example, therapeutic benefit is achieved when the HCV titer or load in the patient is either reduced or stops increasing. Therapeutic benefit is also achieved if the administration of prodrug slows or halts altogether the onset of the organ damage that or other adverse symptoms typically accompany HCV infections, regardless of the HCV titer or load in the patient.

The prodrugs of the invention and/or compositions thereof may also be administered prophylactically in patients who are at risk of developing HCV infection, or who have been exposed to HCV, to prevent the development of HCV infection. For example, the prodrugs of the invention and/or compositions thereof may be administered to hospital workers accidentally stuck with needles while working with HCV patients to lower the risk of, or avoid altogether, developing an HCV infection.

Initial dosages suitable for administration to humans may be determined from in vitro assays or animal models. For example, an initial dosage may be formulated to achieve a serum concentration that includes the $IC_{50}$ of the particular metabolically active agent of the prodrug being administered, as measured in an in vitro assay. Alternatively, an initial dosage for humans may be based upon dosages found to be effective in animal models of HCV infection. Suitable model systems are described, for example, in Muchmore, 2001, Immunol. Rev. 183:86-93 and Lanford & Bigger, 2002, Virology, 293:1-9, and the referenced cited therein. As one example, the initial dosage may be in the range of about 0.01 mg/kg/day to about 200 mg/kg/day, or about 0.1 mg/kg/day to about 100 mg/kg/day, or about 1 mg/kg/day to about 50 mg/kg/day, or about 10 mg/kg/day to about 50 mg/kg/day, can also be used. The dosages, however, may be varied depending upon the requirements of the patient, the severity of the condition being treated, and the prodrug being employed. The size of the dose also will be determined by the existence, nature, and extent of any adverse side-effects that accompany the administration of a particular prodrug in a particular patient. Determination of the proper dosage for a particular situation is within the skill of the practitioner. Generally, treatment is initiated with smaller dosages which are less than the optimum dose of the prodrug. Thereafter, the dosage is increased by small increments until the optimum effect under circumstances is reached. For convenience, the total daily dosage may be divided and administered in portions during the day, if desired.

Combination Therapy

In certain embodiments of the present invention, the prodrugs of the invention and/or compositions thereof can be used in combination therapy with at least one other therapeutic agent. A prodrug of the invention and/or composition thereof and the therapeutic agent can act additively or, more preferably, synergistically. The prodrug of the invention and/or a composition thereof may be administered concurrently with the administration of the other therapeutic agent(s), or it may be administered prior to or subsequent to administration of the other therapeutic agent(s).

In one embodiment, the prodrugs of the invention and/or compositions thereof are used in combination therapy with other antiviral agents or other therapies known to be effective in the treatment or prevention of HCV. As a specific example, the prodrugs of the invention and/or compositions thereof may be used in combination with known antivirals, such as ribavirin (see, e.g., U.S. Pat. No. 4,530,901). As another specific example, the prodrugs of the invention and/or compositions thereof may also be administered in combination with one or more of the compounds described in any of the following: U.S. Pat. Nos. 6,143,715; 6,323,180; 6,329,379; 6,329,417; 6,410,531; 6,420,380; and 6,448,281.

Yet another specific example, the prodrugs of the invention and/or compositions thereof may be used in combination with interferons such as $\overline{\alpha}$-interferon $\overline{\beta}$-interferon and/or γ-interferon. The interferons may be unmodified, or may be modified with moieties such as polyethylene glycol (pegylated interferons). Many suitable unpegylated and pegylated interferons are available commercially, and include, by way of example and not limitation, recombinant interferon alpha-2b such as Intron-A interferon available from Schering Corporation, Kenilworth, N.J., recombinant interferon alpha-2a such as Roferon interferon available from Hoffmann-La Roche, Nutley, N.J., recombinant interferon alpha-2C such as Berofor alpha 2 interferon available from Boehringer Ingelheim Pharmaceutical, Inc., Ridgefield, Conn., interferon alpha-n1, a purified blend of natural alpha interferons such as Sumiferon available from Sumitomo, Japan or as Wellferon interferon alpha-n1 (INS) available from the Glaxo- Wellcome Ltd., London, Great Britain, or a consensus alpha interferon such as those described in U.S. Pat. Nos. 4,897,471 and 4,695,623 (especially Examples 7, 8 or 9 thereof) and the specific product available from Amgen, Inc., Newbury Park, Calif., or interferon alpha-n3 a mixture of natural alpha interferons made by Interferon Sciences and available from the Purdue Frederick Co., Norwalk, Conn., under the Alferon Tradename, pegylated interferon-2b available from Schering Corporation, Kenilworth, N.J. under the tradename PEG-Intron A and pegylated interferon-2a available from Hoffmann-LaRoche, Nutley, N.J. under the tradename Pegasys.

As yet another specific example, the prodrugs of the invention and/or compositions thereof may be administered in combination with both ribovirin and an interferon.

Methods of Synthesis

The prodrugs of the invention may be obtained via synthetic methods illustrated in Scheme 1. In general, compounds of formula (I) are made via formation of the B ring system via reaction of appropriately functionalized A and C ring starting materials. For example, Scheme 1 depicts combination of a chloro-oxime functionalized benzene (for example), 101, with an alkynyl functionalized ring C benzene (for example), 103, to form compound 105. In this example, the A-B—C ring system is formed via [3+2] cycloaddition via an in situ formed nitrile oxide intermediate 104. The invention is not however limited in this way. In Scheme 1, $R^{20}$ is as defined above, and "R" refers generically to —H, $R^{11}$, haloacetyl groups according to formula (I), or precursors or otherwise protected forms of $R^{11}$ and such halo acetyl groups. When the groups "R" are other than hydrogen for example, they can each independently be attached to the ring nitrogen either before or after formation of the B ring. As mentioned above, in one example, intermediates of formula (III), A-B—C—$NH_2$, are formed followed by functionalization to compounds of formula (I). In other examples, $R^{11}$ is attached to the ring C nitrogen, followed by ring B formation, then the haloacetyl group is added thereafter. Also as mentioned herein, ring B need not be an isoxazole nor formed by [3+2] cycloaddition. One of ordinary skill in the art following this description, and in conjunction with the following specific examples, would appreciate that many combinations are possible for synthesizing compounds according to formula (I).

In Scheme 1, substituents $R^{20}$ may include reactive functional groups that require protection during synthesis. Selection of suitable protecting groups will depend on the identity of the functional group and the synthesis method employed, and will be apparent to those of skill in the art. Guidance for selecting suitable protecting groups can be found in Greene & Wuts, supra, and the various other references cited therein.

Scheme 1
Example of [3 + 2] Cycloaddition

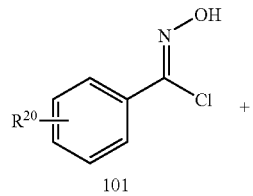

101

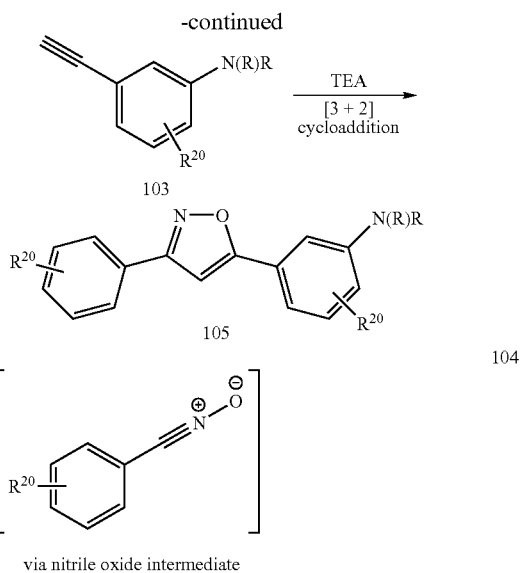

via nitrile oxide intermediate

Starting materials useful for preparing prodrugs of the invention and intermediates thereof are commercially available or can be prepared by well-known synthetic methods (see, e.g., Harrison et al., "Compendium of Synthetic Organic Methods", Vols. 1-8 (John Wiley and Sons, 1971-1996); "Beilstein Handbook of Organic Chemistry," Beilstein Institute of Organic Chemistry, Frankfurt, Germany; Feiser et al., "Reagents for Organic Synthesis," Volumes 1-21, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," 3d Edition, John Wiley & Sons, 1995). Other methods for synthesis of the compounds described herein and/or starting materials are either described in the art or will be readily apparent to the skilled artisan. Accordingly, the synthetic methods and strategy presented herein are illustrative rather than comprehensive.

It should be understood that the following general methods are meant to be illustrative. For example, the synthetic routes described focus on isoxazole "B" rings. However, heterocyclic rings in place of an isoxazole "B" ring as described throughout the specification can be employed by the skilled artisan. Additionally, substituents utilized in the Schemes correspond to those described throughout the specification. Manipulation and choice of substituents are within the knowledge of a skilled artisan.

Further guidance for carrying out 1,3-dipolar cycloaddition reactions, also named 1,3-dipolar additions, [3+2] cyclizations or [3+2] cycloadditions, can be found in "Cycloaddition Reactions in Organic Synthesis", (Kobayashi, S. and Jorgensen, K. A., Editors), 2002, Wiley-VCH Publishers, pp. 1-332 pages (specifically, Chapters 6 and 7 on [3+2] cycloadditions and 1,3-dipolar additions, pp. 211-248 and 249-300); "1,3-Dipolar Cycloaddition", *Chemistry of Heterocyclic Compounds*, Vol. 59, (Padwa, A. and Pearson, W., Editors), 2002, John Wiley, New York, pp. 1-940; "Nitrile Oxides, Nitrones, Nitronates in Organic Synthesis: Novel Strategies in Synthesis", Torssel, K. B. G., 1988, VCH Publishers, New York, pp. 1-332; Barnes & Spriggs, 1945, *J. Am.*

Chem Soc. 67:134; and Anjaneyulu et al., 1995, *Indian J. Chem., Sect.* 5 34(11):933-938).

Further guidance for synthesizing isoxazoles may be found in M. Sutharchanadevi, R. Murugan in *Comprehensive Heterocyclic Chemistry II*, A. R. Katritzky, C. W. Rees, E. F. V. Scriven, Eds.; Pergamon Press, Oxford, Vol. 3, p. 221; R. Grünager, P, Vita-Finzi in *Heterocyclic Compounds, Vol 49, Isoxazoles, Part one*, John Wiley and Sons, New York, 1991; K. B. G. Torssell, *Nitrile Oxides, Nitrones, and Nitronates in Organic Synthesis*, VCH Publishers, New York, 1988; Y-Y. Ku, T. Grieme, P. Sharma, Y.-M. Pu, P. Raje, H. Morton, S. King *Organic Letters*, 2001, 3, 4185; V. G. Desai, S. G. Tilve *Synth. Comm.*, 1999, 29, 3017; X. Wei, J. Fang, Y. Hu, H. Hu *Synthesis*, 1992, 1205; C. Kashima, N. Yoshihara, S. Shirai *Heterocycles*, 1981, 16, 145; A. S. R. Anjaneyulu, G. S. Rani, K. G. Annapurna, U. V. Mallavadhani, Y. L. N. Murthy *Indian J. Chem. Sect B*, 1995, 34, 933; R. P. Barnes, A. S. Spriggs, *J. Am Chem. Soc.*, 1945, 67, 134; A. Alberola, L. Calvo, A. G. Ortega, M. L. Sábada, M. C. Sañudo, S. G. Granda, E. G. Rodriguez *Heterocycles*, 1999, 51, 2675; X. Wang, J. Tan, K. Grozinger *Tetrahedron Lett.* 2000, 41, 4713; A. R. Katritzky, M. Wang, S. Zhang, M. V. Voronkov *J. Org. Chem.*, 2001, 66, 6787; and J. Bohrisch, M. Pätzel, C. Mügge, J. Liebscher *Synthesis*, 1991, 1153. Further guidance for synthesizing pyrazoles may be found in J. Elguero in *Comprehensive Heterocyclic Chemistry II*, A. R. Katritzky, C. W. Reees, E. F. V. Scriven., Eds.; Pergamon Press, Oxford, 1996; Vol. 3, p. 1.

EXAMPLES

The following examples are provided by way of illustration only and not by way of limitation. Those of skill in the art will readily recognize a variety of noncritical parameters that could be changed or modified to yield essentially similar results.

The prodrugs of TABLE 1 were synthesized according to the methods described below or illustrated in Schemes 1 and 8. Melting points were obtained using an Electrothermal IA9100 series digital melting point apparatus. All Melting points are uncorrected. Elemental analysis was performed by Desert Analytics, Tuscon, Ariz. NMR spectra were obtained on a 300 MHz Varian Mercury system. Microwave reactions were carried out in the Personal Chemistry, SmithCreator microwave. LC-MS was performed on a Waters Micromass ZQ instrument with electrospray ionization. The HPLC component was a Waters Model 2690 Separation module coupled to a Waters Model 996 photodiode array detector at 254 nm wavelength. The specific LC-MS method used to analyze particular prodrugs, indicated for each prodrug in parentheses, are provided below:

Synthesis of 2-(2,2-Dichloro-N-(3-(3-(2,6-dichlorophenyl)isoxazol-5-yl)phenyl)acetamido)ethylphosphonic Acid (See Scheme 2) (Cpd. No. 2)

Synthesis of Diethyl 2-(3-Ethynylphenylamino)ethylphosphonate

3-Ethynyl aniline (2.36 g, 22.1 mmol), diethyl 2-bromoethylphosphonate (5.41 g, 22.1 mmol) and potassium carbonate (3.1 gm, 22.1 mmol) were heated at 90° C. in anhydrous acetonitrile (40 mL) for 26 h. The solvent was removed under reduced pressure and the residue was partitioned between ethyl acetate and water. The organic layer was separated, washed with brine, dried over anhydrous sodium sulfate, filtered and concentrated under reduced pressure. The resulting residue was purified by flash column chromatography on silica gel, eluting with 1:1 ethyl acetate:hexanes followed by 97:3 methylene chloride:methanol to provide diethyl 2-(3-ethynylphenylamino)ethylphosphonate (450 mg) as a yellow oil. $^1$H NMR (CDCl$_3$) δ 7.15 (t, 1H), 6.83 (d, 1H), 6.70 (br s, 1H), 6.60 (m, 1H), 4.10 (m, 4H), 3.41 (m, 2H), 3.00 (s, 1H), 2.10 (m, 2H), 1.35 ppm (m, 6H). MW=281 confirmed by LC-MS, t$_r$=11.65 min (Method Y) MH$^+$=282.

Synthesis of Diethyl 2-(3-(3-(2,6-Dichlorophenyl) isoxazol-5-yl)phenylamino)ethylphosphonate 2,6-Dichloro-N-hydroxybenzimidoyl chloride (370 mg, 1.6 mmol) and diethyl 2-(3-ethynylphenylamino)ethylphosphonate (450 mg, 1.6 mmol) were dissolved in anhydrous tetrahydrofuran (40 mL) and triethylamine (0.30 mL, 1.6 mmol). The mixture was then heated at reflux for 5 h. The reaction was cooled to room temperature and the solvent was removed under reduced pressure. The residue was dissolved in ethyl acetate and washed successively with water and brine. The ethyl acetate solution was dried over anhydrous sodium sulfate, filtered and concentrated under reduced pressure. The resulting solid was purified by flash column chromatography on silica gel, eluting with 98:2 methylene chloride:methanol to give diethyl 2-(3-(3-(2,6-dichlorophenyl) isoxazol-5-yl)phenylamino)ethylphosphonate (670 mg) as a pale yellow oil. $^1$H NMR (CDCl$_3$): 7.30 (m, 2H), 7.21 (m, 1H), 7.15 (m, 1H), 7.05 (m, 1H), 7.00 (m, 1H), 6.59 (m, 1H), 6.48 (s, 1H), 4.03 (m, 4H), 3.40 (m, 2H), 2.00 (m, 2H), 1.24 ppm (m, 6H). MW=469 confirmed by LC-MS, t$_r$=14.80 min (Method Y) MH$^+$=467-472.

Synthesis of Diethyl 2-(2,2-Dichloro-N-(3-(3-(2,6-dichlorophenyl)isoxazol-5-yl)phenyl)acetamido) ethylphosphonate (Cpd. No. 1)

Diethyl 2-(3-(3-(2,6-dichlorophenyl)isoxazol-5-yl)phenylamino)ethylphosphonate (660 mg, 1.4 mmol) was dissolved in anhydrous methylene chloride (10 mL) with triethylamine (0.28 mL, 1.7 mmol). The mixture was cooled in an ice-bath under nitrogen, then a solution of dichloroacetyl chloride (161 μL, 1.7 mmol) in anhydrous dichloromethane (0.5 mL) was added dropwise. After the addition was completed the ice-bath was removed and the mixture was stirred at room temperature overnight. The reaction mixture was diluted with methylene chloride and then washed successively with water, 10% hydrochloric acid and saturated sodium bicarbonate solution. The organic solution was dried over anhydrous sodium sulfate, filtered and concentrated under reduced pressure. The resulting residue was purified by flash column chromatography on silica gel, eluting with 1:1 ethyl acetate:hexanes followed by 98:2 methylene chloride:methanol to give diethyl 2-(2,2-dichloro-N-(3-(3-(2,6-dichlorophenyl)isoxazol-5-yl)phenyl)acetamido)ethylphosphonate (Cpd. No. 1) as a white solid. $^1$H NMR (CDCl$_3$): 7.94 (m, 1H), 7.79 (m, 1H), 7.64 (m, 1H), 7.46-7.40 (m, 2H), 7.43-7.36 (m, 2H), 6.72 (s, 1H), 5.85 (s, 1H), 4.08 (m, 6H), 2.13 (m, 2H), 1.33 ppm (m, 6H). MW=580 confirmed by LC-MS, t$_r$=11.55 min (Method A) MH$^+$=578-582.

Synthesis of 2-(2,2-Dichloro-N-(3-(3-(2,6-dichlorophenyl)isoxazol-5-yl)phenyl)acetamido)ethylphosphonic Acid (Cpd. No. 2)

Diethyl 2-(2,2-dichloro-N-(3-(3-(2,6-dichlorophenyl) isoxazol-5-yl)phenyl)acetamido)ethylphosphonate (Cpd. No. 1, 50 mg, 0.09 mmol) was dissolved in anhydrous methylene chloride (1 mL). Bromotrimethylsilane (750 μL, 5.7 mmol) was added and the mixture was stirred for 4 h whereupon the LC-MS confirmed the starting material was consumed. The solvent was removed under reduced pressure. The resulting residue was dissolved in methanol:water (1:1, 3 mL) and shaken for 30 min. The mixture was filtered over a pad of Celite. The Celite was washed with ethyl acetate. The combined filtrates were washed with brine, dried over anhydrous sodium sulfate and concentrated under reduced pressure to give 2-(2,2-dichloro-N-(3-(3-(2,6-dichlorophenyl)isoxazol-5-yl)phenyl)acetamido)ethylphosphonic acid (Cpd. No. 2) as a white solid. $^1$H NMR (DMSO-d$_6$): 8.02 (m, 2H), 7.69-7.56 (m, 5H), 7.38 (s, 1H), 6.33 (s, 1H), 3.86 (m, 2H), 1.83 ppm (m, 1H). MW=524 confirmed by LC-MS, t$_r$=11.24 min (Method Y) MH$^+$=522-526.

Synthesis of N-(4-(2-Aminoacetamido)-5-methyl-3-oxohexyl)-2,2-dichloro-N-(2-(3-(2,6-dichlorophenyl)isoxazol-5-yl)pyridin-4-yl)acetamide
(See Scheme 3) (Cpd. No. 50)

Synthesis of (R)-tert-Butyl 1-(Methoxy(methyl)amino)-3-methyl-1-oxobutan-2-ylcarbamate N-Boc-L-valine (3.72 g, 17.2 mmol) and N,O-dimethylhydroxylamine hydrochloride (1.84 g, 18.86 mmol) were dissolved in anhydrous methylene chloride (50 mL) under nitrogen. Triethylamine (2.09 g, 20.64 mmol) was added to the mixture, followed by dropwise addition of diethyl cyanophosphonate (3.09 g, 18.92 mmol). The resulting mixture was stirred at room temperature for 12 h. The reaction was then diluted with methylene chloride (150 mL) and washed with water (100 mL). The aqueous layer was extracted with methylene chloride (50 mL). The combined organic layers were washed successively with aqueous sodium bicarbonate (2×100 mL) and brine (2×100 mL), dried over anhydrous sodium sulfate, filtered and concentrated under reduced pressure. The crude residue was carried forward without further purification. $^1$H NMR (CDCl$_3$): 5.28 (d, 1H), 4.61 (m, 1H), 3.76 (s, 3H), 3.20 (s, 3H), 2.09-1.85 (m, 1H), 1.43 (s, 9H), 0.99 (d, 3H), 0.90 ppm (d, 3H).

Synthesis of (R)-tert-Butyl 2-Methyl-4-oxohex-5-en-3-ylcarbamate

Vinylmagnesium bromide (1M soln in THF, 34.6 mL, 34.6 mmol) was added to a solution of (R)-tert-butyl 1-(methoxy(methyl)amino)-3-methyl-1-oxobutan-2-ylcarbamate (4.5 g, 17.30 mmol) in anhydrous tetrahydrofuran (50 mL) under nitrogen at −78° C., dropwise, over 20 min. The reaction was slowly warmed to 0° C. and then stirred for an hour at 0° C. The reaction warmed to room temperature and then stirred for 10 h. Acetic anhydride (10 mL) was added to the reaction mixture at 0° C. After several minutes methanol (10 mL) was added to the reaction. The mixture was allowed to stir for 10 min, and then concentrated to a volume of 25 mL. The reaction mixture was washed with water (100 mL) and the aqueous layer was extracted with ethyl acetate (150 mL). The combined organic layers were washed successively with aqueous sodium bicarbonate (2×100 mL) and brine (2×100 mL), dried over anhydrous sodium sulfate, filtered and concentrated under reduced pressure at less than 40° C. The resulting residue was purified by flash column chromatography on silica gel, eluting with 85:15 hexanes:ethyl acetate to provide (R)-tert-butyl 2-methyl-4-oxohex-5-en-3-ylcarbamate (2.52 g) as a white solid. $^1$H NMR (CDCl$_3$): 6.50-6.32 (m, 2H), 5.85 (d, 1H), 5.22 (d, 1H), 4.56 (dd, 1H), 2.18 (m, 1H), 1.44 (s, 9H), 1.01 (d, 3H), 0.80 ppm (d, 3H).

Synthesis of tert-Butyl 6-(2-(3-(2,6-Dichlorophenyl)isoxazol-5-yl)pyridin-4-ylamino)-2-methyl-4-oxohexan-3-ylcarbamate 3-(2,6-Dichlorophenyl)-5-(5-amino-2-pyridyl)isoxazole (0.34 g, 0.99 mmol), (R)-tert-butyl 2-methyl-4-oxohex-5-en-3-ylcarbamate (0.64 g, 2.8 mmol) and sodium bicarbonate (0.25 g, 3.0 mmol) were dissolved in a mixture of methanol (1 mL) and water (1 mL) in a closed vial. The mixture was heated at 100° C. for 13 h. The reaction mixture was concentrated under reduced pressure. The resulting residue was dissolved in ethyl acetate (50 mL) and washed successively with water (25 mL) and brine (2×25 mL). The organic layer was dried over anhydrous sodium sulfate, filtered and concentrated under reduced pressure. The resulting residue was purified by flash column chromatography on silica gel, eluting with 0.5:99.5 methanol:methylene chloride to provide tert-butyl 6-(2-(3-(2,6-dichlorophenyl)isoxazol-5-yl)pyridin-4-ylamino)-2-methyl-4-oxohexan-3-ylcarbamate (0.445 g) as a yellow solid. $^1$H NMR (CDCl$_3$): 8.36 (d, 1H), 7.45-7.32 (m, 4H), 7.20 (s, 1H), 6.58 (d, 1H), 5.08 (d, 1H), 4.18-4.08 (m, 1H), 3.65-3.60 (m, 2H), 2.92-2.85 (m, 3H), 2.06-2.01 (m, 1H), 1.41 (s, 9H), 1.06 (d, 3H), 0.89 ppm (d, 3H). MW=533 confirmed by LC-MS, t$_r$=12.78 min (Method Y) MH$^+$=531-535.

Synthesis of tert-Butyl 6-(2,2-Dichloro-N-(2-(3-(2,6-dichlorophenyl)isoxazol-5-yl)pyridin-4-yl)acetamido)-2-methyl-4-oxohexan-3-ylcarbamate tert-Butyl 6-(2-(3-(2,6-dichlorophenyl)isoxazol-5-yl)pyridin-4-ylamino)-2-methyl-4-oxohexan-3-ylcarbamate (445 mg, 0.83 mmol) was dissolved in methylene chloride (10 mL) with triethylamine (140 μL, 1.0 mmol). The solution was cooled on an ice-water bath and then a solution of dichloroacetyl chloride (100 μL, 1.0 mmol) in methylene chloride (1 mL) was added dropwise. The reaction mixture was allowed to stir overnight while warming to room temperature. The solution was washed successively with water and saturated sodium bicarbonate solution, then dried over anhydrous sodium sulfate, filtered and concentrated under reduced pressure. The resulting residue was purified by flash column chromatography on silica gel, eluting with 0.5:99.5 methanol:methylene chloride to provide tert-butyl 6-(2,2-dichloro-N-(2-(3-(2,6-dichlorophenyl)isoxazol-5-yl)pyridin-4-yl)acetamido)-2-methyl-4-oxohexan-3-ylcarbamate (185 mg) as a pink foam. $^1$H NMR (CDCl$_3$): 8.85 (d, 1H), 7.91 (d, 1H), 7.61-7.35 (m, 5H), 7.18 (s, 1H), 6.11 (s, 1H), 5.02 (d, 1H), 4.28-4.08 (m, 2H), 3.15-2.82 (m, 3H), 2.20-2.10 (m, 1H), 1.42 (s, 9H), 1.08 (d, 3H), 0.85 ppm (d, 3H). MW=644 confirmed by LC-MS, t$_r$=16.72 min (Method Y) MH$^+$=642-646.

Synthesis of N-(4-Amino-5-methyl-3-oxohexyl)-2,2-dichloro-N-(2-(3-(2,6-dichlorophenyl)isoxazol-5-yl)pyridin-4-yl)acetamide (Cpd. No. 3)

Trifluoroacetic acid (1 mL) was added to a solution of tert-butyl 6-(2,2-dichloro-N-(2-(3-(2,6-dichlorophenyl)isoxazol-5-yl)pyridin-4-yl)acetamido)-2-methyl-4-oxohexan-3-ylcarbamate (185 mg, 0.29 mmol) in methylene chloride (2 mL) at 0° C. The resulting mixture was allowed to stir at 0° C. for 2 hours, then concentrated under reduced pressure. The residue was dissolved in methylene chloride (2 mL) and concentrated under reduced pressure, twice more. Then lyophilized to produce N-(4-amino-5-methyl-3-oxohexyl)-2,2-dichloro-N-(2-(3-(2,6-dichlorophenyl)isoxazol-5-yl)pyridin-4-yl)acetamide (Cpd. No. 3, lot 2, 150 mg) as a light orange solid. $^1$H NMR (CD$_3$OD): 8.90 (d, 1H), 8.28 (s, 1H), 7.80-7.75 (m, 1H), 7.65-7.55 (m, 3H), 7.38 (s, 1H), 6.62 (s, 1H), 4.38-4.11 (m, 3H), 3.19-3.08 (m, 2H), 2.55-2.41 (m, 1H), 1.15 (d, 3H), 0.90 ppm (d, 3H). MW=544 confirmed by LC-MS, t$_r$=10.55 min (Method Y) MH$^+$=542-546.

Synthesis of tert-Butyl 2-(6-(2,2-dichloro-N-(2-(3-(2,6-dichlorophenyl)isoxazol-5-yl)pyridin-4-yl)acetamido)-2-methyl-4-oxohexan-3-ylamino)-2-oxoethylcarbamate (Cpd. No. 49)

Pybop (164 mg, 0.32 mmol), diisopropylethylamine (50 mg, 0.39 mmol) and N-boc-L-valine (69 mg, 0.32 mmol) were added to a solution of N-(4-amino-5-methyl-3-oxohexyl)-2,2-dichloro-N-(2-(3-(2,6-dichlorophenyl)isoxazol-5-yl)pyridin-4-yl)acetamide (Cpd. No. 3, lot 2, 75 mg, 0.11 mmol) in methylene chloride (5 mL) at 0° C. The resulting mixture was stirred at room temperature for 5 h. The reaction mixture was then diluted with methylene chloride (15 mL) and washed successively with water and brine, dried over anhydrous magnesium sulfate, filtered and concentrated under reduced pressure. The resulting residue was purified by prep-scale reverse phase high performance liquid chromatography to provide tert-butyl 6-(2,2-dichloro-N-(2-(3-(2,6-dichlorophenyl)isoxazol-5-yl)pyridin-4-yl)acetamido)-2-methyl-4-oxohexan-3-ylcarbamate (Cpd. No. 49,100 mg) as a white solid. $^1$H NMR (CDCl$_3$): 8.86 (d, 1H), 7.98 (s, 1H), 7.45-7.33 (m, 5H), 5.98 (s, 1H), 5.66 (br s, 1H), 4.98 (br s, 1H), 4.55-4.51 (m, 2H), 4.11-4.02 (m, 3H), 3.00-2.93 (m, 2H), 2.20 (m, 1H), 1.48 (s, 9H), 1.09 (d, 3H), 0.90 ppm (d, 3H).

Synthesis of N-(4-(2-Aminoacetamido)-5-methyl-3-oxohexyl)-2,2-dichloro-N-(2-(3-(2,6-dichlorophenyl)isoxazol-5-yl)pyridin-4-yl)acetamide (Cpd. No. 50)

Trifluoroacetic acid (5 mL) was added to a solution of tert-butyl 6-(2,2-dichloro-N-(2-(3-(2,6-dichlorophenyl)isoxazol-5-yl)pyridin-4-yl)acetamido)-2-methyl-4-oxohexan-3-ylcarbamate (Cpd. No. 49,100 mg) in methylene chloride (5 mL) at 0° C. The resulting mixture was allowed to stir at 0° C. for 3 hours, then concentrated under reduced pressure. The residue was dissolved in methylene chloride (2 mL) and concentrated under reduced pressure, twice more. Then lyophilized to produce N-(4-(2-aminoacetamido)-5-methyl-3-oxohexyl)-2,2-dichloro-N-(2-(3-(2,6-dichlorophenyl)isoxazol-5-yl)pyridin-4-yl)acetamide (R937672) as a pale yellow solid. $^1$H NMR (CD$_3$OD): 8.88 (d, 1H), 8.02 (s, 1H), 7.71 (m, 1H), 7.52-7.40 (m, 4H), 5.98 (s, 1H), 4.56-4.50 (m, 2H), 4.22-4.01 (m, 4H), 3.00-2.91 (m, 2H), 2.18 (m, 1H), 0.91 (d, 3H), 0.79 ppm (d, 3H).

The following compounds were synthesized essentially according to the methods described above. Compounds were characterized by LC-MS and/or proton NMR.

Cpd. No. 1 Diethyl 2-(2,2-Dichloro-N-(3-(3-(2,6-dichlorophenyl)isoxazol-5-yl)phenyl)acetamido)ethylphosphonate. MW=580 confirmed by LC-MS, t$_r$=11.55 min (Method A) MH$^+$=578-582

Cpd. No. 2 2-(2,2-Dichloro-N-(3-(3-(2,6-dichlorophenyl)isoxazol-5-yl)phenyl)acetamido)ethylphosphonic acid. MW=524 confirmed by LC-MS, t$_r$=11.24 min (Method Y) MH$^+$=522-526

Cpd. No. 3 N-(4-Amino-5-methyl-3-oxohexyl)-2,2-dichloro-N-(2-(3-(2,6-dichlorophenyl)isoxazol-5-yl)pyridin-4-yl)acetamide. MW=544 confirmed by LC-MS, t$_r$=10.55 min (Method Y) MH$^+$=542-546

Cpd. No. 4 4-Amino-7-(2,2-dichloro-N-(2-(3-(2,6-dichlorophenyl)isoxazol-5-yl)pyridin-4-yl)acetamido)-5-oxoheptanoic Acid. MW=574 confirmed by LC-MS, t$_r$=10.07 min (Method Y) MH$^+$=572-576

Cpd. No. 5 2-Amino-7-(2,2-dichloro-N-(2-(3-(2,6-dichlorophenyl)isoxazol-5-yl)pyridin-4-yl)acetamido)-5-oxoheptanoic acid. MW=574 confirmed by LC-MS, t$_r$=10.08 min (Method Y) MH$^+$=572-576

Cpd. No. 11 Diethyl 5-(2,2-Dichloro-N-(2-(3-(2,6-dichlorophenyl)isoxazol-5-yl)pyridin-4-yl)acetamido)-3-oxopentylphosphonate. MW=637 confirmed by LC-MS, t$_r$=14.00 min (Method Y) MH$^+$=635-639

Cpd. No. 12 Methyl 3-(2,2-Dichloro-N-(3-(3-(2,6-dichlorophenyl)isoxazol-5-yl)phenyl)acetamido)propanoate. MW=502 confirmed by LC-MS, t$_r$=15.88 min (Method Y) MH$^+$=500-504

Cpd. No. 47 tert-Butyl 1-(6-(2,2-Dichloro-N-(2-(3-(2,6-dichlorophenyl)isoxazol-5-yl)pyridin-4-yl)acetamido)-2-methyl-4-oxohexan-3-ylamino)-3-methyl-1-oxobutan-2-ylcarbamate. MW=744 confirmed by LC-MS, t$_r$=17.66 min (Method Y) MH$^+$=742-746

Cpd. No. 48 2-Amino-N-(6-(2,2-dichloro-N-(2-(3-(2,6-dichlorophenyl)isoxazol-5-yl)pyridin-4-yl)acetamido)-2-methyl-4-oxohexan-3-yl)-3-methylbutanamide. MW=643 confirmed by LC-MS, t$_r$=11.82 min (Method Y) MH$^+$=641-645

Cpd. No. 49 tert-Butyl 2-(6-(2,2-Dichloro-N-(2-(3-(2,6-dichlorophenyl)isoxazol-5-yl)pyridin-4-yl)acetamido)-2-methyl-4-oxohexan-3-ylamino)-2-oxoethylcarbamate. MW=701 confirmed by LC-MS, t$_r$=17.21 min (Method Y) MH$^+$=699-703

Cpd. No. 50 N-(4-(2-Aminoacetamido)-5-methyl-3-oxohexyl)-2,2-dichloro-N-(2-(3-(2,6-dichlorophenyl)isoxazol-5-yl)pyridin-4-yl)acetamide. MW=601 confirmed by LC-MS, t$_r$=10.72 min (Method Y) MH$^+$=599-603

Cpd. No. 51 tert-Butyl 1-(6-(2,2-Dichloro-N-(2-(3-(2,6-dichlorophenyl)isoxazol-5-yl)pyridin-4-yl)acetamido)-2-methyl-4-oxohexan-3-ylamino)-3-methyl-1-oxopentan-2-ylcarbamate. MW=758 confirmed by LC-MS, t$_r$=17.99 min (Method Y) MH$^+$=756-760

Cpd. No. 52 2-Amino-N-(6-(2,2-dichloro-N-(2-(3-(2,6-dichlorophenyl)isoxazol-5-yl)pyridin-4-yl)acetamido)-2-methyl-4-oxohexan-3-yl)-3-methylpentanamide. MW=657 confirmed by LC-MS, t$_r$=10.82 min (Method Y) MH$^+$=655-659

Cpd. No. 53 tert-Butyl 2-(6-(2,2-Dichloro-N-(2-(3-(2,6-dichlorophenyl)isoxazol-5-yl)pyridin-4-yl)acetamido)-2-methyl-4-oxohexan-3-ylcarbamoyl)-4-hydroxypyrrolidine-1-carboxylate. MW=757 confirmed by LC-MS, t$_r$=16.55 min (Method Y) MH$^+$=755-759

Cpd. No. 55 tert-Butyl 4-(tert-Butoxycarbonylamino)-5-(6-(2,2-dichloro-N-(2-(3-(2,6-dichlorophenyl)isoxazol-5-yl)pyridin-4-yl)acetamido)-2-methyl-4-oxohexan-3-ylamino)-5-oxopentanoate. MW=830 confirmed by LC-MS, t$_r$=18.75 min (Method Y) MH$^+$=828-832

Cpd. No. 56 4-Amino-5-(6-(2,2-dichloro-N-(2-(3-(2,6-dichlorophenyl)isoxazol-5-yl)pyridin-4-yl)acetamido)-2-methyl-4-oxohexan-3-ylamino)-5-oxopentanoic Acid. MW=673 confirmed by LC-MS, t$_r$=9.82 min (Method Y) MH$^+$=671-675

Cpd. No. 59 N-(4-Amino-5-methyl-3-oxoheptyl)-2,2-dichloro-N-(2-(3-(2,6-dichlorophenyl)isoxazol-5-yl)pyridin-4-yl)acetamide. MW=558 confirmed by LC-MS, $t_r$=11.12 min (Method Y) MH$^+$=556-560

Cpd. No. 60 N-(4-Amino-3-oxobutyl)-2,2-dichloro-N-(2-(3-(2,6-dichlorophenyl)isoxazol-5-yl)pyridin-4-yl)acetamide. MW=502 confirmed by LC-MS, $t_r$=10.91 min (Method Y) MH$^+$=500-504

Melting Point Methods

Melting points were obtained on an Electrothermal IA9100 series digital melting point apparatus. All Melting points are uncorrected.

Elemental Analysis

Elemental analysis was performed by Desert Analytics, Tuscon, Ariz.

NMR Methods

NMR spectra were obtained on a 300 MHz Varian Mercury system.

Microwave Methods

Microwave reactions were carried out in the Personal Chemistry, SmithCreator microwave.

LC-MS Methods

General

LC-MS was performed on a Waters Micromass ZQ instrument with electrospray ionization. The HPLC component was a Waters Model 2690 Separation module coupled to a Waters Model 996 photodiode array detector.

Method Y

This method utilized a 2.1×150 mm Agilent Zorbax 5 µM C-18 reversed phase column with a flow rate of 0.3 mL/min and a gradient of 5-100% acetonitrile with water containing 0.05% formic acid over 15 min, then continuing for 5 min with 100% acetonitrile.

Method Z

This method utilized a 2.1×5 mm Agilent Zorbax 5 µM C-18 reversed phase column with a flow rate of 0.5 mL/min and a gradient of 5-100% acetonitrile with water containing 0.1% trifluoroacetic acid over 8 min, then continuing for 2 min with 100% acetonitrile.

Method A

LC-MS was performed on a Waters Micromass ZMD instrument with electrospray ionization. This method utilized a 2.1×5 mm Agilent Zorbax 5 µM C-18 reversed phase column with a flow rate of 0.3 mL/min and a gradient of 10-100% acetonitrile with water containing 0.05% formic acid over 10 min, then continuing for 8 min with 100% acetonitrile.

Method B

This method utilized a 2.1×5 mm Agilent Zorbax 5 µM C-18 reversed phase column with a flow rate of 0.8 mL/min and a gradient of 5-95% acetonitrile with water containing 0.05% formic acid over 5 min, then continuing for 2 min with 95% acetonitrile.

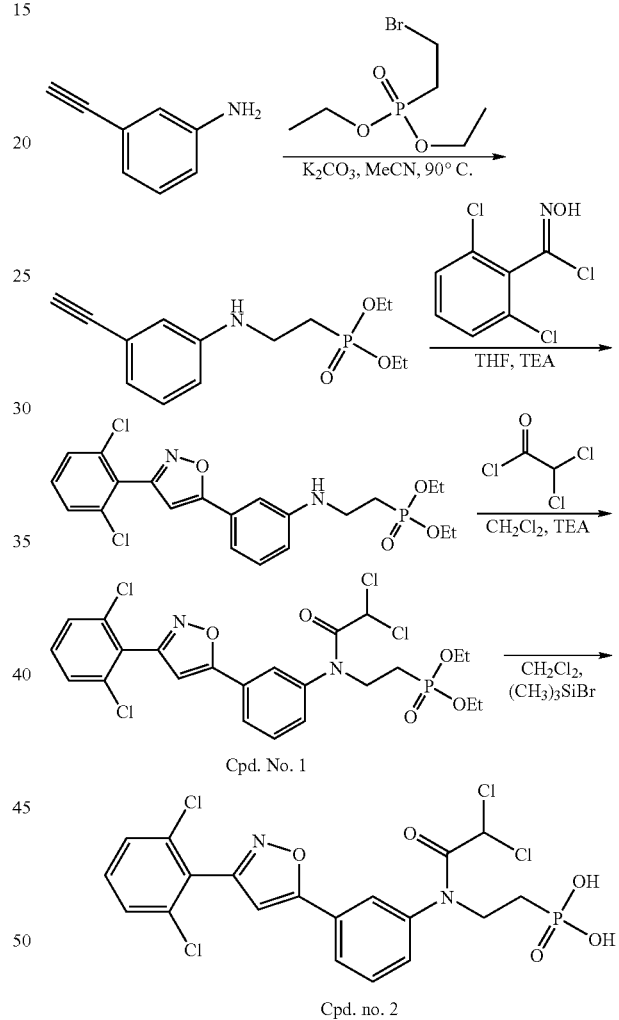

Scheme 2
Synthesis of Cpd. No. 2

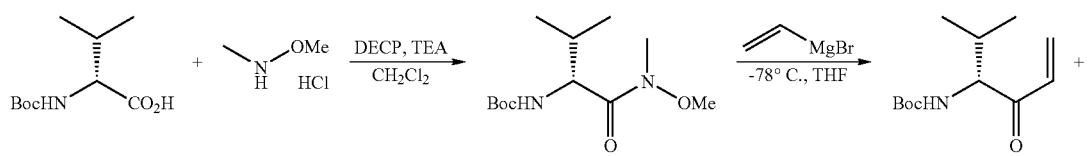

Scheme 3
Synthesis of Cpd. No. 50

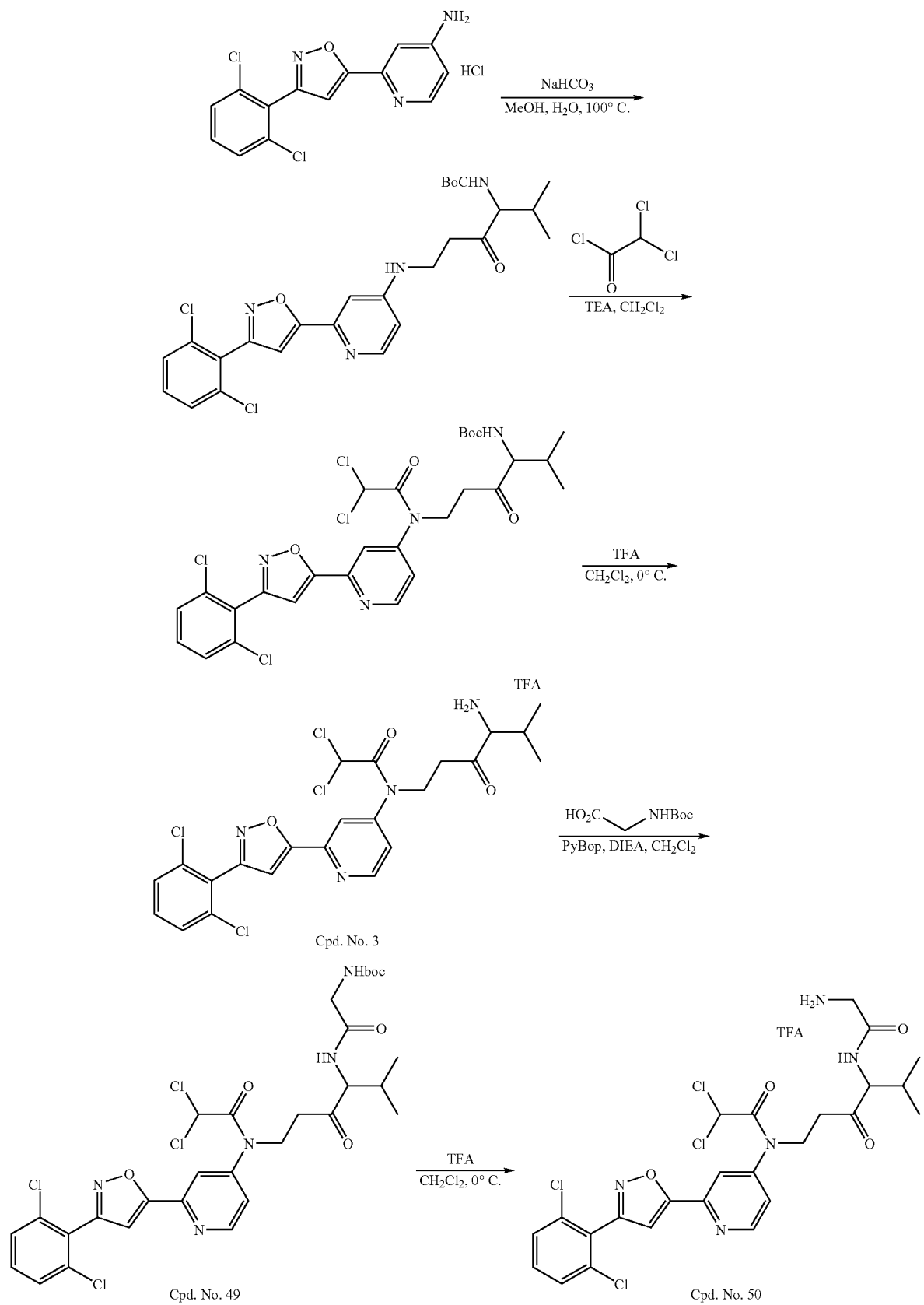

Synthesis of (R)-4-Amino-7-(2,2-dichloro-N-(2-(3-(2,6-dichlorophenyl)isoxazol-5-yl)pyridin-4-yl)acetamido)-5-oxoheptanoic Acid Trifluoroacetate Salt (Cpd. No. 4)(See Scheme 4)

Synthesis of (S)-tert-Butyl 4-(tert-Butoxycarbonylamino)-5-(methoxy(methyl)amino)-5-oxopentanoate N-α-t-Boc-L-Glutamic acid-γ-t-butyl ester (6.06 g, 20 mmol), N,O-dimethylhydroxylamine hydrochloride (2.4 g, 24 mmol) and triethylamine (5.6 mL, 40 mmol) were dissolved in anhydrous dichloromethane and treated with diethyl cyanophosphonate (6.06 mL, 24 mmol). After stirring at room temperature overnight, the reaction mixture was diluted with water. The layers were separated and the aqueous layer was extracted with dichloromethane twice. The combined organic layers were washed successively with saturated sodium bicarbonate solution (twice) and brine. The organic solution was dried over anhydrous sodium sulfate, filtered and concentrated under reduced pressure. The resulting residue was passed through a pad of silica gel, eluting with 1:4 ethyl acetate:hexanes to yield (S)-tert-butyl 4-(tert-butoxycarbonylamino)-5-(methoxy(methyl)amino)-5-oxopentanoate (4.21 g) as a pale yellow syrup. $^1$H NMR (CDCl$_3$): 5.19 (m, 1H), 4.65 (m, 1H), 3.76 (s, 3H), 3.19 (s, 3H), 2.32 (m, 2H), 2.03-1.97 (m, 1H), 1.85-1.81 (m, 1H), 1.38 ppm (s, 18H). MW=346 confirmed by LC-MS, $t_r$=15.46 min (Method Y) MH$^+$=347.

Synthesis of (S)-tert-Butyl 4-(tert-Butoxycarbonylamino)-5-oxohept-6-enoate (S)-tert-Butyl 4-(tert-butoxycarbonylamino)-5-(methoxy(methyl)amino)-5-oxopentanoate (4.12 g, 12.2 mmol) was dissolved in anhydrous tetrahydrofuran (100 mL) and cooled to −70° C. under nitrogen. Vinylmagnesium bromide (37 mL, 1.0 M soln in THF, 3.0 eq) was added dropwise. The reaction stirred for 30 min at −70° C. and was then the cooling bath was removed and the reaction stirred at room temperature overnight. The mixture was colled on in an ice bath and acetic anhydride (20 mL) was added, followed by methanol (27 mL). The mixture was concentrated under pressure to a small volume and then diluted with ethyl acetate. The reaction mixture was washed successively with water and brine and dried over anhydrous sodium sulfate, filtered and concentrated under reduced pressure. The resulting residue was purified by flash column chromatography, on silica gel, eluting with 1:4 ethyl acetate:hexanes to yield (S)-tert-butyl 4-(tert-butoxycarbonylamino)-5-oxohept-6-enoate (0.94 g) as a yellow oil. $^1$H NMR (CDCl$_3$): 6.48-6.45 (m, 2H), 5.94 (m, 1H), 5.29 (m, 1H), 4.70 (m, 1H), 2.38-2.05 (m, 2H), 2.02 (m, 1H), 1.70 (m, 1H), 1.45 ppm (s, 18H).

Synthesis of (R)-tert-Butyl 4-(tert-Butoxycarbonylamino)-7-(2-(3-(2,6-dichlorophenyl)isoxazol-5-yl)pyridin-4-ylamino)-5-oxoheptanoate (S)-tert-butyl 4-(tert-butoxycarbonylamino)-5-oxohept-6-enoate (0.94 g) and 2-(3-(2,6-dichlorophenyl)isoxazol-5-yl)pyridin-4-amine hydrochloride salt (0.40 g) were dissolved in acetonitrile (4 mL). Diisopropylethylamine (0.52 mL) was added and the mixture wad heated at 89° C. for 25 h. The mixture was cooled to room temperature, diluted with dichloromethane and washed with brine. The organic layer was dried over anhydrous sodium sulfate, filtered and concentrated under reduced pressure. The resulting residue was purified by flash column chromatography, on silica gel, eluting with 0.5:99.5 methanol:dichloromethane then 5:95 methanol:dichloromethane to yield (R)-tert-butyl 4-(tert-butoxycarbonylamino)-7-(2-(3-(2,6-dichlorophenyl)isoxazol-5-yl)pyridin-4-ylamino)-5-oxoheptanoate (316 mg) as a beige foam. $^1$H NMR (CDCl$_3$): 8.25 (m, 1H), 7.40 (m, 2H), 7.30 (m, 1H), 7.17 (m, 1H), 6.98 (m, 1H), 6.47 (m, 1H), 5.20 (m, 1H), 5.00 (m, 1H), 4.22 (m, 1H), 3.59 (m, 2H), 2.90 (m, 2H), 2.32 (m, 2H), 2.10 (m, 1H), 1.83 (m, 1H), 1.45 ppm (s, 18H). MW=619 confirmed by LC-MS, $t_r$=13.23 min (Method Y) MH$^+$=617-621.

Synthesis of (R)-tert-Butyl 4-(tert-Butoxycarbonylamino)-7-(2,2-dichloro-N-(2-(3-(2,6-dichlorophenyl)isoxazol-5-yl)pyridin-4-yl)acetamido)-5-oxoheptanoate (R)-tert-butyl 4-(tert-butoxycarbonylamino)-7-(2-(3-(2,6-dichlorophenyl)isoxazol-5-yl)pyridin-4-ylamino)-5-oxoheptanoate (280 mg, 0.45 mmol) was dissolved in anhydrous dichloromethane with triethylamine (126 µL, 0.90 mmol). The mixture was cooled in an ice-bath under nitrogen, then a solution of dichloroacetyl chloride (66 µL, 0.68 mmol) was added dropwise. After the addition was completed the ice-bath was removed and the mixture was stirred at room temperature overnight. The reaction mixture was diluted with dichloromethane and then washed successively with water, 10% hydrochloric acid and saturated sodium bicarbonate solution. The organic solution was dried over anhydrous sodium sulfate, filtered and concentrated under reduced pressure. The resulting residue was purified by flash column chromatography, on silica gel, eluting with 99:1 dichloromethane:methanol to yield (R)-tert-butyl 4-(tert-butoxycarbonylamino)-7-(2,2-dichloro-N-(2-(3-(2,6-dichlorophenyl)isoxazol-5-yl)pyridin-4-yl)acetamido)-5-oxoheptanoate (165 mg) as a white foam. $^1$H NMR (CDCl$_3$): 8.77 (m, 1H), 7.89 (m, 1H), 7.42 (m, 2H), 7.40-7.31 (m, 2H), 7.07 (s, 1H), 6.00 (s, 1H), 5.20 (m, 1H), 4.20 (m, 1H), 4.00 (m, 2H), 2.97 (m, 2H), 2.27 (m, 2H), 2.10 (m, 1H), 1.78 (m, 1H), 1.41 ppm (m, 18H). MW=730 confirmed by LC-MS, $t_r$=13.34 min (Method A) MH$^+$=728-732.

Synthesis of (R)-4-Amino-7-(2,2-dichloro-N-(2-(3-(2,6-dichlorophenyl)isoxazol-5-yl)pyridin-4-yl)acetamido)-5-oxoheptanoic Acid Trifluoroacetate Salt (Cpd. No. 4) (See Scheme 4)

(R)-tert-Butyl 4-(tert-butoxycarbonylamino)-7-(2,2-dichloro-N-(2-(3-(2,6-dichlorophenyl)isoxazol-5-yl)pyridin-4-yl)acetamido)-5-oxoheptanoate (165 mg) was dissolved in anhydrous dichloromethane (2 mL) and cooled in an ice-bath under nitrogen. Then trifluoroacetic acid (2 mL) was added. After 4.5 h at 4° C. the mixture was concentrated under reduced pressure. The residue was dissolved and concentrated under reduced pressure again to give (R)-4-amino-7-(2,2-dichloro-N-(2-(3-(2,6-dichlorophenyl)isoxazol-5-yl)pyridin-4-yl)acetamido)-5-oxoheptanoic acid trifluoroacetate salt as a tan solid. $^1$H NMR (CD$_3$CN): 8.73 (m, 1H), 7.99 (m, 2H), 7.48 (m, 3H), 7.11 (s, 1H), 6.48 (s, 1H), 4.05 (m, 2H), 3.05-2.85 (m, 2H), 2.30 (m, 2H), 2.15 (m, 1H), 1.97 (m, 2H), 1.80 ppm (m, 1H). MW=594 confirmed by LC-MS, $t_r$=10.07 min (Method Y) MH$^+$=592-596.

Synthesis of 2,2-Dichloro-N-(2-(3-(2,6-dichlorophenyl)isoxazol-5-yl)pyridin-4-yl)-N-(isopropoxymethyl)acetamide (Cpd. No. 9) (See Scheme 5)

Synthesis of 2-(3-(2,6-Dichlorophenyl)isoxazol-5-yl)-N-(isopropoxymethyl)pyridin-4-amine Sodium hydride (120 mg, 2.9 mmol) was added slowly to isopropyl alcohol (15 mL) at 0° C. Once the evolution of hydrogen ceased 2-(3-(2,6-dichlorophenyl)isoxazol-5-yl)pyridin-4-amine hydrochloride (200 mg, 0.58 mmol) and paraformaldehyde (147 mg, 1.64 mmol) added. The resulting mixture was stirred at room temperature for 5 h and hydrolyzed with ice-cooled water and extracted with ethyl acetate. The organic extracts were washed with water, then dried over anhydrous sodium sulfate, filtered and concentrated under reduced pressure to yield 2-(3-(2,6-dichlorophenyl)isoxazol-5-yl)-N-(isopropoxymethyl)pyridin-4-amine (269 mg). The product was carried forward without further purification. $^1$H NMR (CDCl$_3$): 8.38 (d, 1H), 7.44 (m, 1H), 7.35 (m, 1H), 7.00 (s, 1H), 6.70 (m, 1H), 4.80 (d, 2H), 3.90 (m, 1H), 1.22 ppm (d, 6H).

Synthesis of 2,2-Dichloro-N-(2-(3-(2,6-dichlorophenyl)isoxazol-5-yl)pyridin-4-yl)-N-(isopropoxymethyl)acetamide (Cpd. No. 9) (See Scheme 5)

2-(3-(2,6-Dichlorophenyl)isoxazol-5-yl)-N-(isopropoxymethyl)pyridin-4-amine (269 mg, 0.58 mmol) was dissolved in anhydrous dichloromethane with triethylamine (100 µL, 0.70 mmol). The mixture was cooled in an ice-bath under nitrogen, then a solution of dichloroacetyl chloride (70 µL, 0.70 mmol) was added dropwise. After the addition was completed the ice-bath was removed and the mixture was stirred at room temperature overnight. The reaction mixture was diluted with dichloromethane and then washed successively with water, 10% hydrochloric acid and saturated sodium bicarbonate solution. The organic solution was dried over anhydrous sodium sulfate, filtered and concentrated under reduced pressure. The resulting residue was purified by flash column chromatography, on silica gel, eluting with 99:1 dichloromethane:methanol to yield 2,2-dichloro-N-(2-(3-(2,6-dichlorophenyl)isoxazol-5-yl)pyridin-4-yl)-N-(isopropoxymethyl)acetamide (Cpd. No. 4). $^1$H NMR (CDCl$_3$): 8.81 (d, 1H), 8.02 (s, 1H), 7.51-7.32 (m, 3H), 7.12 (s, 1H), 6.23 (s, 1H), 5.21 (s, 2H), 6.00 (s, 1H), 3.90 (m, 1H), 3.10 ppm (m, 6H). MW=489 confirmed by LC-MS, $t_r$=14.57 min (Method Y) MH$^+$=487-491.

Synthesis of (S)-tert-Butyl 2-(2-(2,2-Dichloro-N-(3-(3-(2,6-dichlorophenyl)isoxazol-5-yl)phenyl)acetamido)ethylamino)-2-oxo-1-phenylethylcarbamate (Cpd. No. 19) (See Scheme 6)

Synthesis of tert-Butyl 2-(3-Ethynylphenylamino)-2-oxoethylcarbamate

3-Ethynylaniline (1.0 g, 8.54 mmol), N-Boc glycine (2.7 g, 15.41 mmol) and PyBOP (8.1 g, 15.41 mmol) were combined in dichloromethane (25 mL). Diisopropylethylamine (3.3 g, 25.61 mmol) was added to the solution and the mixture was allowed to stir at room temperature under argon for 10 h. The reaction mixture was diluted with dichloromethane and then washed successively with water and brine. The organic solution was dried over anhydrous sodium sulfate, filtered and concentrated under reduced pressure. The resulting residue was purified by flash column chromatography, on silica gel, eluting with 95:5 hexanes:ethyl acetate to yield tert-butyl 2-(3-ethynylphenylamino)-2-oxoethylcarbamate. $^1$H NMR (CDCl$_3$): 8.45 (br s, 1H), 7.62 (m, 1H), 7.58 (m, 1H), 7.30 (m, 2H), 5.38 (br s, 1H), 3.95 (d, 2H), 3.08 (s, 1H), 1.48 ppm (s, 9H).

Synthesis of tert-Butyl 2-(3-(3-(2,6-Dichlorophenyl)isoxazol-5-yl)phenylamino)-2-oxoethylcarbamate tert-Butyl 2-(3-ethynylphenylamino)-2-oxoethylcarbamate (1.6 g, 5.83 mmol) was dissolved in anhydrous tetrahydrofuran (25 mL) and treated with triethylamine (0.82 g, 8.1 mmol) and then 2,6-dichloro-N-hydroxybenzimidoyl chloride (1.4 g, 6.3 mmol). After stirring 15 min at room temperature the mixture was heated at reflux for 4 h. The mixture was diluted with ethyl acetate, washed with brine, dried over anhydrous sodium sulfate, filtered and concentrated under reduced pressure to give tert-butyl 2-(3-(3-(2,6-dichlorophenyl)isoxazol-5-yl)phenylamino)-2-oxoethylcarbamate. $^1$H NMR (CDCl$_3$): 8.51 (br s, 1H), 8.01 (s, 1H), 7.51-7.45 (m, 2H), 7.40-7.28 (m, 4H), 6.63 (m, 1H), 5.28 (br s, 2H), 3.95 (d, 2H), 1.45 ppm (s, 9H).

Synthesis of tert-Butyl 2-(3-(3-(2,6-Dichlorophenyl)isoxazol-5-yl)phenylamino)ethylcarbamate tert-Butyl 2-(3-(3-(2,6-dichlorophenyl)isoxazol-5-yl)phenylamino)-2-oxoethylcarbamate (500 mg, 1.08 mmol) was dissolved in anhydrous tetrahydrofuran (10 mL) and cooled to 0° C. Borane-tetrahydrofuran complex (1M soln in THF, 10.8 mL, 10.8 mmol) was added dropwise to the cool solution. The reaction mixture was allowed to stir while slowly warming to room temperature for 5 h. The reaction was quenched with 1N hydrochloric acid (25 mL) and extracted with ethyl acetate. The organic layer was concentrated under reduced pressure to yield tert-butyl 2-(3-(3-(2,6-dichlorophenyl)isoxazol-5-yl)phenylamino)ethylcarbamate as a white solid. The product was carried forward without further purification. $^1$H NMR (CDCl$_3$): 7.98 (s, 1H), 7.55-7.50 (m, 2H), 7.48-7.35 (m, 4H), 6.48 (s, 1H), 5.18 (br s, 1H), 4.00 (m, 2H), 3.58 (m, 2H), 1.48 ppm (s, 9H).

Synthesis of tert-Butyl 2-(2,2-Dichloro-N-(3-(3-(2,6-dichlorophenyl)isoxazol-5-yl)phenyl)acetamido)ethylcarbamate tert-Butyl 2-(3-(3-(2,6-dichlorophenyl)isoxazol-5-yl)phenylamino)ethylcarbamate (230 mg, 0.51 mmol) was dissolved in anhydrous dichloromethane with triethylamine (120 µL, 0.82 mmol). The mixture was cooled in an ice-bath under nitrogen, then a solution of dichloroacetyl chloride (120 mg, 0.82 mmol) was added dropwise. After the addition was completed the ice-bath was removed and the mixture was stirred at room temperature overnight. The reaction mixture was diluted with dichloromethane and then washed successively with water, 10% hydrochloric acid and saturated sodium bicarbonate solution. The organic solution was dried over anhydrous sodium sulfate, filtered and concentrated under reduced pressure. The resulting residue was purified by flash column chromatography, on silica gel, eluting with 95:5 hexanes:ethyl acetate to yield tert-butyl 2-(2,2-dichloro-N-(3-(3-(2,6-dichlorophenyl)isoxazol-5-yl)phenyl)acetamido)ethylcarbamate. $^1$H NMR (CDCl$_3$): 7.99 (d, 1H), 7.82 (br s, 1H), 7.62 (m, 1H), 7.48-7.30 (m, 4H), 6.78 (s, 1H), 5.82 (s, 1H), 4.95 (m, 1H), 3.95 (m, 2H), 3.43 (m, 2H), 1.42 ppm (s, 9H).

Synthesis of N-(2-Aminoethyl)-2,2-dichloro-N-(3-(3-(2,6-dichlorophenyl)isoxazol-5-yl)phenyl)acetamide Trifluoroacetate Salt tert-butyl 2-(2,2-dichloro-N-(3-(3-(2,6-dichlorophenyl)isoxazol-5-yl)phenyl)acetamido)ethylcarbamate (100 mg, 0.18 mmol) was dissolved in anhydrous dichloromethane (3 mL) and cooled in an ice-bath under nitrogen. Then trifluoroacetic acid (3 mL) was added. After 3 h at 4° C. the mixture was concentrated under reduced pressure. The residue was dissolved and concentrated under reduced pressure again to give N-(2-aminoethyl)-2,2-dichloro-N-(3-(3-(2,6-dichlorophenyl)isoxazol-5-yl)phenyl)acetamide trifluoroacetate salt as a white solid. $^1$H NMR (CDCl$_3$): 8.04 (s, 1H), 7.65-7.62 (m, 2H), 7.43-7.30 (m, 4H), 6.73 (s, 1H), 5.95 (s, 1H), 4.21 (m, 2H), 3.35 ppm (m, 2H).

Synthesis of (S)-tert-Butyl 2-(2-(2,2-Dichloro-N-(3-(3-(2,6-dichlorophenyl)isoxazol-5-yl)phenyl)acetamido)ethylamino)-2-oxo-1-phenylethylcarbamate (Cpd. No. 1219) (See Scheme 6)

N-(2-Aminoethyl)-2,2-dichloro-N-(3-(3-(2,6-dichlorophenyl)isoxazol-5-yl)phenyl)acetamide trifluoroacetate salt (50 mg, 0.09 mmol) was dissolved in dichloromethane (5 mL), followed by the addition of D-N-Boc phenyl glycine (66 mg, 0.26 mmol), PyBOP (140 mg, 0.27 mmol) and diisopropylethylamine (39 mg, 0.30 mmol). The resulting mixture was allowed to stir at room temperature under argon for 3 h. The reaction mixture was diluted with dichloromethane and then washed successively with water and saturated sodium bicarbonate solution. The organic solution was dried over anhydrous sodium sulfate, filtered and concentrated under reduced pressure. The resulting residue was purified by prep-scale reverse phase high performance liquid chromatography to yield (S)-tert-butyl 2-(2-(2,2-dichloro-N-(3-(3-(2,6-dichlorophenyl)isoxazol-5-yl)phenyl)acetamido)ethylamino)-2-oxo-1-phenylethylcarbamate (Cpd. No. 19). $^1$H NMR (CDCl$_3$): 7.91 (d, 1H), 7.69 (s, 1H), 7.58 (t, 1H), 7.48-7.35 (m, 9H), 6.72 (s, 1H), 6.58 (br s, 1H), 5.82 (s, 1H), 5.75 (d, 1H), 5.18 (br s, 1H), 4.09 (m, 1H), 3.81 (m, 1H), 3.64 (m, 1H), 3.38 (m, 1H), 1.45 ppm (s, 9H). MW=692 confirmed by LC-MS, $t_r$=16.81 min (Method Y) MH$^+$=609-694.

Synthesis of (E/Z)-tert-Butyl 3-(2,2-Dichloro-N-(2-(3-(2,6-dichlorophenyl)isoxazol-5-yl)pyridin-4-yl)acetamido)acrylate (Cpd. No. 54) (See Scheme 7)

Synthesis of (E/Z)-tert-Butyl 3-(2-(3-(2,6-Dichlorophenyl)isoxazol-5-yl)pyridin-4-ylamino)acrylate 2-(3-(2,6-dichlorophenyl)isoxazol-5-yl)pyridin-4-amine (300 mg, 0.98 mmol) and tert-butyl 3-oxopropanoate (300 mg, 2.1 mmol) were combined in 1,2-dichloroethane (5 mL) and treated with sodium triacetoxyborohydride (500 mg, 2.36 mmol) and acetic acid (one drop). The mixture was sonicated at room temperature for 18 h. The reaction was diluted with ethyl acetate and then washed with water, brine and saturated sodium bicarbonate solution. The organic solution was dried over anhydrous sodium sulfate, filtered and concentrated under reduced pressure. The resulting residue was purified by flash column chromatography, on silica gel, eluting with 75:25 hexanes:ethyl acetate to yield (E/Z)-tert-butyl 3-(2-(3-(2,6-dichlorophenyl)isoxazol-5-yl)pyridin-4-ylamino)acrylate. $^1$H NMR (CDCl$_3$): 10.18 (d, 1H), 8.40 (s, 1H), 7.48 (s, 1H), 7.42-7.30 (m, 4H), 6.98 (s, 1H), 6.78 (d, 1H), 4.99 (d, 1H), 1.48 ppm (s, 9H).

Synthesis of (E/Z)-tert-Butyl 3-(2,2-Dichloro-N-(2-(3-(2,6-dichlorophenyl)isoxazol-5-yl)pyridin-4-yl)acetamido)acrylate (Cpd. No. 54) (See Scheme 7)

(E/Z)-tert-Butyl 3-(2-(3-(2,6-dichlorophenyl)isoxazol-5-yl)pyridin-4-ylamino)acrylate (300 mg, 0.69 mmol) was dissolved in anhydrous dichloromethane (25 mL) with triethylamine (120 mg, 1.2 mmol). The mixture was cooled in an ice-bath under nitrogen, then a solution of dichloroacetyl chloride (180 mg, 1.2 mmol) was added dropwise. After the addition was completed the ice-bath was removed and the mixture was stirred at room temperature overnight. The reaction mixture was diluted with dichloromethane and then washed successively with water, 10% hydrochloric acid and saturated sodium bicarbonate solution. The organic solution was dried over anhydrous sodium sulfate, filtered and concentrated under reduced pressure. The resulting residue was purified by flash column chromatography, on silica gel, eluting with 75:25 hexanes:ethyl acetate to yield (E/Z)-tert-butyl 3-(2,2-dichloro-N-(2-(3-(2,6-dichlorophenyl)isoxazol-5-yl)pyridin-4-yl)acetamido)acrylate (Cpd. No. 54). $^1$H NMR (CDCl$_3$): 8.70 (d, 1H), 7.80 (s, 1H), 7.42-7.30 (m, 4H), 7.04 (s, 1H), 6.78 (d, 1H), 6.50 (s, 1H), 6.04 (d, 1H), 1.38 ppm (s, 9H).

Synthesis of (2,2-dichloro-N-(2-(3-(2,6-dichlorophenyl)isoxazol-5-yl)pyridin-4-yl)acetamido)methyl isopropyl carbonate (Cpd. No. 57) (See Scheme 8)
Synthesis of Chloromethyl Isopropyl Carbonate A solution of chloroformic acid chloromethyl ester (6.23 mL, 70.0 mmol) and isopropyl alcohol (4.4 g, 73.0 mmol) in anhydrous ether (150 mL) was added dropwise to a solution of pyridine (5.7 mL) at 0° C. The reaction mixture was stirred for 1 h at 0° C. and then 3 h at room temperature. The reaction mixture was diluted with ether and then washed successively with water, 10% hydrochloric acid and brine. The organic solution was dried over anhydrous sodium sulfate, filtered and concentrated under reduced pressure to yield chloromethyl isopropyl carbonate. The product was carried forward without further purification. $^1$H NMR (CDCl$_3$): 5.68 (s, 2H), 4.90 (m, 1H), 1.32 ppm (d, 6H).

Synthesis of Isopropyl 3-(2-(3-(2,6-Dichlorophenyl)isoxazol-5-yl)pyridin-4-ylamino)propanoate Sodium iodide (1.4 g, 9.3 mmol) was added to a solution of chloromethyl isopropyl carbonate (750 mg, 4.8 mmol) in acetone (5 mL). The resulting mixture was stirred at room temperature for 2.5 h, followed by addition of 2-(3-(2,6-dichlorophenyl)isoxazol-5-yl)pyridin-4-amine (500 mg, 1.6 mmol). The reaction mixture was then stirred at room temperature for 7 d. The reaction mixture was concentrated under reduced pressure to provide isopropyl 3-(2-(3-(2,6-dichlorophenyl)isoxazol-5-yl)pyridin-4-ylamino)propanoate, which was carried forward without further purification. $^1$H NMR (CDCl$_3$): 8.56 (d, 1H), 7.96 (s, 1H), 7.62 (m, 1H), 7.42-7.30 (m, 4H), 7.01 (s, 1H), 6.26 (d, 2H), 5.02 (m, 1H), 1.31 ppm (d, 6H).

Synthesis of (2,2-dichloro-N-(2-(3-(2,6-dichlorophenyl)isoxazol-5-yl)pyridin-4-yl)acetamido)methyl isopropyl carbonate (Cpd. No. 57) (See Scheme 8)

Isopropyl 3-(2-(3-(2,6-dichlorophenyl)isoxazol-5-yl)pyridin-4-ylamino)propanoate (520 mg, 1.23 mmol) was dissolved in anhydrous dichloromethane (25 mL) with triethylamine (270 mg, 2.7 mmol). The mixture was cooled in an ice-bath under nitrogen, then a solution of dichloroacetyl chloride (320 mg, 2.17 mmol) was added dropwise. After the addition was completed the ice-bath was removed and the mixture was stirred at room temperature overnight. The reaction mixture was diluted with dichloromethane and then washed successively with water, 10% hydrochloric acid and saturated sodium bicarbonate solution. The organic solution was dried over anhydrous sodium sulfate, filtered and concentrated under reduced pressure. The resulting residue was purified by flash column chromatography, on silica gel, eluting with 95:5 hexanes:ethyl acetate to yield isopropyl 3-(2,2-dichloro-N-(2-(3-(2,6-dichlorophenyl)isoxazol-5-yl)pyridin-4-yl)acetamido)propanoate (Cpd. No. 57). $^1$H NMR (CDCl$_3$): 8.38 (m, 1H), 8.01 (s, 1H), 7.80 (m, 1H), 7.50-7.41 (m, 4H), 7.18 (s, 1H), 6.86 (s, 1H), 6.32 (s, 2H), 5.08 (m, 1H), 1.38 ppm (s, 6H).

The following compounds were synthesized essentially according to the methods described above. Compounds were characterized by LC-MS and/or proton NMR.

Cpd. No. 6 2,2-Dichloro-N-(3-(3-(2,6-dichlorophenyl)isoxazol-5-yl)phenyl)-N-(methoxymethyl)acetamide. MW=460 confirmed by LC-MS, $t_r$=15.76 min (Method Y) MH$^+$=458-462

Cpd. No. 7 2,2-Dichloro-N-(2-(3-(2,6-dichlorophenyl)isoxazol-5-yl)pyridin-4-yl)-N-(methoxymethyl)acetamide. MW=525 confirmed by LC-MS, $t_r$=8.11 min (Method Y) MH$^+$=523-527

Cpd. No. 8 Ethyl 2-(2,2-Dichloro-N-(2-(3-(2,6-dichlorophenyl)isoxazol-5-yl)pyridin-4-yl)acetamido)acetate. MW=503 confirmed by LC-MS, $t_r$=15.26 min (Method Y) MH$^+$=501-505

Cpd. No. 9 2,2-Dichloro-N-(2-(3-(2,6-dichlorophenyl)isoxazol-5-yl)pyridin-4-yl)-N-(isopropoxymethyl)acetamide. MW=489 confirmed by LC-MS, $t_r$=14.57 min (Method Y) MH$^+$=487-491

Cpd. No. 10 N-(sec-Butoxymethyl)-2,2-dichloro-N-(2-(3-(2,6-dichlorophenyl)isoxazol-5-yl)pyridin-4-yl)acetamide. MW=503 confirmed by LC-MS, $t_r$=14.97 min (Method Y) MH$^+$=501-505

Cpd. No. 13 2,2-Dichloro-N-(2-cyanoethyl)-N-(3-(3-(2,6-dichlorophenyl)isoxazol-5-yl)phenyl)acetamide. MW=469 confirmed by LC-MS, $t_r$=15.07 min (Method Y) MH$^+$=467-471

Cpd. No. 14 tert-Butyl 2-(2,2-Dichloro-N-(3-(3-(2,6-dichlorophenyl)isoxazol-5-yl)phenyl)acetamido)ethylcarbamate. MW=559 confirmed by LC-MS, $t_r$=17.86 min (Method Y) MH$^+$=557-561

Cpd. No. 16 N-(2-Aminoethyl)-2,2-dichloro-N-(3-(3-(2,6-dichlorophenyl)isoxazol-5-yl)phenyl)acetamide. MW=459 confirmed by LC-MS, $t_r$=11.64 min (Method Y) MH$^+$=457-461

Cpd. No. 17 (S)-tert-Butyl 2-(2,2-Dichloro-N-(3-(3-(2,6-dichlorophenyl)isoxazol-5-yl)phenyl)acetamido)ethylamino)-2-oxo-1-phenylethylcarbamate. MW=692 confirmed by LC-MS, $t_r$=16.66 min (Method Y) MH$^+$=690-694

Cpd. No. 18 (S)-N-(2-(2-Amino-2-phenylacetamido)ethyl)-2,2-dichloro-N-(3-(3-(2,6-dichlorophenyl)isoxazol-5-yl)phenyl)acetamide. MW=592 confirmed by LC-MS, $t_r$=11.65 min (Method Y) MH$^+$=590-594

Cpd. No. 19 (S)-tert-Butyl 2-(2-(2,2-Dichloro-N-(3-(3-(2,6-dichlorophenyl)isoxazol-5-yl)phenyl)acetamido)ethylamino)-2-oxo-1-phenylethylcarbamate. MW=692 confirmed by LC-MS, $t_r$=16.81 min (Method Y) MH$^+$=690-694

Cpd. No. 20 (R)-N-(2-(2-Amino-2-phenylacetamido)ethyl)-2,2-dichloro-N-(3-(3-(2,6-dichlorophenyl)isoxazol-5-yl)phenyl)acetamide. MW=592 confirmed by LC-MS, $t_r$=11.75 min (Method Y) MH$^+$=590-594

Cpd. No. 21 (S)-tert-Butyl 1-(2,2-Dichloro-N-(3-(3-(2,6-dichlorophenyl)isoxazol-5-yl)phenyl)acetamido)-3-methylbutan-2-ylcarbamate. MW=601 confirmed by LC-MS, $t_r$=18.18 min (Method Y) MH$^+$=599-603

Cpd. No. 22 tert-Butyl (S)-2-((S)-1-(2,2-Dichloro-N-(3-(3-(2,6-dichlorophenyl)isoxazol-5-yl)phenyl)acetamido)-3-methylbutan-2-ylamino)-2-oxo-1-phenylethylcarbamate. MW=735 confirmed by LC-MS, $t_r$=18.78 min (Method Y) MH$^+$=733-737

Cpd. No. 23 tert-Butyl (R)-2-((S)-1-(2,2-Dichloro-N-(3-(3-(2,6-dichlorophenyl)isoxazol-5-yl)phenyl)acetamido)-3-methylbutan-2-ylamino)-2-oxo-1-phenylethylcarbamate. MW=735 confirmed by LC-MS, $t_r$=18.67 min (Method Y) MH$^+$=733-737

Cpd. No. 24 tert-Butyl 2-((S)-1-(2,2-Dichloro-N-(3-(3-(2,6-dichlorophenyl)isoxazol-5-yl)phenyl)acetamido)-3-methylbutan-2-ylcarbamoyl)-4-hydroxypyrrolidine-1-carboxylate. MW=714 confirmed by LC-MS, $t_r$=17.89 min (Method Y) MH$^+$=712-716

Cpd. No. 25 (S)-tert-Butyl 2-(1-(2,2-Dichloro-N-(3-(3-(2,6-dichlorophenyl)isoxazol-5-yl)phenyl)acetamido)-3-methylbutan-2-ylamino)-2-oxoethyl(methyl)carbamate. MW=672 confirmed by LC-MS, $t_r$=17.98 min (Method Y) MH$^+$=670

Cpd. No. 26 (S)-tert-Butyl 4-(tert-Butoxycarbonylamino)-5-((S)-1-(2,2-dichloro-N-(3-(3-(2,6-dichlorophenyl)isoxazol-5-yl)phenyl)acetamido)-3-methylbutan-2-ylamino)-5-oxopentanoate. MW=787 confirmed by LC-MS, $t_r$=18.99 min (Method Y) MH$^+$=785-789

Cpd. No. 27 tert-Butyl (S)-1-((S)-1-(2,2-Dichloro-N-(3-(3-(2,6-dichlorophenyl)isoxazol-5-yl)phenyl)acetamido)-3-methylbutan-2-ylamino)-3-methyl-1-oxobutan-2-ylcarbamate. MW=700 confirmed by LC-MS, $t_r$=18.81 min (Method Y) MH$^+$=698-702

Cpd. No. 28 tert-Butyl (2S,3S)-1-((S)-1-(2,2-Dichloro-N-(3-(3-(2,6-dichlorophenyl)isoxazol-5-yl)phenyl)acetamido)-3-methylbutan-2-ylamino)-3-methyl-1-oxopentan-2-ylcarbamate. MW=714 confirmed by LC-MS, $t_r$=18.92 min (Method Y) MH$^+$=712-716

Cpd. No. 29 tert-Butyl (2S,3S)-1-(2-(2,2-Dichloro-N-(3-(3-(2,6-dichlorophenyl)isoxazol-5-yl)phenyl)acetamido)ethylamino)-3-methyl-1-oxopentan-2-ylcarbamate. MW=672 confirmed by LC-MS, $t_r$=17.82 min (Method Y) MH$^+$=670-674

Cpd. No. 30 (S)-tert-Butyl 1-(2-(2,2-Dichloro-N-(3-(3-(2,6-dichlorophenyl)isoxazol-5-yl)phenyl)acetamido)ethylamino)-3-methyl-1-oxobutan-2-ylcarbamate. MW=658 confirmed by LC-MS, $t_r$=17.64 min (Method Y) MH$^+$=656-660

Cpd. No. 31 tert-Butyl 2-(2-(2,2-Dichloro-N-(3-(3-(2,6-dichlorophenyl)isoxazol-5-yl)phenyl)acetamido)ethylamino)-2-oxoethyl(methyl)carbamate. MW=630 confirmed by LC-MS, $t_r$=17.59 min (Method Y) MH$^+$=628-632

Cpd. No. 32 (S)-tert-Butyl 4-(tert-Butoxycarbonylamino)-5-(2-(2,2-Dichloro-N-(3-(3-(2,6-dichlorophenyl)isoxazol-5-yl)phenyl)acetamido)ethylamino)-5-oxopentanoate. MW=744 confirmed by LC-MS, $t_r$=18.28 min (Method Y) MH$^+$=742-746

Cpd. No. 33 (2S)-tert-Butyl 2-(2-(2,2-Dichloro-N-(3-(3-(2,6-dichlorophenyl)isoxazol-5-yl)phenyl)acetamido)ethylcarbamoyl)-4-hydroxypyrrolidine-1-carboxylate. MW=672 confirmed by LC-MS, $t_r$=16.18 min (Method Y) MH$^+$=670-674

Cpd. No. 34 (2S)-N-(2-(2,2-Dichloro-N-(3-(3-(2,6-dichlorophenyl)isoxazol-5-yl)phenyl)acetamido)ethyl)-4-hydroxypyrrolidine-2-carboxamide. MW=572 confirmed by LC-MS, $t_r$=11.12 min (Method Y) MH$^+$=570-574

Cpd. No. 35 (S)-4-Amino-5-(2-(2,2-dichloro-N-(3-(3-(2,6-dichlorophenyl)isoxazol-5-yl)phenyl)acetamido)ethylamino)-5-oxopentanoic Acid. MW=588 confirmed by LC-MS, $t_r$=10.81 min (Method Y) MH$^+$=586-590

Cpd. No. 36 2,2-Dichloro-N-(3-(3-(2,6-dichlorophenyl)isoxazol-5-yl)phenyl)-N-(2-(2-(methylamino)acetamido)ethyl)acetamide. MW=530 confirmed by LC-MS, $t_r$=11.01 min (Method Y) MH$^+$=528-532

Cpd. No. 37 (S)-2-Amino-N-(2-(2,2-dichloro-N-(3-(3-(2,6-dichlorophenyl)isoxazol-5-yl)phenyl)acetamido)ethyl)-3-methylbutanamide. MW=558 confirmed by LC-MS, $t_r$=12.33 min (Method Y) MH$^+$=556-560

Cpd. No. 38 (2S,3S)-2-Amino-N-(2-(2,2-dichloro-N-(3-(3-(2,6-dichlorophenyl)isoxazol-5-yl)phenyl)acetamido)ethyl)-3-methylpentanamide. MW=572 confirmed by LC-MS, $t_r$=12.58 min (Method Y) MH$^+$=570-574

Cpd. No. 39 (S)-N-(2-Amino-3-methylbutyl)-2,2-dichloro-N-(3-(3-(2,6-dichlorophenyl)isoxazol-5-yl)phenyl)acetamide. MW=501 confirmed by LC-MS, $t_r$=11.88 min (Method Y) MH$^+$=499-503

Cpd. No. 40 N-((S)-2-((S)-2-Amino-2-phenylacetamido)-3-methylbutyl)-2,2-dichloro-N-(3-(3-(2,6-dichlorophenyl)isoxazol-5-yl)phenyl)acetamide. MW=634 confirmed by LC-MS, $t_r$=12.89 min (Method Y) MH$^+$=632-636

Cpd. No. 41 N-((S)-2-((R)-2-Amino-2-phenylacetamido)-3-methylbutyl)-2,2-dichloro-N-(3-(3-(2,6-dichlorophenyl)isoxazol-5-yl)phenyl)acetamide. MW=636 confirmed by LC-MS, $t_r$=12.84 min (Method Y) MH$^+$=634-638

Cpd. No. 42 N-((S)-1-(2,2-Dichloro-N-(3-(3-(2,6-dichlorophenyl)isoxazol-5-yl)phenyl)acetamido)-3-methylbutan-2-yl)-4-hydroxypyrrolidine-2-carboxamide. MW=614 confirmed by LC-MS, $t_r$=11.18 min (Method Y) MH$^+$=612-616

Cpd. No. 43 (S)-2,2-Dichloro-N-(3-(3-(2,6-dichlorophenyl)isoxazol-5-yl)phenyl)-N-(3-methyl-2-(2-(methylamino)acetamido)butyl)acetamide. MW=572 confirmed by LC-MS, $t_r$=11.01 min (Method Y) MH$^+$=570-574

Cpd. No. 44 (S)-4-Amino-5-((S)-1-(2,2-dichloro-N-(3-(3-(2,6-dichlorophenyl)isoxazol-5-yl)phenyl)acetamido)-3-methylbutan-2-ylamino)-5-oxopentanoic Acid. MW=630 confirmed by LC-MS, $t_r$=10.08 min (Method Y) MH$^+$=628-632

Cpd. No. 45 (S)-2-Amino-N-((S)-1-(2,2-dichloro-N-(3-(3-(2,6-dichlorophenyl)isoxazol-5-yl)phenyl)acetamido)-3-methylbutan-2-yl)-3-methylbutanamide. MW=600 confirmed by LC-MS, $t_r$=12.18 min (Method Y) MH$^+$=598-602

Cpd. No. 46 (2S,3S)-2-Amino-N-((S)-1-(2,2-dichloro-N-(3-(3-(2,6-dichlorophenyl)isoxazol-5-yl)phenyl)acetamido)-3-methylbutan-2-yl)-3-methylpentanamide. MW=614 confirmed by LC-MS, $t_r$=12.60 min (Method Y) MH$^+$=612-616

Cpd. No. 54 (E)-tert-Butyl 3-(2,2-Dichloro-N-(2-(3-(2,6-dichlorophenyl)isoxazol-5-yl)pyridin-4-yl)acetamido)acrylate. MW=543 confirmed by LC-MS, $t_r$=14.25 min (Method Y) MH$^+$=541-545

Cpd. No. 57 (2,2-Dichloro-N-(2-(3-(2,6-dichlorophenyl)isoxazol-5-yl)pyridin-4-yl)acetamido)methyl Isopropyl Carbonate. MW=533 confirmed by LC-MS, $t_r$=16.18 min (Method Y) MH$^+$=531-535

Cpd. No. 58 (R)-tert-Butyl 2-(((2,2-Dichloro-N-(2-(3-(2,6-dichlorophenyl)isoxazol-5-yl)pyridin-4-yl)acetamido)methoxy)carbonylamino)-3-methylbutanoate. MW=646 confirmed by LC-MS, $t_r$=16.08 min (Method Y) MH$^+$=644-648

Cpd. No. 61 (R)-N-(4-Amino-5-methyl-3-oxohexyl)-2,2-dichloro-N-(2-(3-(2,6-dichlorophenyl)isoxazol-5-yl)pyridin-4-yl)acetamide. MW=544 confirmed by LC-MS, $t_r$=11.92 min (Method Y) MH$^+$=542-546

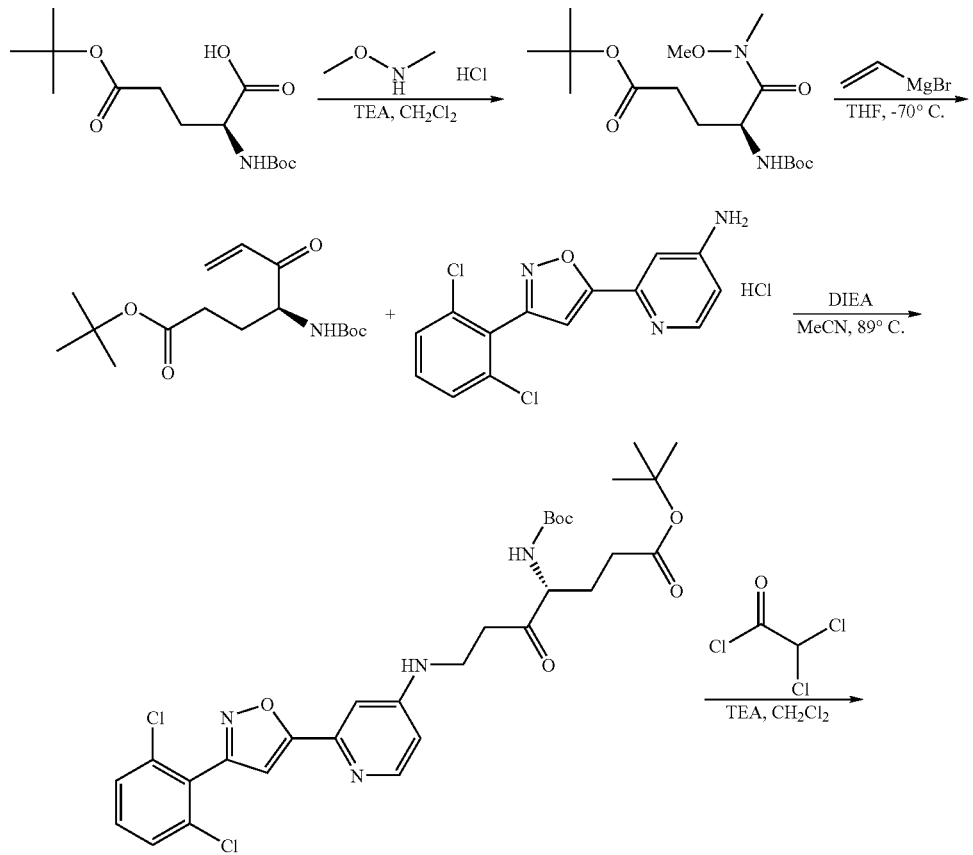

Scheme 4

-continued
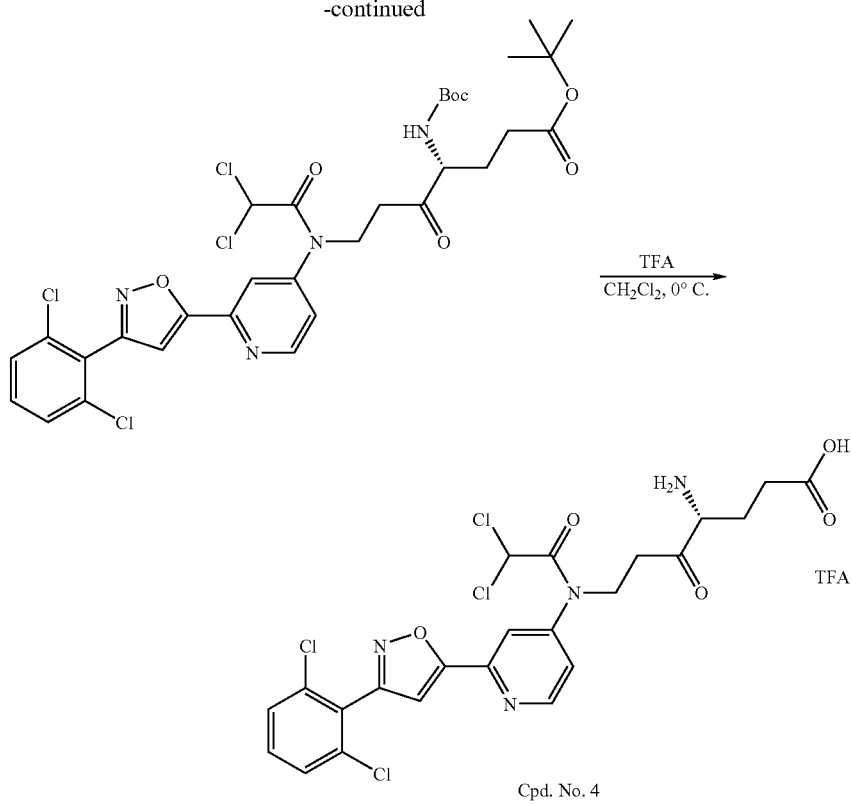
Scheme 5
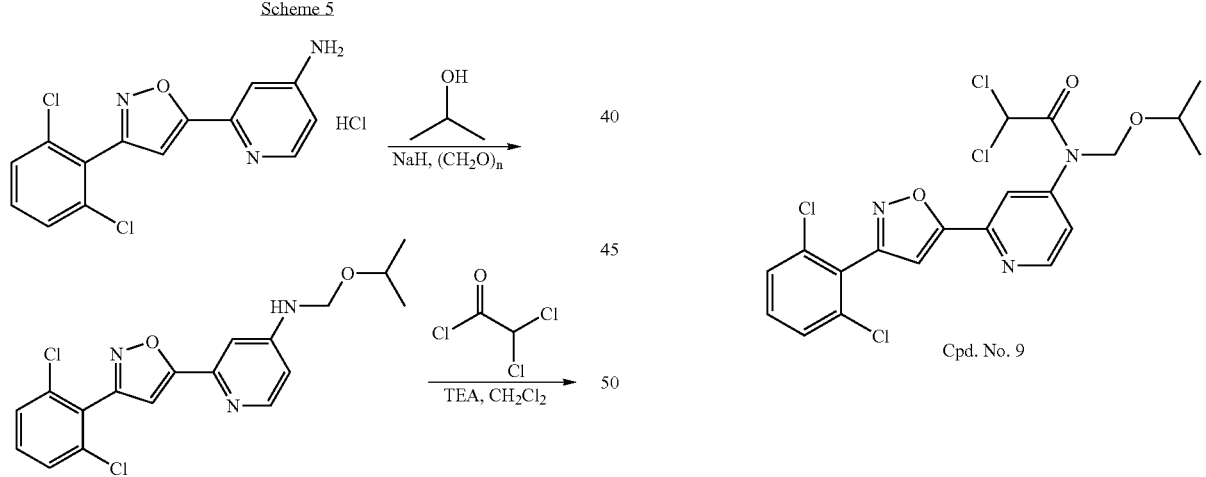
Scheme 6
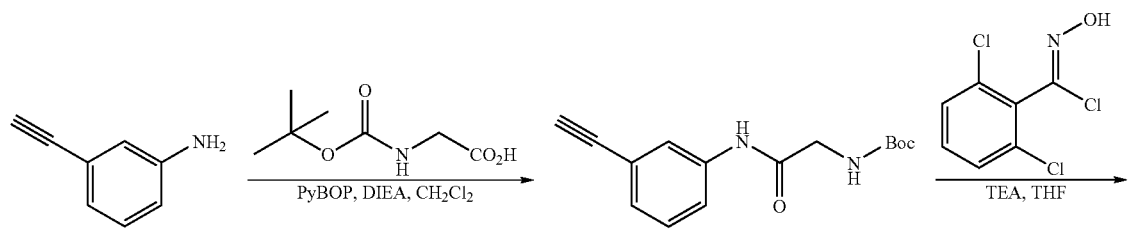

-continued
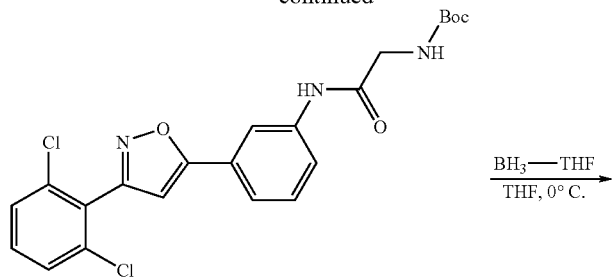
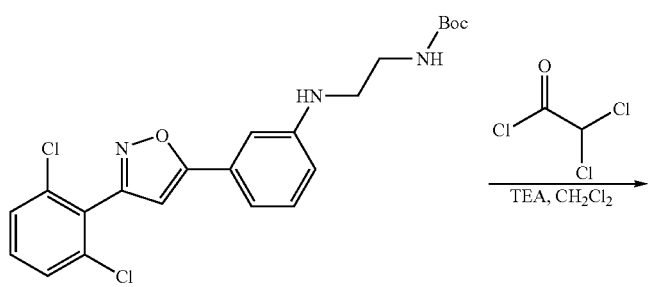
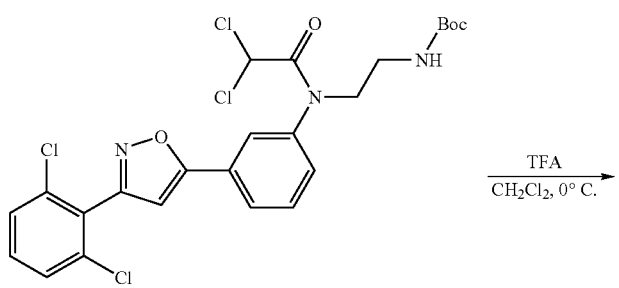
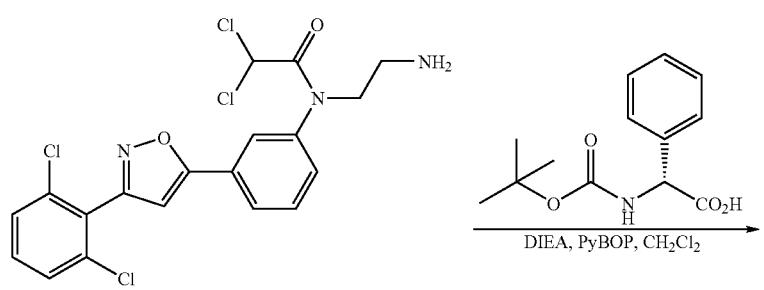
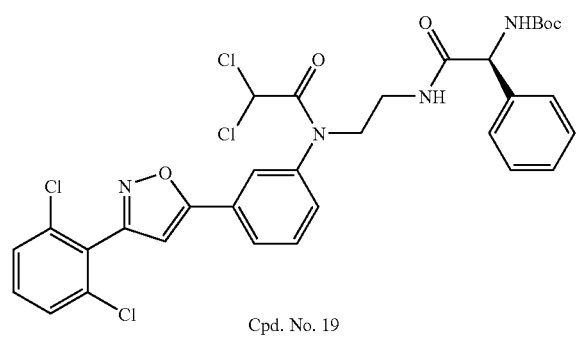
Cpd. No. 19

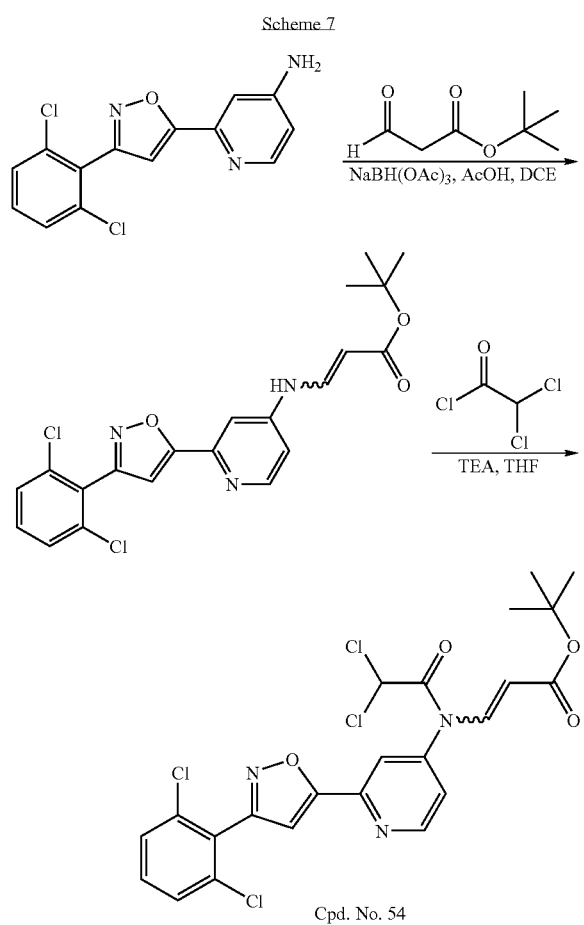
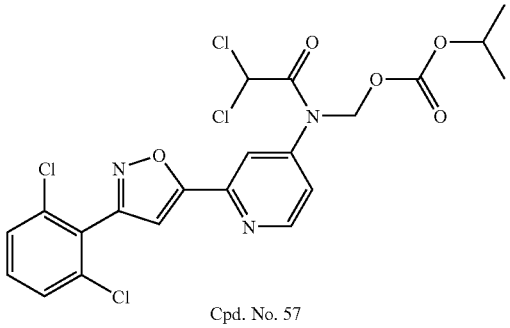
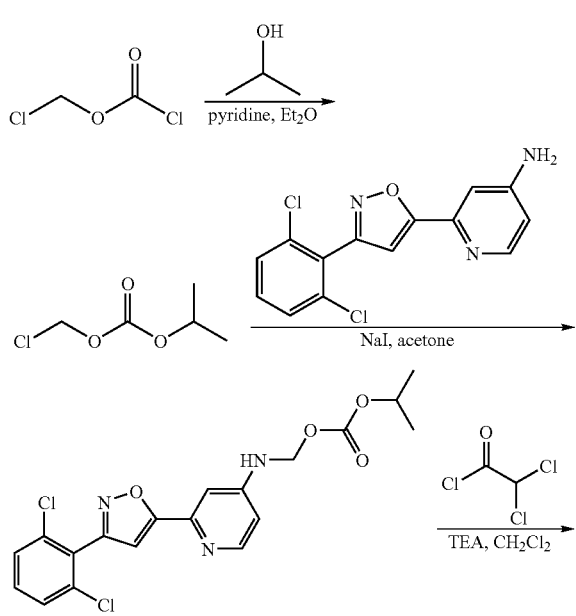

Assays for Modulation of HCV

As stated previously, the prodrugs of the invention or the metabolically active agents of the prodrug, A-B—C—NH-COCHX$_2$, are potent inhibitors of HCV replication and/or proliferation. The activity of the prodrugs of the invention, or their metabolites, can be confirmed in in vitro assays suitable for measuring inhibition of viral or retroviral replication and/or proliferation. The assays may investigate any parameter that is directly or indirectly under the influence of HCV, including, but not limited to, protein-RNA binding, translation, transcription, genome replication, protein processing, viral particle formation, infectivity, viral transduction, etc. Such assays are well-known in the art. Regardless of the parameter being investigated, in one embodiment, to examine the extent of inhibition, samples, cells, tissues, etc. comprising an HCV replicon or HCV RNA are treated with a potential inhibitory prodrug (test compound) and the value for the parameter compared to control cells (untreated or treated with a vehicle or other placebo). Control samples are assigned a relative activity value of 100%. Inhibition is achieved when the activity value of the metabolically active agent of the prodrug relative to the control is about 90%, preferably 50%, and more preferably 25-0%.

Alternatively, the extent of inhibition may be determined based upon the IC$_{50}$ of the metabolically active agent of the prodrug in the particular assay, as will be described in more detail, below.

In one embodiment, the inhibitory activity of the metabolically active agent of the prodrug can be confirmed in a replicon assay that assesses the ability of a test compound to block or inhibit HCV replication in replicon cells. One example of a suitable replicon assay is the liver cell-line Huh 7-based replicon assay described in Lohmann et al., 1999, Science 285:110-113. A specific example of this replicon assay which utilizes luciferase translation is provided in the Examples Section. In one embodiment of this assay, the amount of test prodrug that yields a 50% reduction in translation as compared to a control cell (IC$_{50}$) may be determined.

Alternatively, the inhibitory activity of the metabolically active agents of the prodrugs can be confirmed using a quantitative Western immunoblot assay utilizing antibodies specific for HCV non-structural proteins, such as NS3, NS4A NS5A and NS5B. In one embodiment of this assay, replicon cells are treated with varying concentrations of test prodrug to determine the concentration of the metabolically active agent of the test prodrug that yields a 50% reduction in the amount of a non-structural protein produced as compared to a control sample (IC$_{50}$). A single non-structural protein may be quantified or multiple non-structural proteins may be quantified.

Antibodies suitable for carrying out such immunoblot assays are available commercially (e.g., from BIODESIGN International, Saco, Me.).

Alternatively, the inhibitory activity of the metabolically active agent of the prodrugs may be confirmed in an HCV infection assay, such as the HCV infection assay described in Fournier et al., 1998, J. Gen. Virol. 79(10):2367:2374, the disclosure of which is incorporated herein by reference. In one embodiment of this assay, the amount of test prodrug that is metabolized into an active agent that yields a 50% reduction in HCV replication or proliferation as compared to a control cell ($IC_{50}$) may be determined. The extent of HCV replication may be determined by quantifying the amount of HCV RNA present in HCV infected cells. A specific method for carrying out such an assay is provided in the Examples section.

As yet another example, the inhibitory activity of the metabolically active agent of the prodrugs can be confirmed using an assay that quantifies the amount of HCV RNA transcribed in treated replicon cells using, for example, a Taqman assay (Roche Molecular, Alameda, Calif.). In one embodiment of this assay, the amount of test prodrug that is metabolized into an active agent that yields a 50% reduction in transcription of one or more HCV RNAs as compared to a control sample ($IC_{50}$) may be determined.

Regardless of the assay used, metabolically active agents of the prodrugs are generally those which exhibit $IC_{50}$s in the particular assay in the range of about 1 mM or less. Prodrugs that are metabolized into active agents which exhibit lower $IC_{50}$s, for example, in the range of about 100 μM, 10 μM, 1 μM, 100 nM, 10 nM, 1 nM, or even lower, are particularly useful for as therapeutics or prophylactics to treat or prevent HCV infections.

Prodrugs are Metabolized into Active Agents that Inhibit HCV Translation or Replication Replicon Assay The inhibitory activity of certain prodrugs of the invention, which may inhibit HCV translation or replication prior to metabolism and/or are metabolized into active agents, was confirmed using an HCV replicon assay. The HCV replicon can include such features as the HCV 5' untranslated region including the HCV IRES, the HCV 3' untranslated region, selected HCV genes encoding HCV polypeptides, selectable markers, and a reporter gene such as luciferase, GFP, etc. In the assay, actively dividing 5-2 Luc replicon-comprising cells (obtained from Ralf Bartenschlager; see Lohmann et al., 1999, Science 285:110-113) were seeded at a density of between about 5,000 and 7,500 cells/well onto 96 well plates (about 90 μl of cells per well) and incubated at 37° C. and 5% $CO_2$ for 24 hours. Then, the test prodrug (in a volume of about 10 μl) was added to the wells at various concentrations and the cells were incubated for an additional 24-48 hours before luciferase assay. The media was aspirated from each well and Bright-Glo (Promega, Madison, Wis.) luciferase assay reagents were added to each well according to the manufacturer's instructions. Briefly, the Bright-Glo reagent was diluted 1:1 with PBS and 100 μl of diluted reagent was added to each well. After 5 min of incubation at room temperature, luciferin emission was quantified with a luminometer. In this assay, the amount of test prodrug that yielded a 50% reduction in luciferase emission ($IC_{50}$) was determined. This $IC_{50}$ value may represent the antiviral activity of the prodrug itself, the activity of prodrug transformed into its active metabolized form, or a combination of the two.

Western Blot Assay

Certain prodrugs of the invention, which may inhibit HCV translation or replication prior to metabolism and/or are metabolized into active agents, were also tested for their ability to inhibit HCV replication using a quantitative Western blot analysis with antibodies specific for the HCV NS5A or other non-structural proteins. Actively dividing 9-13 replicon cells were seeded into 6-well plates at a density of $1 \times 10^5$ cells/well in a volume of 2 ml/well and incubated at 37° C. and 5% $CO_2$ for 24 hours. Various concentrations of test prodrugs (in a volume of 10 ul) were added to the wells and the cells incubated for another 48 hours. Protein samples were prepared from the cultured cells, resolved on a SDS-PAGE gel and transferred to a nitrocellulose membrane. The membrane was blocked with 5% non-fat milk in PBS for 1 hour at room temperature. Primary antibody (anti NS5A antibody; BIODESIGN International, Saco, Me.) incubation was performed for 1 hour at room temperature, after which the membrane was washed 3 times (for 15 min per time) with PBST (PBS plus 0.1% Tween 20). Horseradish peroxidase conjugated secondary antibody incubation was performed for 1 hour at room temperature and the membrane was washed 3 times (for 15 min per time) with PBST. The membrane was then soaked in substrate solution (Pierce) and exposed to a film or quantified using an imager. In this assay, the amount of test prodrug that is believed to be transformed into an active agent under the given conditions that yielded a 50% reduction in the amount of NS5A protein translated as compared to a control sample ($IC_{50}$) was determined.

The results of the Replicon assays are provided in TABLE 2. Many of the metabolically active agents of the prodrugs exhibited $IC_{50}$s in the Replicon assay in the nanomolar range.

Luciferase Counter Screen

A counter screen was used to identify non-specific inhibitors of the luciferase reporter gene. In the counter screen, a cell line carrying a construct such as a CMV-driven luciferase gene was used to identify metabolically active agents of the prodrugs that inhibit the reporter gene, and not HCV. In these CMV-Luc cells, the DNA construct, which comprises a luciferase gene downstream of a CMV promoter, is permanently integrated into the chromosome of Huh7 cells. For the counter screen, actively dividing CMV-Luc cells were seeded at a density of 5000-7500 cells/well in a volume of 90 ul/well into 96 well plate(s). The cells were then incubated at 37° C. and 5% $CO_2$ for 24 hours. Various concentrations of test prodrugs (in a volume of 10 ul) were added to the wells and the cells were incubated for 24-48 hours. Media was aspirated from each well and Bright-Glo (Pharmacia) luciferase assay reagents were added to each well according to the manufacturer's manual. Luciferin counts were taken using a luminometer.

PCR Assay

A TaqMan RT-PCR assay (Roche Molecular Systems, Pleasanton, Calif.) was used to analyze HCV RNA copy numbers, which confirmed that the viral genome of HCV is not being replicated. Actively dividing 9-13 replicon cells were seeded at a density of $3 \times 10^4$ cells/well in a volume of 1 ml/well into 24-well plates. The cells were then incubated at 37° C. and 5% $CO_2$ for 24 hours. Various concentrations of test prodrugs (in a volume of 10 ul) were added to the wells and the cells were incubated for an additional 24-48 hours. Media was removed by aspiration and RNA samples prepared from each well. TaqMan one step RT-PCR (Roche Molecular Systems, Alameda, Calif.) was performed using the freshly prepared RNA samples according to the manufacturer's manual and analyzed on an ABI Prism 7700 Sequence Detector (Applied Biosystems). The ratio of HCV RNA to cellular GAPDH RNA was used as in indication of specificity of HCV inhibition to confirm that the viral genome was not replicated.

HCV Infection Assay

The activity of a prodrug that is metabolized into an active agent can also be confirmed in an HCV infection assay. The assay can be carried out essentially as described in Fournier et al., 1998, J. Gen. Virol. 79:2367-2374. Briefly, hepatocyte cells from a doner can be plated on Day 1. On Day 3, the cells would be inoculated with HCV virus and test prodrug added. On Day 5, the medium would be changed and test prodrug would be added. On Day 7, the medium would be changed and test prodrug would be added. On Day 8, the RNA would be isolated and the HCV RNA quantified using a Taqman assay. Prodrugs that are metabolized into an active agent that exhibit an $IC_{50}$ of less than 10 μM in this assay can be identified.

Determination of Non-Toxicity of Prodrugs in Cell Culture

Prodrugs can be tested in a cytotoxicity assay with liver cells including an HCV replicon (5-2 Luc cells, 9-13 cells or Huh-7 cells). In the assay, cells can be seeded onto 96-well plates (approx. 7500 cells/well in a volume of 90 μl) and grown for 24 hr at 37° C. On day 2, various concentrations of test prodrug (in a volume of 10 μl) would be added to the wells and the cells would be grown for an additional 48 hr at 37° C. On day 3, an ATP-dependent R-Luciferase assay (Cell Titer Glo assay) would be performed to determine the number of viable cells. Prodrugs that are metabolized into an active agent exhibiting an $CC_{50}$ of greater than 10 μM would be considered as non-toxic.

Animal Studies

The safety of prodrugs can be evaluated in rats by oral, subcutaneous and intravenous administration in several experiments. Doses as high as 30 mg/kg/day can be monitored. Experimental procedures are summarized below.

In a first study the toxicity of prodrugs can be evaluated either by the subcutaneous (SC) route or the intravenous (IV via jugular cannula) route of administration in Sprague Dawley rats. Two male rats would be used in each group. A dose escalation scheme would be employed where a prodrug would be delivered IV or SC for 3 consecutive days at a dose of 10 mg/kg (study Days 1-3) in a 80%:20%—PEG/water vehicle; delivered one day IV or SC dose of 30 mg/kg (study Day 4) in 100% PEG; and an IV dose of 60 mg/kg (study Day 5) in 100% PEG. Prodrugs could be identified as being well tolerated at doses up to and including 30 mg/kg by both routes of administration.

In a second study prodrugs can be was administered by the IV route at doses of 10 and 30 mg/kg in 100% PEG. The volume administered for the 10 mg/kg dose would be 0.67 ml/kg/day and volume given the 30 mg/kg group would be 2 ml/kg/day. In addition, there would be two control groups. One control would receive 100% PEG alone at a volume of 2 ml/kg/day while the other would be an untreated sham control group. All groups (except for the untreated control with 3 male rats) would include 4 male rats each. Parameters of study would include: clinical observations, body weights, hematology, clinical chemistry, gross necropsy, organ weights, bone marrow assessment and histopathology of selected organs. Decreases in red blood cells, hemoglobin and hematocrit relative to the untreated control but not the vehicle control could be determined.

In a third study prodrugs can be compared with other compounds and administered at a dose of 10 and 30 mg/kg in 100% PEG and delivered by IV at a concentration of 1 ml/kg/day first via a jugular cannula and when the cannula failed by the lateral tail vein. A vehicle control group would receive the 100% PEG alone at the same volume. Groups would comprise 3 males and 3 females each. Before reducing the dose to 10 and 30 mg/kg two rats would receive 100 mg/kg IV at a volume of 1 ml/kg. Parameters of study would include: clinical observations, body weights, hematology, clinical chemistry, gross necropsy, organ weights and histopathology of selected organs (including injection sites).

Sustained Plasma Levels

The pharmacokinetic properties of prodrugs can be calculated in rats, monkeys and chimpanzees using the intravenous and subcutaneous routes of administration with a variety of different delivery vehicles. Sustained plasma levels can be determined with several different liposome suspension vehicles using subcutaneous administration: (i) 5 mg/ml prodrug in water with 100 mg/ml lecithin; (ii) 5 mg/ml prodrug in water with 200 mg/ml lecithin; and (iii) 5 mg/ml prodrug in water with 100 mg/ml lecithin and 5 mg/ml cholesterol. Based on these results, it is expected that other liposome formulations as are well-known in the art may be used to administer the prodrugs of the invention The prodrugs of the invention are rapidly metabolized in microsomes from rat and human livers and, in part, converted to the active compound, A-B—C—NHCOCHX$_2$. Since the active compounds are degraded rapidly by non-NADPH dependent esterases, an esterase inhibitor, bis(p-nitrophenyl) phosphate (BNPP), was used in microsomal incubations to prevent degradation of the active compound. BNPP has been shown, with a number of prodrugs, to have no effect on the disappearance rate of the prodrugs in either rat or human microsomes. Metabolism of the prodrugs occurs by NADPH dependent enzyme(s), presumably P450. Although all of the prodrugs are rapidly metabolized in liver microsomes, the amount of active compound produced varies significantly among the compounds tested. Metabolic pathways have not been extensively explored but, for many of the compounds, the absence of the deacetylation product has been confirmed using LC/MS/MS. That is, the prodrug side-chain serves to prevent esterase attack leading to inactive, deacetylation products. Loss of the alkyl side-chain seems to be the preferred metabolic pathway. Additional studies have been conducted in microsomes isolated from human jejunum. The compounds, in general, are stable in these gut microsomes.

Methods:

Incubations were conducted using cryopreserved rat and human microsomes purchased from commercial sources. Incubations were conducted at a final protein concentration of 1 mg/ml in phosphate buffer (100 mM, pH=7.4) containing 1 mM NADPH. BNPP concentrations were 1 mM in the incubation mixture. Reaction was started by addition of the compounds (5 μl of 10 μg/ml in water:DMSO; 9:1). Reactions were conducted at a volume of 100 uL in 96-well plates and reactions were quenched by addition of 50 μl of dimethyl sulfoxide containing 1% formic acid. Samples were prepared for analysis by addition of an internal standard (verapamil, 10 μl of 0.5 μM in water) and 100 μl of an organic solvent mixture (Acetonitrile:ethanol:DMSO; 2:1:1). Samples were centrifuged before analysis to remove precipitated proteins.

LC/MS/MS Analysis:

A PE/Sciex 3000 instrument was used for all analyses. Samples were injected onto a Betasil C8 column (50×3 mm; Thermo Electron Corp.) and eluted with an acetonitrile gradient. A heated nebulizer source was used as the interface between the HPLC column and the MS/MS. Quantitative analyses were conducted using the MRM mode of operation with specific parameters determined, in advance, for each compound. Standards were prepared in rat or human microsomes using the procedures outlined above and covered a range from 1-1000 ng/ml.

Pharmokinetic Studies:

Pharamcokinetic studies were conducted in rats containing surgically implanted cannula in the portal and jugular veins. Blood samples were taken simultaneously from both cannula at various times after oral administration of the compounds. In the portal vein, the prodrugs are detected and, in some cases, the active compound, A-B—C—NHCOCHX$_2$, has also been detected. The presence of active compound in the portal vein samples has been attributed to metabolism of the prodrug in transit through the gut wall. Surprisingly, the levels of inactive metabolite have been low. In the jugular samples, many, but not all, of the prodrugs have been detected in systemic circulation, depending on the hepatic extraction ratio of the prodrug. In contrast, oral administration of A-B—C—NHCOCHX$_2$ (where the "C" ring is a 2-pyridyl) results in high levels of inactive metabolite in the portal vein (attributed to esterase activity in the small intestine) and low levels of A-B—C—NHCOCHX$_2$.

Evidence for the conversion of a prodrug to its active metabolite in rat liver was obtained by measuring the prodrug and active compound concentrations in bile fluid. High levels of the prodrug and resultant A-B—C—NHCOCHX$_2$ were detected in bile fluid for a period of four hours after oral administration. In contrast, no A-B—C—NHCOCHX$_2$ was detected in bile fluid after oral administration of equivalent A-B—C—NHCOCHX$_2$. The data suggests that the prodrug accumulates in the liver and is slowly converted to the active dihaloacetamide.

Methods:

Compounds were dissolved in a mixture of TPGS:PEG:PG (35%:60%:5%) and diluted with saline for oral administration. Typically, 6.5 mg of compound was dissolved in 1 ml of the organic mixture and added to 5.5 ml of saline. Animals were dosed with 5 ml/kg of this mixture to give a typical dose of 5 mg/kg. All animal studies were conducted in male Spraque-Dawley rats and the animals were fasted overnight prior to dose administration. Surgeries (to implant blood sampling cannula) were conducted at least two days prior to the study. Blood samples (100 µl) were collected using sodium heparin as anticoagulant and added to 300 µl of a mixture of acetate buffer (100 mM, pH=6.5):acetonitrile:ethanol:DMSO (2:1:1:2 v/v). Samples were centrifuged and the supernatant was analyzed by LC/MS/MS using the procedures outlined above. Standards were prepared similarly using fresh rat blood from naive animals.

The results of the Replicon assays are provided in TABLE 2. In TABLE 2, a value of "+++" means less than 1 µM; ++ means between 1 and 20 µM; + means greater than 20 µM.

TABLE 2

| Cpd. No. | Assay | Result Value |
|---|---|---|
| 1 | HEPC_REPLICON-ICWESTERN | ++ |
|   | HEPC_REPLICON-LUC | + |
| 2 | HEPC_REPLICON-ICWESTERN | + |
|   | HEPC_REPLICON-LUC | + |
| 3 | HEPC_REPLICON-ICWESTERN | +++; +++ |
|   | HEPC_REPLICON-LUC | +++; +++ |
| 4 | HEPC_REPLICON-ICWESTERN | +++ |
| 5 | HEPC_REPLICON-ICWESTERN | +++ |
|   | HEPC_REPLICON-LUC | +++ |
| 6 | HEPC_REPLICON-ICWESTERN | +++ |
|   | HEPC_REPLICON-LUC | +++ |
| 7 | HEPC_REPLICON-ICWESTERN | +++ |
|   | HEPC_REPLICON-LUC | ++ |
| 8 | HEPC_REPLICON-ICWESTERN | ++ |
| 9 | HEPC_REPLICON-LUC | + |
| 10 | HEPC_REPLICON-ICWESTERN | ++ |
| 11 | HEPC_REPLICON-ICWESTERN | +++ |
| 12 | HEPC_REPLICON-ICWESTERN | + |
| 13 | HEPC_REPLICON-ICWESTERN | + |
| 14 | HEPC_REPLICON-ICWESTERN | + |
| 16 | HEPC_REPLICON-ICWESTERN | ++ |
|   | HEPC_REPLICON-LUC | ++ |
| 17 | HEPC_REPLICON-ICWESTERN | + |
| 18 | HEPC_REPLICON-ICWESTERN | + |
| 19 | HEPC_REPLICON-ICWESTERN | + |
| 20 | HEPC_REPLICON-ICWESTERN | ++ |
| 21 | HEPC_REPLICON-ICWESTERN | ++ |
| 22 | HEPC_REPLICON-ICWESTERN | ++ |
| 23 | HEPC_REPLICON-ICWESTERN | ++ |
| 24 | HEPC_REPLICON-ICWESTERN | ++ |
| 25 | HEPC_REPLICON-ICWESTERN | ++ |
| 26 | HEPC_REPLICON-ICWESTERN | ++ |
| 27 | HEPC_REPLICON-LUC | + |
| 28 | HEPC_REPLICON-LUC | + |
| 29 | HEPC_REPLICON-LUC | + |
| 30 | HEPC_REPLICON-LUC | + |
| 32 | HEPC_REPLICON-ICWESTERN | + |
| 33 | HEPC_REPLICON-ICWESTERN | + |
| 34 | HEPC_REPLICON-ICWESTERN | + |
| 35 | HEPC_REPLICON-ICWESTERN | + |
| 36 | HEPC_REPLICON-ICWESTERN | ++ |
| 37 | HEPC_REPLICON-ICWESTERN | ++ |
| 38 | HEPC_REPLICON-ICWESTERN | ++ |
| 39 | HEPC_REPLICON-ICWESTERN | ++ |
| 40 | HEPC_REPLICON-ICWESTERN | + |
| 41 | HEPC_REPLICON-ICWESTERN | + |
| 42 | HEPC_REPLICON-ICWESTERN | + |
| 43 | HEPC_REPLICON-ICWESTERN | ++ |
| 47 | HEPC_REPLICON-ICWESTERN | +++ |
|   | HEPC_REPLICON-LUC | +++ |
| 48 | HEPC_REPLICON-ICWESTERN | +++ |
|   | HEPC_REPLICON-LUC | +++ |
| 49 | HEPC_REPLICON-ICWESTERN | +++ |
|   | HEPC_REPLICON-LUC | +++ |
| 50 | HEPC_REPLICON-ICWESTERN | +++ |
|   | HEPC_REPLICON-LUC | +++ |
| 51 | HEPC_REPLICON-ICWESTERN | +++ |
|   | HEPC_REPLICON-LUC | +++ |
| 52 | HEPC_REPLICON-ICWESTERN | +++ |
|   | HEPC_REPLICON-LUC | +++ |
| 53 | HEPC_REPLICON-ICWESTERN | +++ |
|   | HEPC_REPLICON-LUC | +++ |
| 54 | HEPC_REPLICON-ICWESTERN | ++ |
|   | HEPC_REPLICON-ICWESTERN | +++ |
|   | HEPC_REPLICON-LUC | +++ |
| 55 | HEPC_REPLICON-ICWESTERN | ++ |
|   | HEPC_REPLICON-LUC | +++ |
| 57 | HEPC_REPLICON-ICWESTERN | ++ |
|   | HEPC_REPLICON-LUC | ++ |
| 58 | HEPC_REPLICON-ICWESTERN | ++ |
|   | HEPC_REPLICON-LUC | + |
| 59 | HEPC_REPLICON-ICWESTERN | +++ |
|   | HEPC_REPLICON-LUC | +++ |
| 60 | HEPC_REPLICON-ICWESTERN | ++ |
|   | HEPC_REPLICON-LUC | +++ |
| 61 | HEPC_REPLICON-LUC | +++ |

Stabilization of Parent Compound Using a Prodrug Strategy

The parent compound, 64, is cleaved by esterase enzymes to an inactive metabolite, 66, in a reaction that does not require NADPH as a cofactor. Because esterases are present in the gut, the active parent compound is extensively hydrolyzed during the absorption process. Alkylation of the acetyl nitrogen, to provide prodrugs 65, stabilizes the parent compound against direct attack by esterases. Parent compounds stabilized by alkylation remain essentially 100% unhydrolyzed for at least 60 minutes after administration to human microsomes in the absence of NADPH. If NADPH is added to the microsomal incubation, conversion to the parent compound occurs through CYP P450 enzyme activity. Prodrugs are stabilized against breakdown in the gut and are metabolized in the liver within 60 minutes in the presence of NADPH.

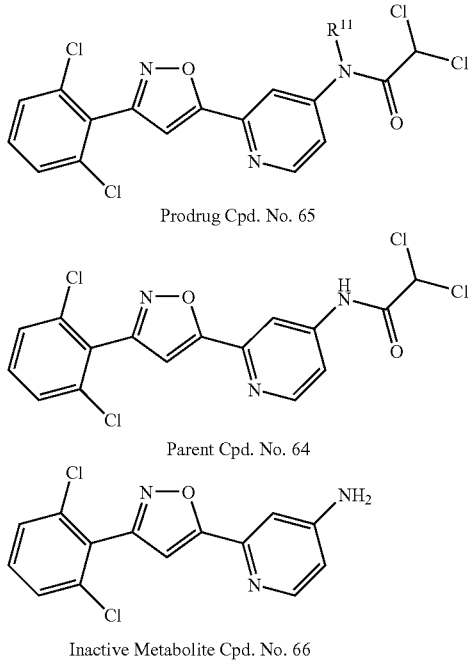

Prodrug Cpd. No. 65

Parent Cpd. No. 64

Inactive Metabolite Cpd. No. 66

Oral Administration of the Parent Compound—Hydrolysis in Rats

Figure 1B:
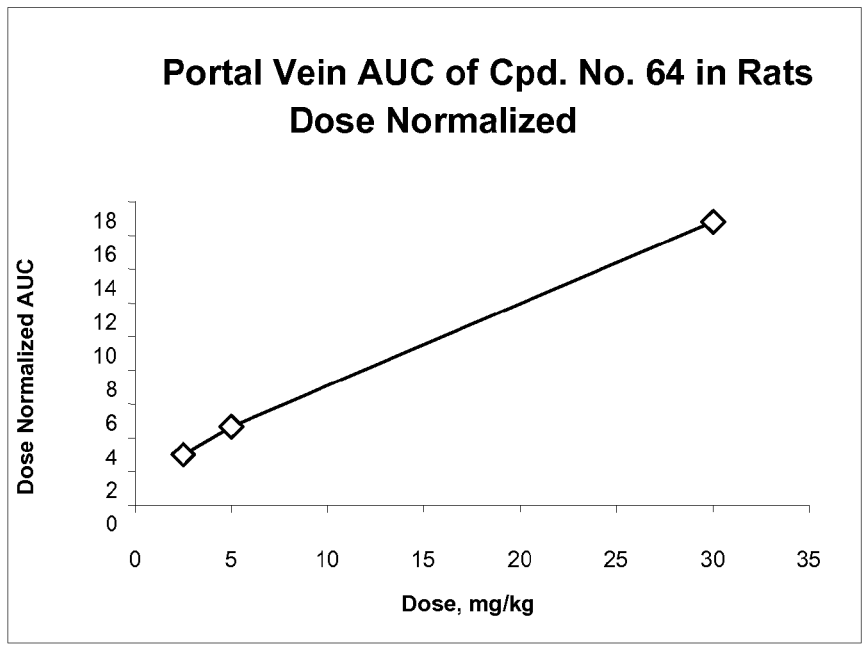

Administered orally, the parent compound is well absorbed but is extensively hydrolyzed to the inactive metabolite as demonstrated in this experiment in which plasma samples were taken from the portal vein of rats and analyzed for Cpd. No. 66 and Cpd. No. 64 (Table 3). However, a portion of the active parent compound remains intact and the active parent compound concentrations increase in a linear fashion with dose (FIGS. 1A and 1B). Because the portal blood flows directly to the liver, the intact active parent compound may exert an anti-viral effect in the liver.

TABLE 3

| Dose (mg/kg) | Ratio (Cpd. 66/Cpd. 64) |
| --- | --- |
| 2.5 | 29 |
| 5 | 88 |
| 30 | 24 |

Metabolism of Prodrugs in Liver Microsomes—Production of Actives

Figure 2A:
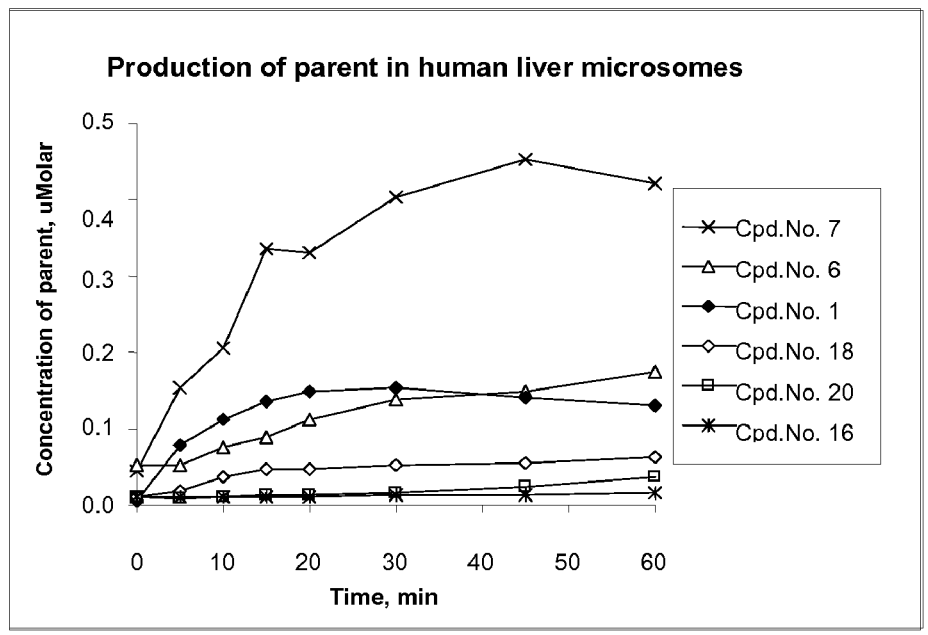
FIGS. 2A and 2B show the production of parent from prodrugs in human and rat liver microsomes. Starting concentration of prodrug was 1 micromolar.
Figure 2B:
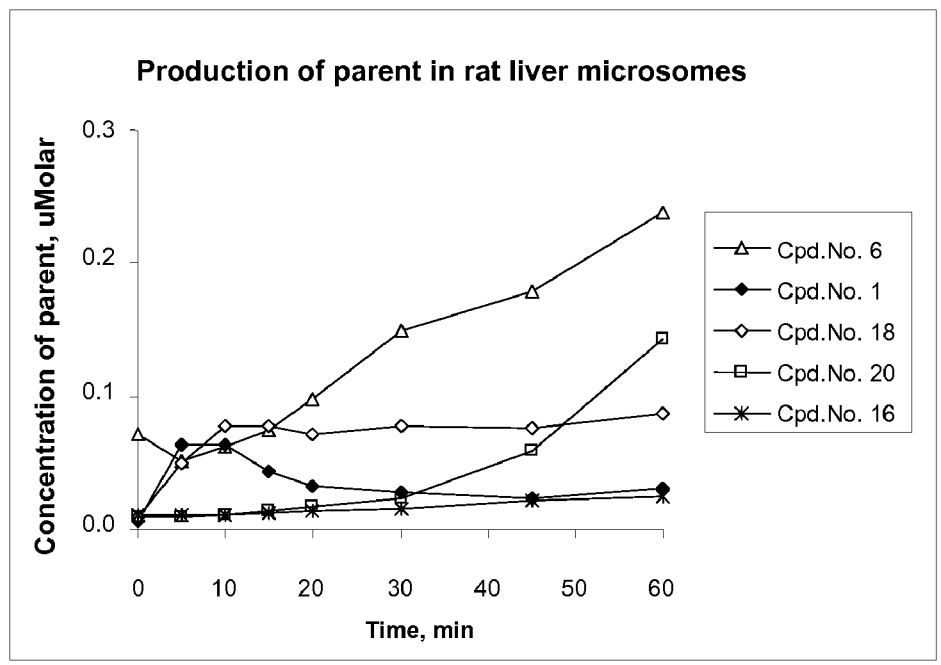

Hydrolysis of the prodrugs to parent compounds was observed in human and rat liver microsomes for many of the prodrugs (FIGS. 2A and 2B). These studies were carried out using commercially available, cryopreserved microsomes and incubations were performed in the presence of bis-nitrophenyl phosphate, an esterase inhibitor, to prevent hydrolysis of the dichloroacetyl group of the parent.

Figure 3A:
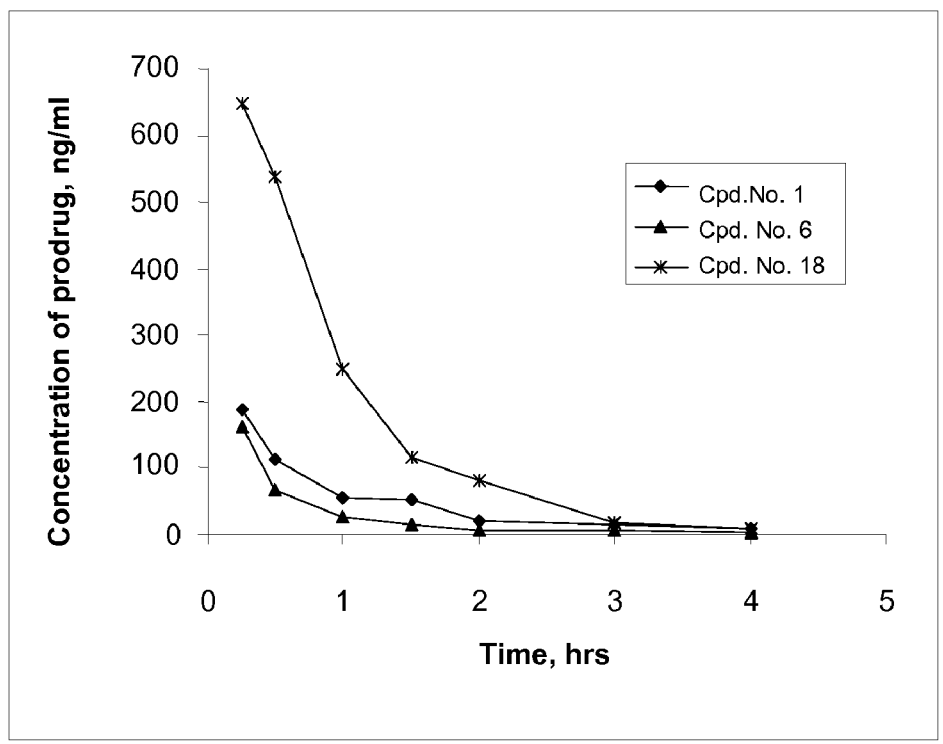
FIGS. 3A and 3B show the pharmacokinetic profiles for prodrugs and inactive metabolites following oral administration of 5 mg/kg prodrug.
Figure 3B:
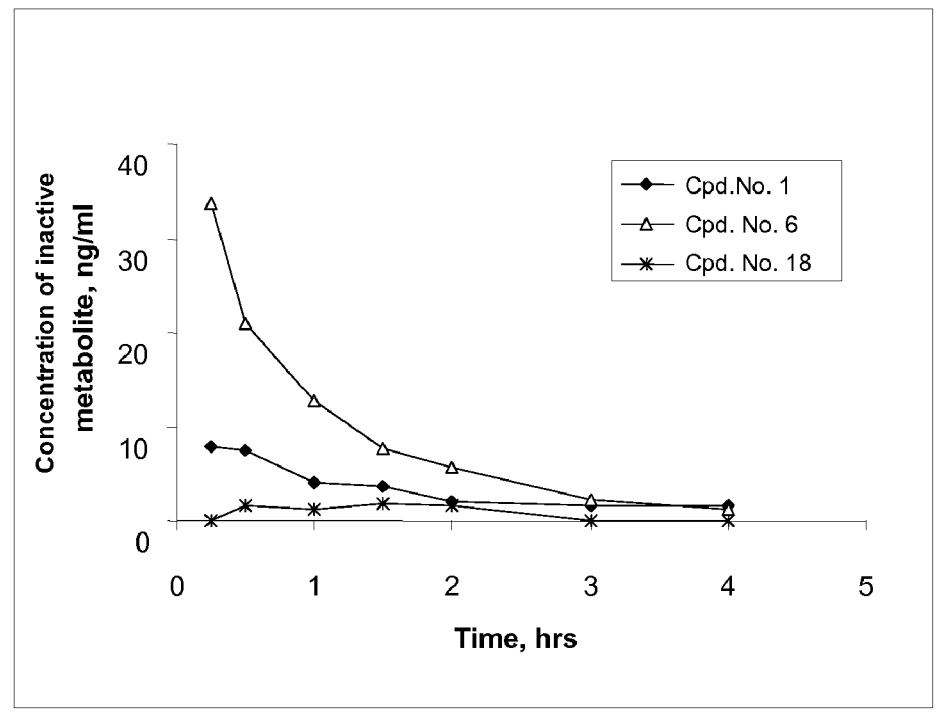

Pharmacokinetics of Prodrugs in Rats—Gut Hydrolysis of Prodrugs and Metabolism of the Parent Compound to the Inactive Metabolite Prodrugs are stable to gut esterases and are absorbed intact—concentrations of inactive metabolite in the portal vein are relatively low relative to prodrug concentrations (FIGS. 3A and 3B). TABLE 4 summarizes the AUC of prodrugs, parent and inactive metabolites in the portal vein following a 5 mg/kg oral dose of prodrug. TABLE 4 shows the AUC values for prodrug, parent and inactive metabolites in the portal vein of rats following a 5 mg/kg oral dose.

TABLE 4

| | AUC in the portal vein, ng * hr/ml | | |
| --- | --- | --- | --- |
| Prodrug administered | Prodrug | parent | inactive metabolite |
| Cpd. No. 1 | 176 | 1.74 | 12.5 |
| Cpd. No. 6 | 98.3 | 1.57 | 33.6 |
| Cpd. No. 18 | 627 | 3.43 | 2.51 |

Figure 4A:
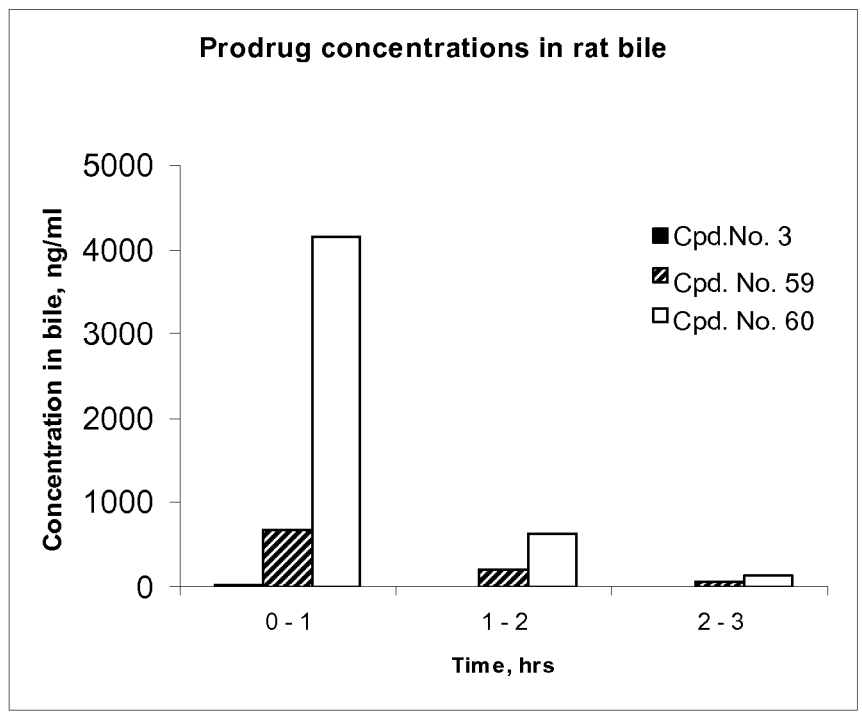
FIGS. 4A and 4B show the prodrug levels in the bile of rats.
Figure 4B:
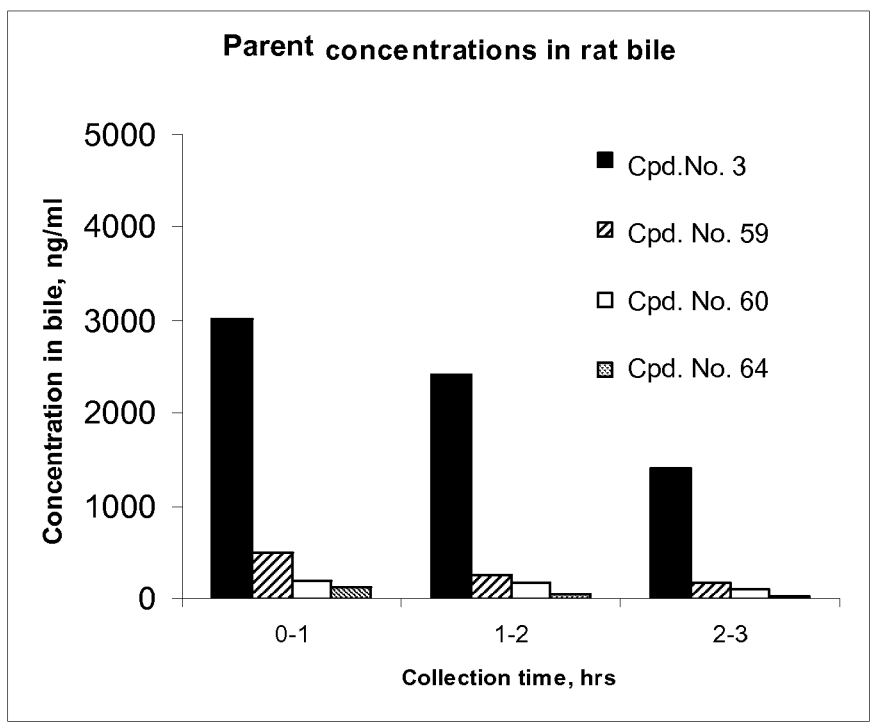

Biliary Excretion of the Parent Compound and the Inactive Metabolite Following Oral Administration of Prodrugs to Rats Prodrugs were administered to rats at a dose of 5 mg/kg and bile was collected for three hours in one hour intervals. The data indicates that the prodrugs were extracted by the liver and converted into the parent compound (FIGS. 4A and 4B). The concentrations of the parent compound in the bile were substantially higher for a 5 mg/kg dose of prodrug than for a 30 mg/kg dose of the parent compound.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. A compound according to structural formula

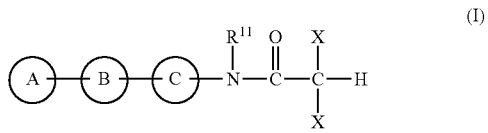

(I)

or a pharmaceutically acceptable salt, or N-oxide thereof, wherein

A is a phenyl or six-membered heteroaryl ring having from one to five of the same or different $R^{20}$ substituents, provided that at least one of the substituents is positioned ortho to ring B;

B is a heteroaryl having from one to three annular heteroatoms selected from N, O, and S, where the A and C moieties are attached to non-adjacent ring atoms of B, provided that when the B includes more than one annular oxygen atom, the oxygen atoms are not adjacent;

C is a phenyl or a heteroaryl ring, wherein when C is phenyl, it is substituted relative to the B moiety at the meta position with the —N($R^{11}$)—C(O)—$CX_2$—H, or when C is a heteroaryl group, the B moiety and the —N($R^{11}$)—C(O)—$CX_2$—H moiety are positioned on C with only one ring atom of C between them;

$R^{11}$ is selected from the group consisting of —$C_1$-$C_6$ alkyl-C(O)—$OR^9$, —$C_2$-$C_6$ alkenyl-C(O)—O-$R^9$, and —$(CHR^{10})_n$-J;

each X is independently —H or halo, provided both X are not H;

n is 0, 1, 2, 3 or 4;

$R^9$ is —H, $C_1$-$C_6$ alkyl, aryl, arylalkyl, heteroaryl or heteroaralkyl;

each $R^{10}$ is independently —H or lower alkyl;

J is selected from the group consisting of —O—C(O)—O—$R^9$, —O—C(O)—N(H)—CH($R^{13}$)—C(O)—O—$R^9$, —OH, —O($C_1$-$C_6$ alkyl), —P(O)(O$R^{18}$)O$R^{19}$, —C(=O)—(CH$_2$)$_{0-3}$CH($R^{13}$)—$R^{14}$, —C(=O)—CH($R^{13}$)—NH—C(O)—$R^{14}$, —C(=O)—O$R^9$, —N(H)—C(O)—$R^{21}$, and —N(H)—C(O)—(CH($R^{22}$))$_{1-3}$—N($R^{13}$)—$R^{21}$;

$R^{13}$ is selected from the group consisting of —H, —NH$_2$ and $C_1$-$C_6$ alkyl;

$R^{14}$ is selected from the group consisting of —H, —NH$_2$, $C_1$-$C_6$ alkyl, —$C_0$-$C_6$ alkyl-C(O)—O$R^9$, —P(O)(O$R^{18}$)O$R^{19}$ and —CH($R^{15}$)—N(H)—$R^{21}$;

$R^{15}$ is selected from the group consisting of —H, $C_1$-$C_6$ alkyl, and —$C_1$-$C_6$ alkyl-C(O)—O$R^9$; or $R^{15}$ together with the carbon atom to which it is attached and the nitrogen atom adjacent to the carbon atom form a cycloheteroalkyl group optionally substituted with —OH;

$R^{18}$ is —H, lower alkyl, aryl or arylalkyl;

$R^{19}$ is —H, lower alkyl, aryl or arylalkyl;

$R^{21}$ is selected from the group consisting of —H, $C_1$-$C_6$ alkyl, —O—$R^9$ and —C(O)—O—$R^9$;

$R^{22}$ is selected from the group consisting of —H, aryl, $C_1$-$C_6$ alkyl, —$C_1$-$C_6$ alkyl-C(O)—O$R^9$; or $R^{22}$ together with the carbon to which it is attached and $R^{13}$ together with the nitrogen to which it is attached form a cycloheteroalkyl group optionally substituted with —OH; and each $R^{20}$ is, independently of the other, selected from the group consisting of —OH, —SH, —CN, —C(O)H, —NO$_2$, halo, fluoro, chloro, bromo, iodo, lower alkyl, substituted lower alkyl, lower heteroalkyl, substituted lower heteroalkyl, cycloalkyl, substituted cycloalkyl, cycloheteroalkyl, substituted cycloheteroalkyl, lower haloalkyl, monohalomethyl, dihalomethyl, trihalomethyl, trifluoromethyl, lower alkylthio, substituted lower alkylthio, lower alkoxy, substituted lower alkoxy, methoxy, substituted methoxy, lower heteroalkoxy, substituted lower heteroalkoxy, cycloalkoxy, substituted cycloalkoxy, cycloheteroalkoxy, substituted cycloheteroalkoxy, lower haloalkoxy, monohalomethoxy, dihalomethoxy, trihalomethoxy, trifluoromethoxy, amino, lower di- or monoalkylamino, substituted lower di- or monoalkylamino, aryl, substituted aryl, aryloxy, substituted aryloxy, phenoxy, substituted phenoxy, arylalkyl, substituted arylalkyl, arylalkyloxy, substituted arylalkyloxy, benzyl, benzyloxy, heteroaryl, substituted heteroaryl, heteroaryloxy, substituted heteroaryloxy, heteroarylalkyl, substituted heteroarylalkyl, heteroarylalkyloxy, substituted heteroarylalkyloxy, carboxyl, lower alkoxycarbonyl, substituted lower alkoxycarbonyl, aryloxycarbonyl, substituted aryloxycarbonyl, arylalkyloxycarbonyl, substituted arylalkyloxycarbonyl, carbamate, substituted carbamate, carbamoyl, substituted carbamoyl, thiocarbamoyl, substituted thiocarbamoyl, ureas, substituted ureas, thioureas, substituted thioureas, sulfamoyl, substituted sulfamoyl and a group of the formula -L-$R^8$, where "L" is a linker and $R^8$ is cycloalkyl, substituted cycloalkyl, cycloheteroalkyl or substituted cycloheteroalkyl.

2. The compound according to claim 1, wherein

A is a phenyl substituted with at least two $R^{20}$ groups selected from the group consisting of halo, lower alkoxy, lower alkyl, lower haloalkyl, wherein at least one of the $R^{20}$ is positioned ortho to ring B;

B is a heteroaryl ring having two annular heteroatoms selected from N and O, where the A and C moieties are attached to non-adjacent ring atoms of B;

C is a phenyl substituted relative to the B moiety at the meta position with the —N($R^{11}$)—C(O)—C$X_2$—H;

$R^{11}$ is —(CH$R^{10}$)$_n$-J;

each X is halo;

n is 1 or 2;

$R^9$ is —H or $C_1$-$C_6$ alkyl;

each $R^{10}$ is independently —H or lower alkyl;

J is selected from the group consisting of —O—$R^9$, —P(O)(O$R^{18}$)O$R^{19}$, —C(=O)—O$R^9$, —N(H)—C(O)—$R^{21}$, and —N(H)—C(O)—(CH($R^{22}$))$_{1-3}$—N($R^{13}$)—$R^{21}$;

$R^{13}$ is selected from the group consisting of —H, and $C_1$-$C_6$ alkyl;

$R^{18}$ is —H or lower alkyl;

$R^{19}$ is —H or lower alkyl;

$R^{21}$ is selected from the group consisting of —H, $C_1$-$C_6$ alkyl, —O—$R^9$, and —C(O)—O—$R^9$;

$R^{22}$ is selected from the group consisting of —H, aryl, $C_1$-$C_6$ alkyl, and —$C_1$-$C_6$ alkyl-C(O)—O$R^9$; and $R^{22}$ together with the carbon to which it is attached and $R^{13}$ together with the nitrogen to which it is attached form a cycloheteroalkyl group optionally substituted with —OH.

3. The compound according to claim 2, of formula

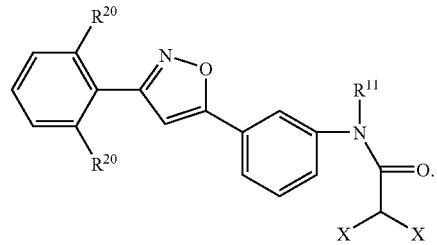

4. The compound according to claim 3, wherein X is chloro.

5. The compound according to claim 4, wherein one $R^{20}$ is halo and the other $R^{20}$ is lower alkoxy, or lower haloalkyl.

6. The compound according to claim 5, wherein both $R^{20}$ are halo.

7. The compound according to claim 6, wherein both $R^{20}$ are chloro.

8. The compound according to claim 3 or a pharmaceutically acceptable salt, or N-oxide thereof, wherein $R^{11}$ is selected from the group consisting of:

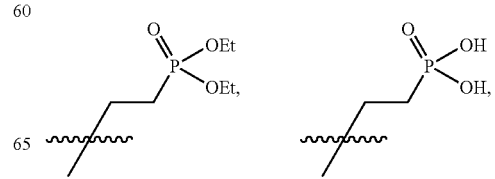

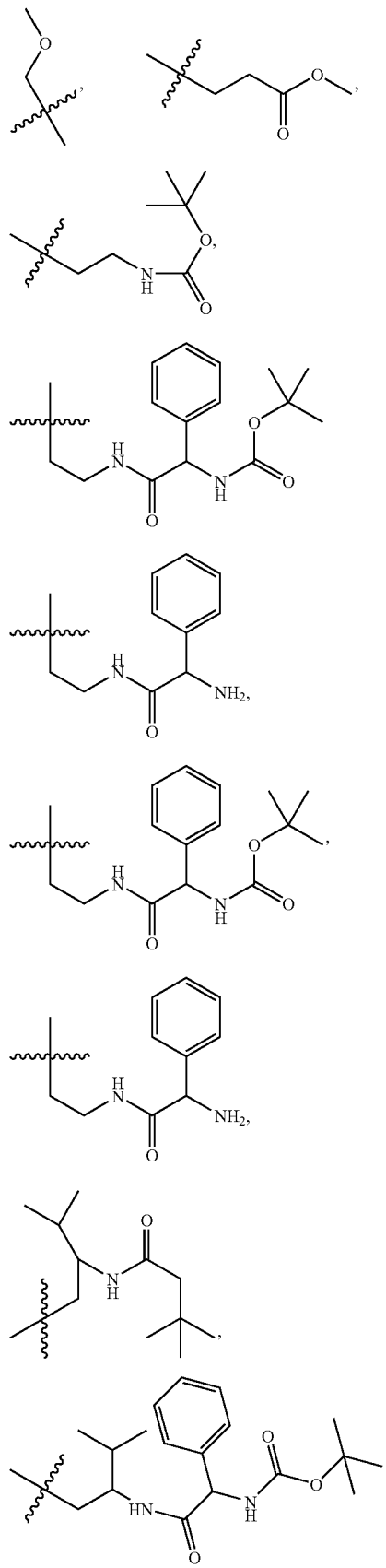
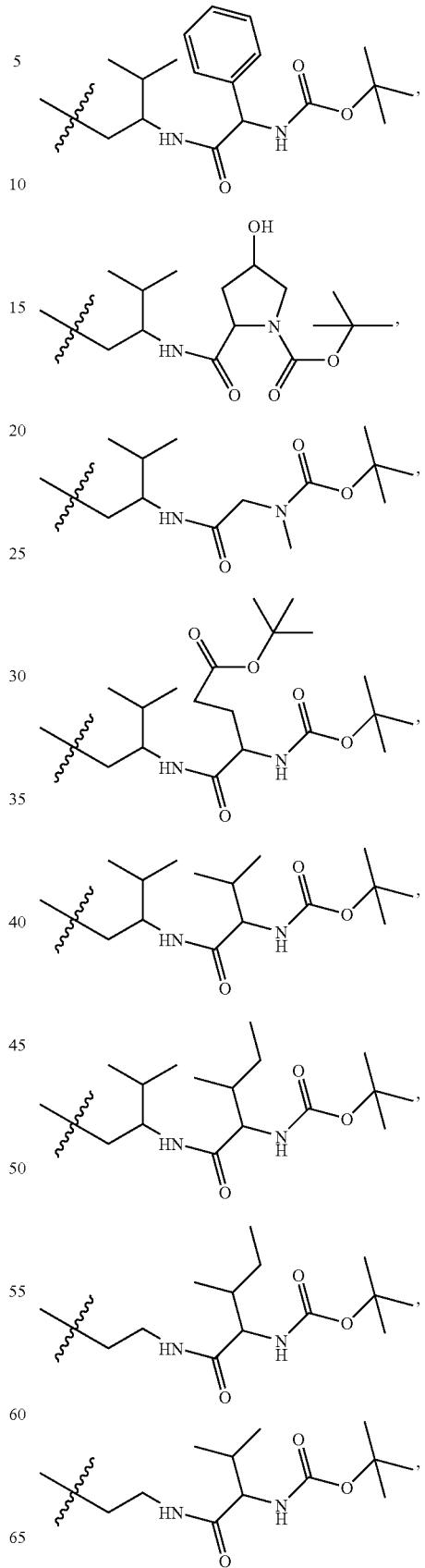

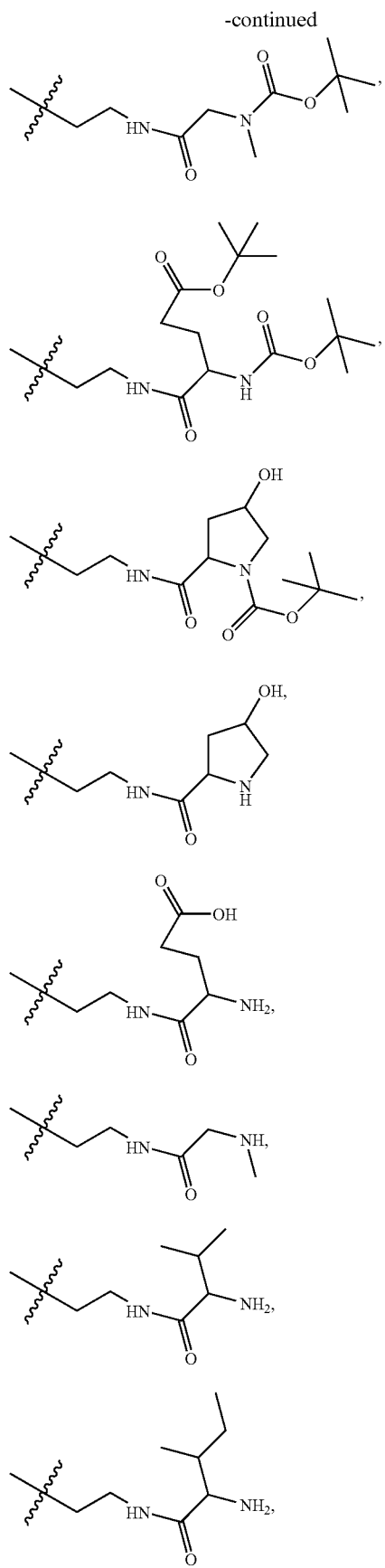
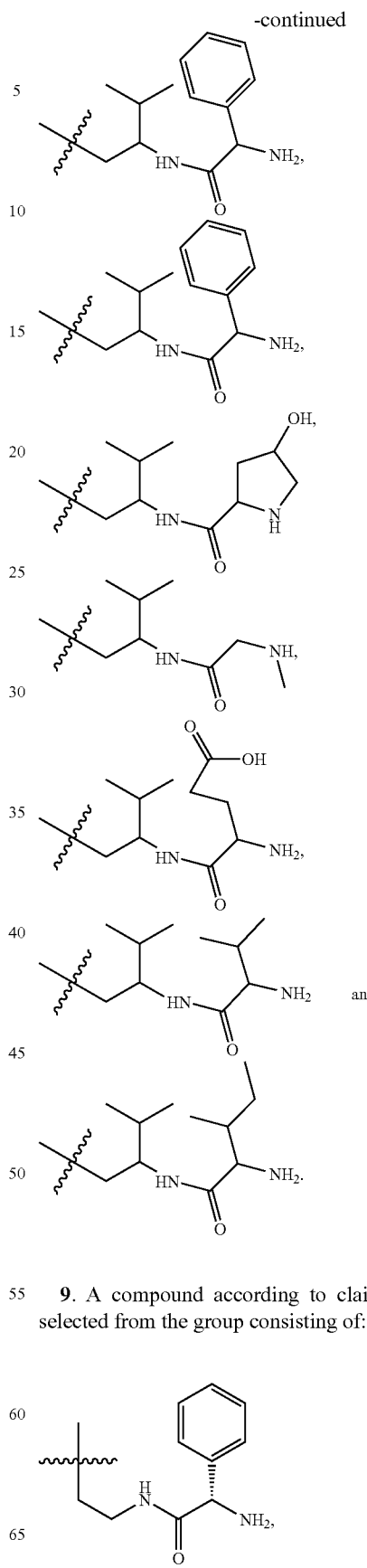
9. A compound according to claim 8, wherein $R^{11}$ is selected from the group consisting of:
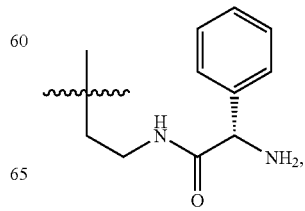

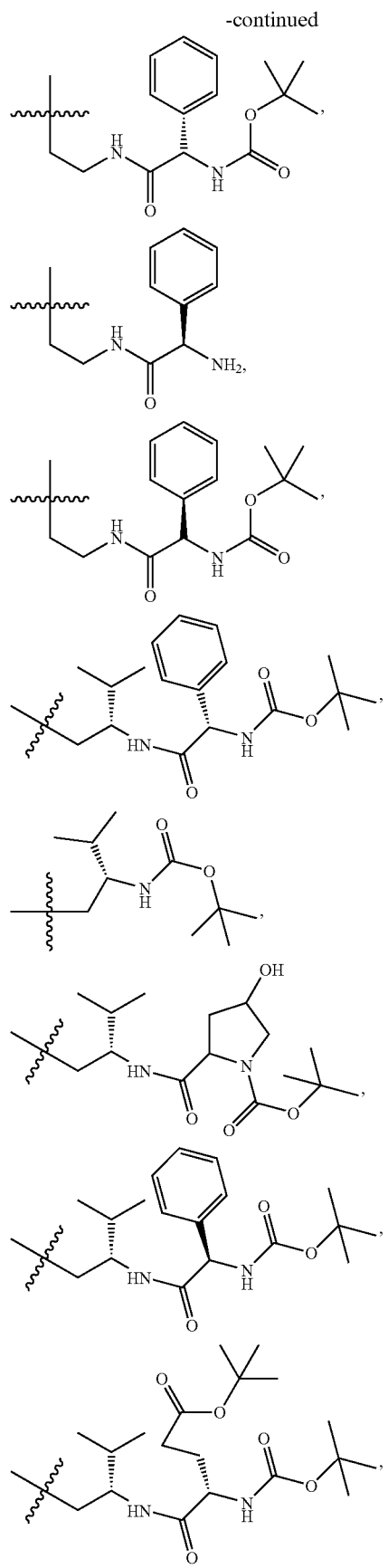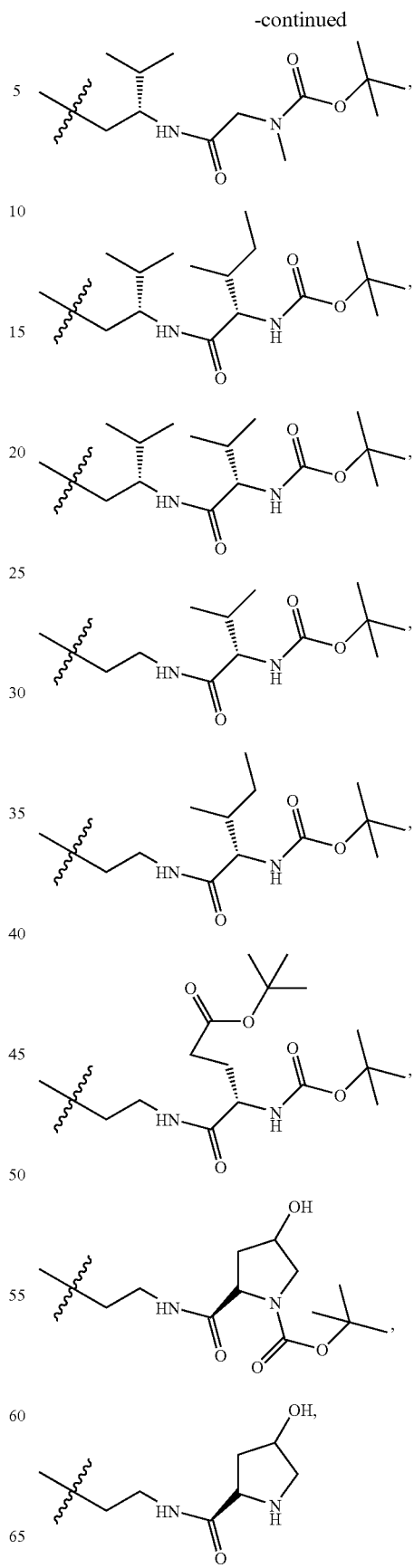

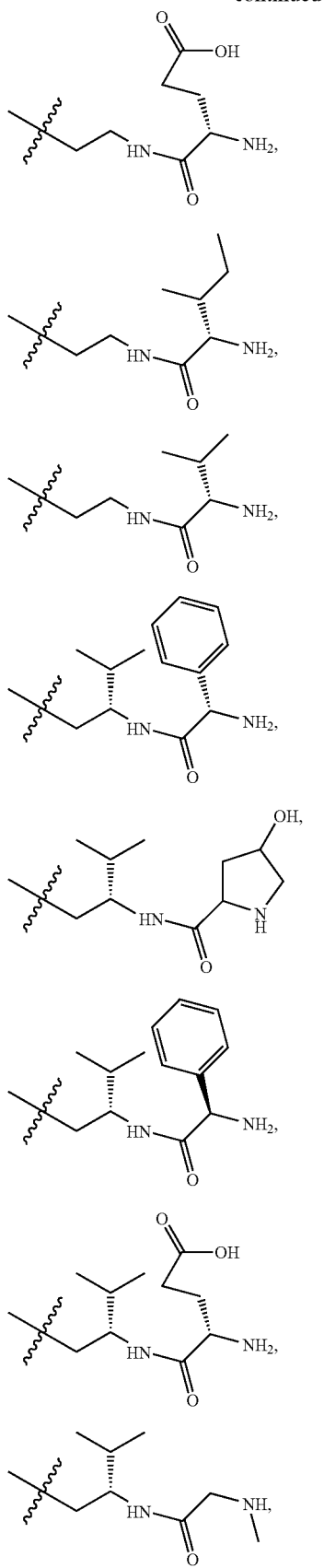

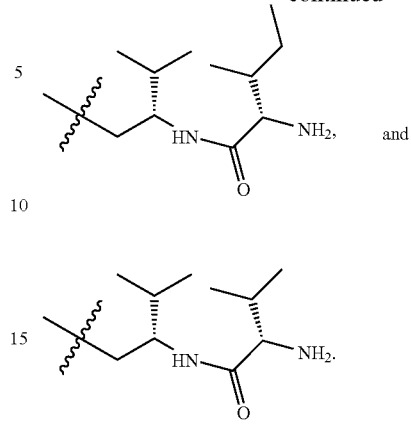

10. The compound according to claim 1, wherein

A is a phenyl substituted with at least two $R^{20}$ groups selected from the group consisting of halo, lower alkoxy, lower alkyl, lower haloalkyl, wherein at least one of the $R^{20}$ is positioned ortho to ring B;

B is a heteroaryl ring having two annular heteroatoms selected from N and O, where the A and C moieties are attached to non-adjacent ring atoms of B;

C is a pyridinyl wherein the B moiety and the —N($R^{11}$)—C(O)—CX$_2$—H moiety are positioned on C with only one ring atom of C between them;

$R^{11}$ is selected from the group consisting of —C$_2$-C$_6$ alkenyl-C(O)—O—R$^9$, and —(CHR$^{10}$)$_n$-J;

each X is halo;

n is 1 or 2;

$R_9$ is —H or C$_1$-C$_6$ alkyl;

$R^{10}$ is hydrogen;

J is selected from the group consisting of —O—C(O)—O—R$^9$, —O—C(O)—N(H)—CH(R$^{13}$)—C(O)—O—R$^9$, —O—R$^9$, —C(=O)—(CH$_2$)$_{0-3}$CH(R$^{13}$)—R$^{14}$, —C(=O)—CH(R$^{13}$)—NH—C(O)—R$^{14}$ and —C(=O)—OR$^9$;

$R^{13}$ is selected from the group consisting of —H, —NH$_2$ and C$_1$-C$_6$ alkyl;

$R^{14}$ is selected from the group consisting of —NH$_2$, C$_1$-C$_6$ alkyl, —C$_0$-C$_6$ alkyl-C(O)—OR$^9$, —P(O)(OR$^{18}$)OR$^{19}$ and —CH(R$^{15}$)—N(H)—R$^{21}$;

$R^{15}$ is selected from the group consisting of —H, C$_1$-C$_6$ alkyl, and —C$_1$-C$_6$ alkyl-C(O)—OR$^9$; or $R^{15}$ together with the carbon atom to which it is attached and the nitrogen atom adjacent to the carbon atom form a cycloheteroalkyl group optionally substituted with —OH;

$R^{18}$ is lower alkyl;

$R^{19}$ is lower alkyl; and $R^{21}$ is selected from the group consisting of —H, —O—R$^9$ and —C(O)—O—R$^9$.

11. The compound according to claim 10, of formula

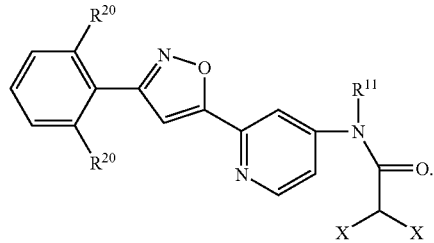

12. The compound according to claim 11, wherein X is chloro.

13. The compound according to claim 12, wherein one $R^{20}$ is halo and the other $R^{20}$ is lower alkoxy, or lower haloalkyl.

14. The compound according to claim 13, wherein both $R^{20}$ are halo.

15. The compound according to claim 14, wherein both $R^{20}$ are chloro.

16. The compound according to claim 11 or a pharmaceutically acceptable salt, or N-oxide thereof, wherein $R^9$ is —H or $C_1$-$C_6$ alkyl;

$R^{11}$ is selected from the group consisting of —(CH$_2$)$_2$—C(=O)—CH(R$^{13}$)—R$^{14}$, —(CH$_2$)$_2$—C(=O)—(CH$_2$)$_{1-3}$CH(R$^{13}$)—R$^{14}$ and —(CH$_2$)$_2$—C(=O)—CH(R$^{13}$)—NH—C(O)—R$^{14}$;

$R^{13}$ is selected from the group consisting of —H, —NH$_2$ and $C_1$-$C_6$ alkyl;

$R^{14}$ is selected from the group consisting of $C_1$-$C_6$ alkyl, —$C_0$-$C_6$ alkyl-C(O)—OR$^9$ and —CH(R$^{15}$)—N(H)—R$^{21}$;

$R^{15}$ is selected from the group consisting of —H, $C_1$-$C_6$ alkyl, and —$C_1$-$C_6$ alkyl-C(O)—OR$^9$; or $R^{15}$ together with the carbon atom to which it is attached and the nitrogen atom adjacent to the carbon atom form a cycloheteroalkyl group optionally substituted with —OH; and $R^{21}$ is selected from the group consisting of —H and —C(O)—O—R$^9$.

17. The compound according to claim 16, wherein $R^{11}$ is —(CH$_2$)$_2$—C(=O)—CH(R$^{13}$)—R$^{14}$.

18. The compound according to claim 17, wherein $R^{13}$ is —H or —NH$_2$ and $R^{14}$ is —NH$_2$, $C_1$-$C_3$ alkyl or —$C_1$-$C_5$ alkyl-C(O)—OH.

19. The compound according to claim 18, wherein $R^{14}$ is isopropyl or isobutyl or —(CH$_2$)—C(O)—OH.

20. The compound according to claim 11 or a pharmaceutically acceptable salt, or N-oxide thereof, wherein $R^{11}$ is selected from the group consisting of:

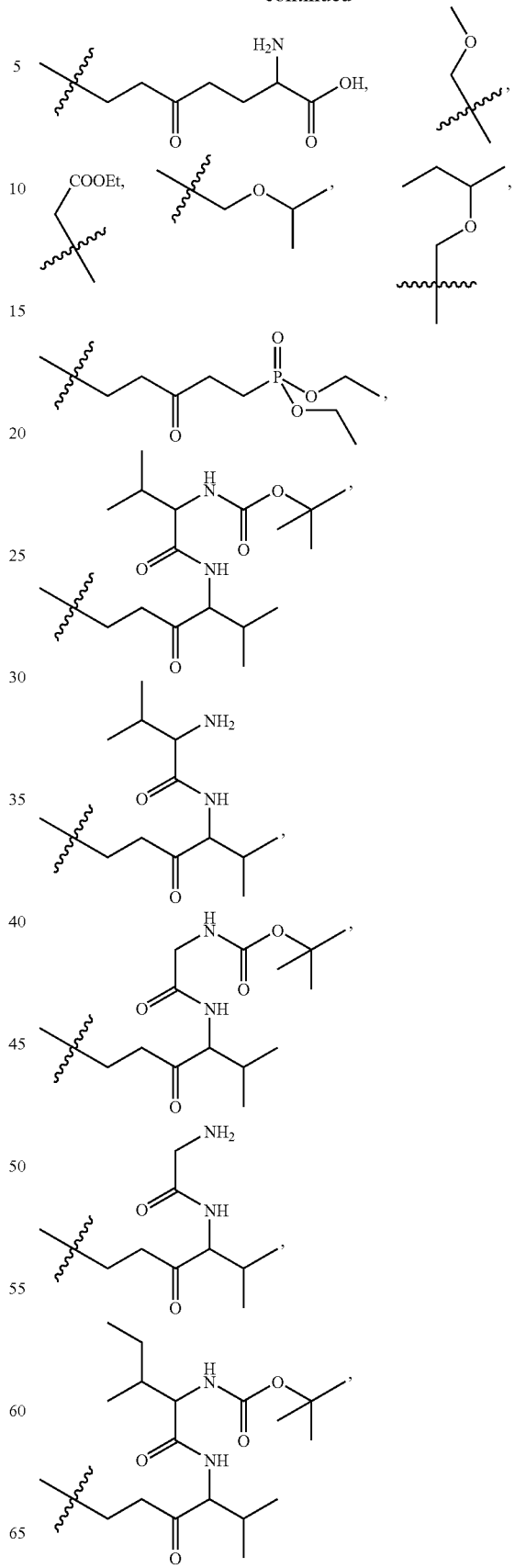

-continued
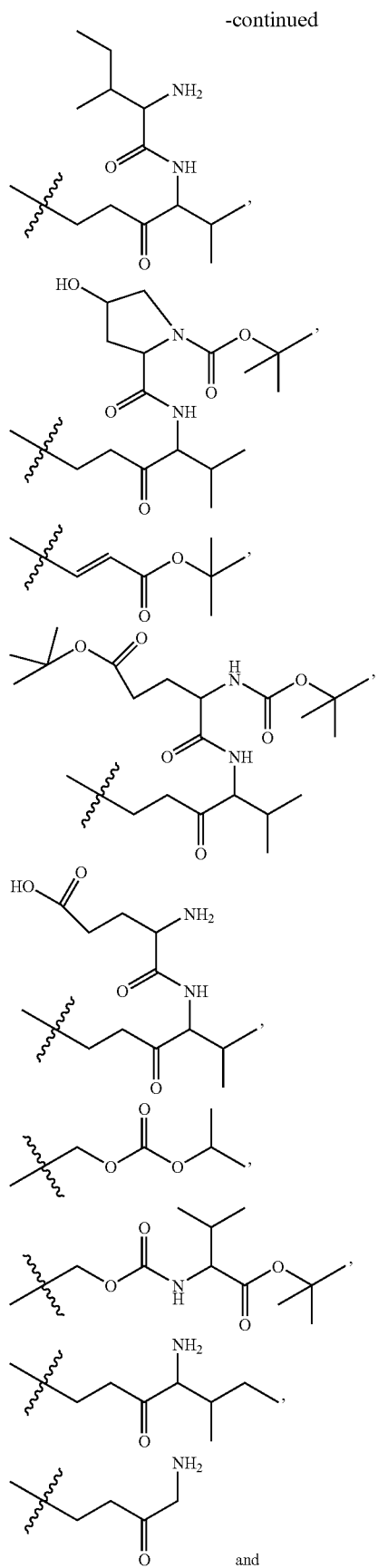
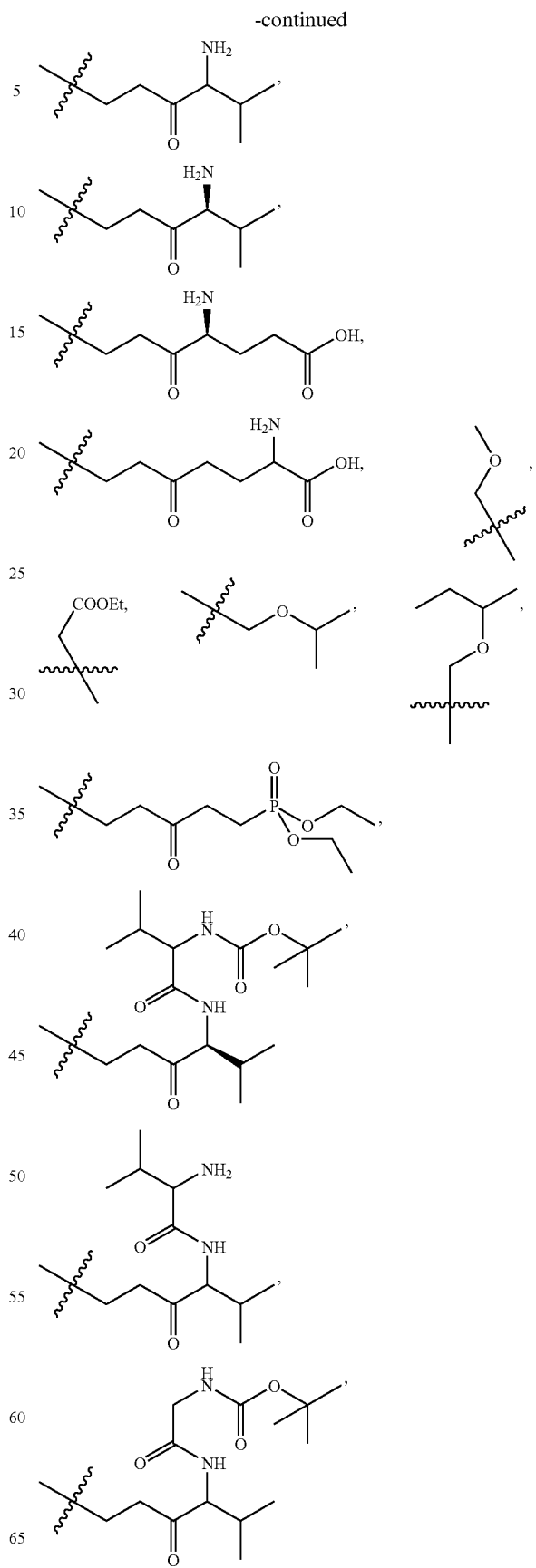

-continued
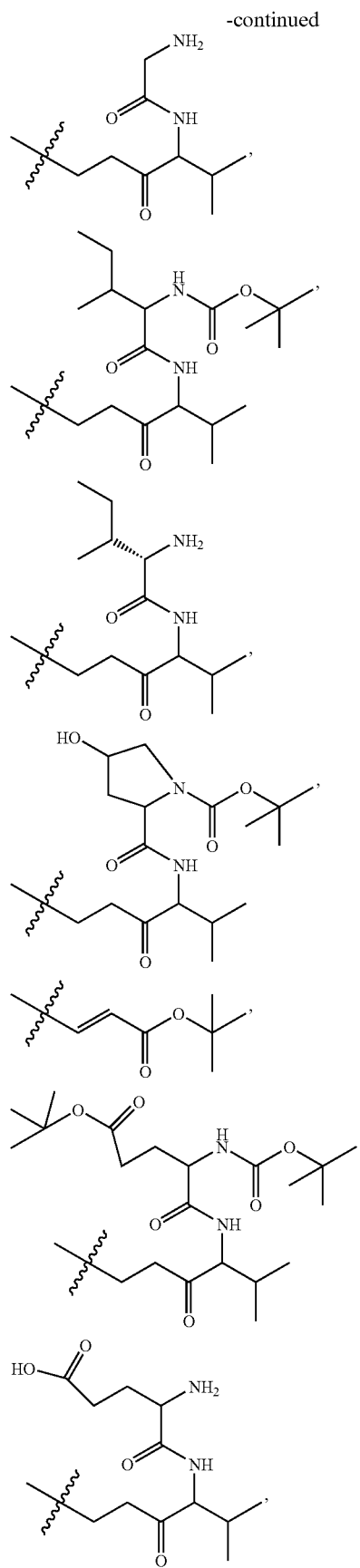
-continued
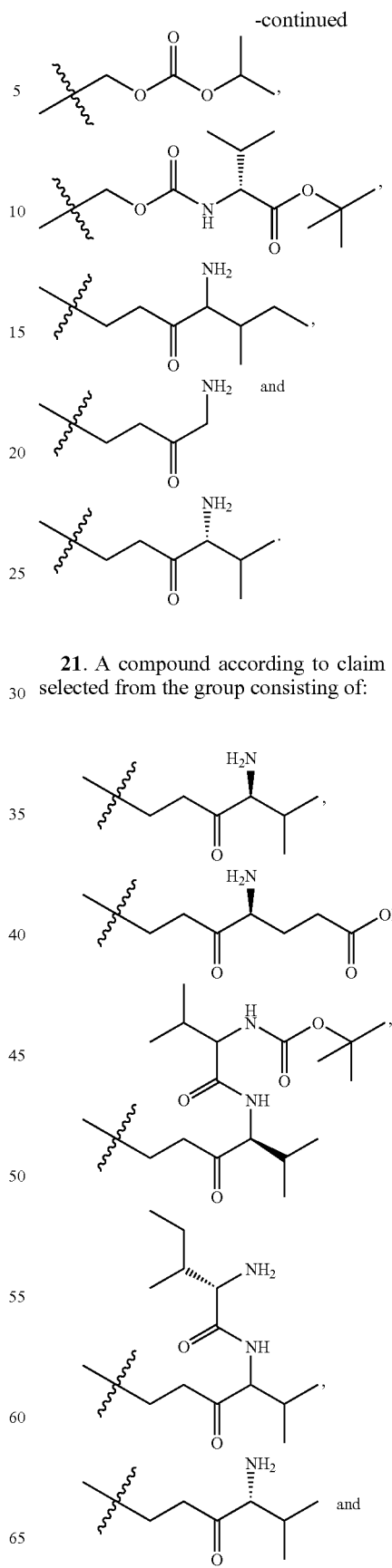
21. A compound according to claim 11, wherein $R^{11}$ is selected from the group consisting of:

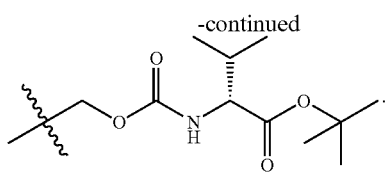
22. The compound according to claim 1, wherein when administered to a cell comprising a hepatitis C virion, the compound inhibits HCV replication and/or proliferation and has an $IC_{50}$ of 10 μM or less, as measured in an in vitro assay.
23. The compound according to claim 1 that is selected from the group consisting of:
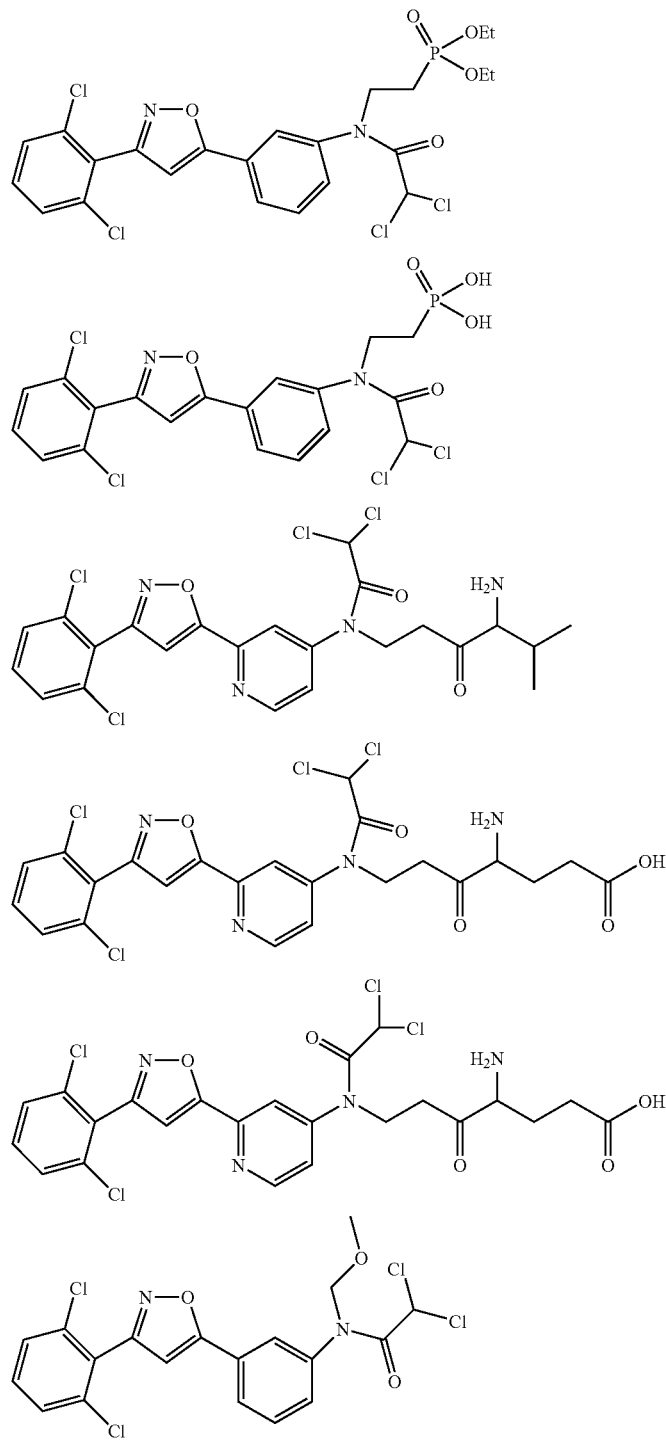

-continued
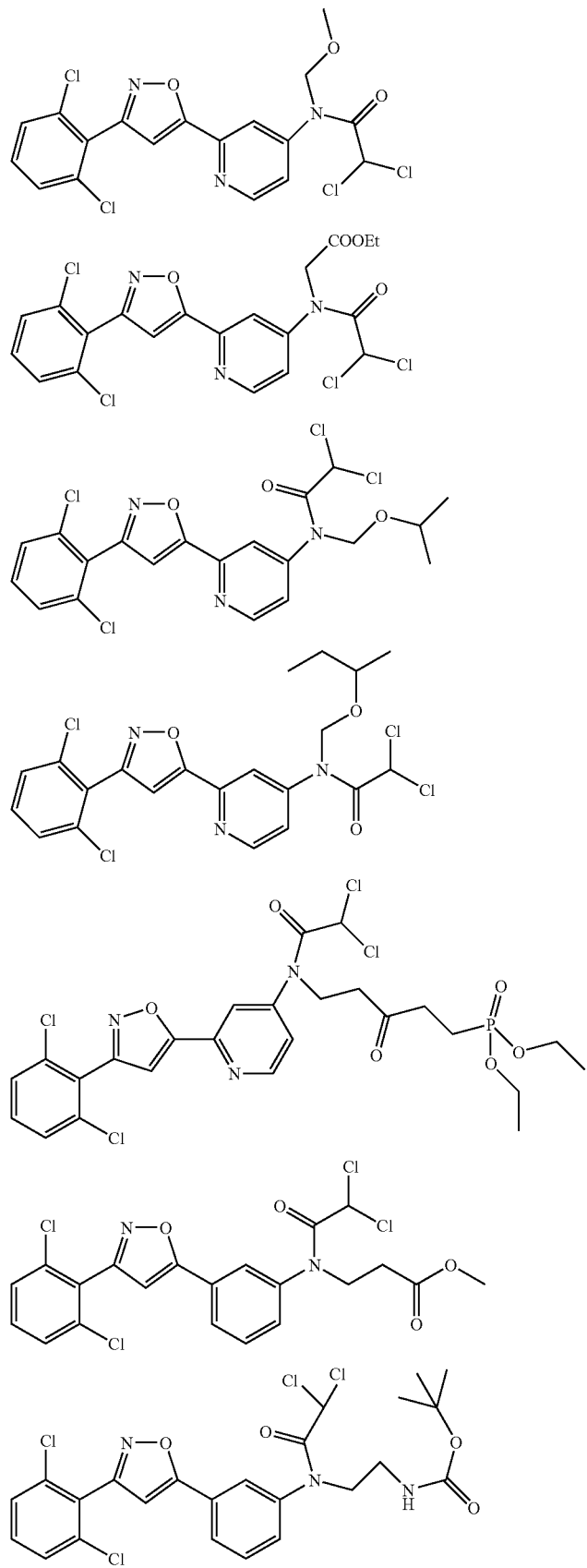

-continued
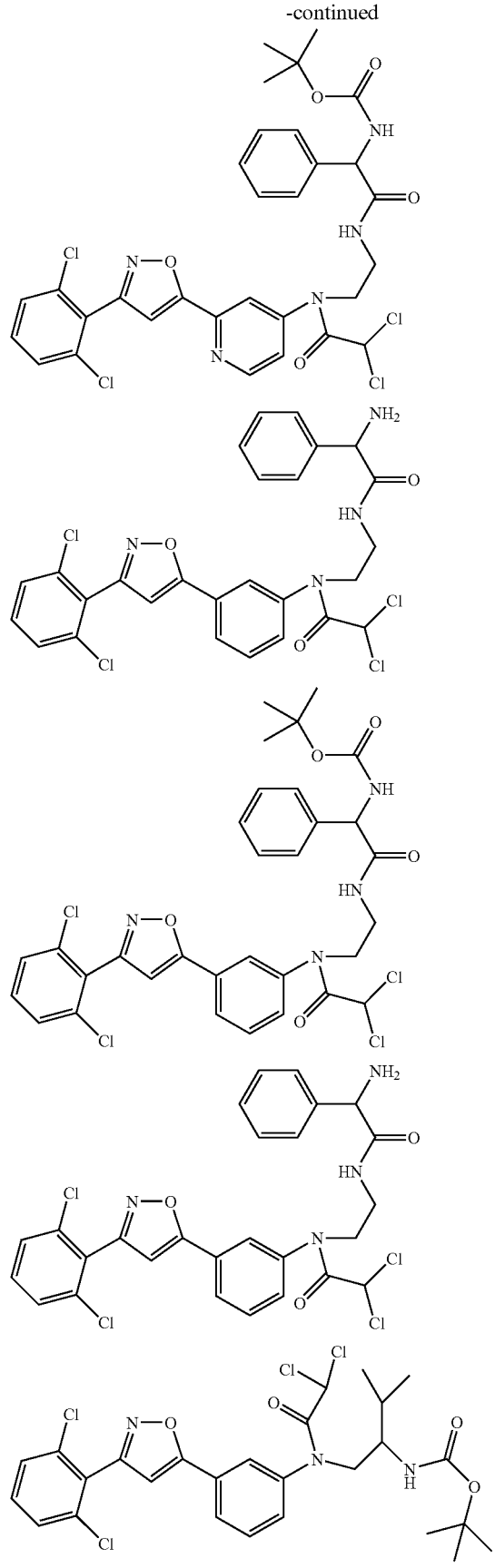

-continued
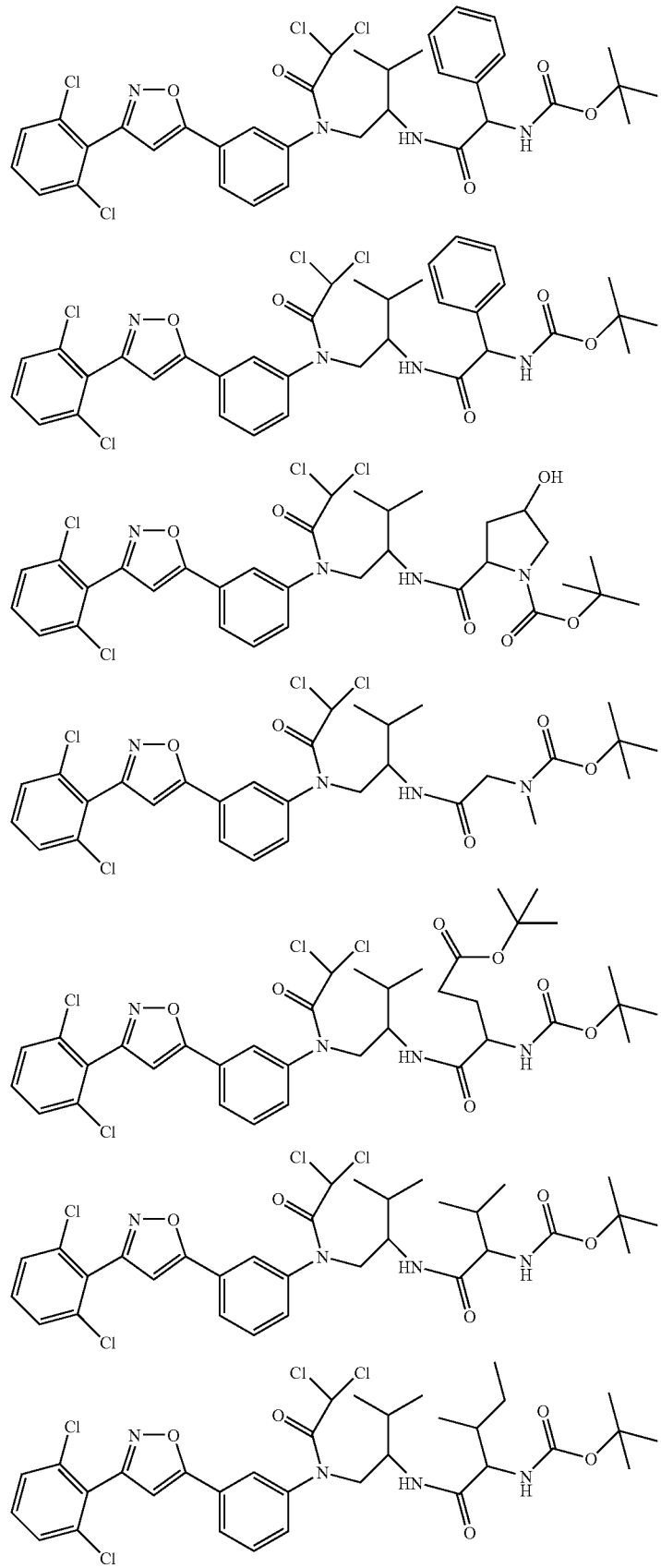

-continued
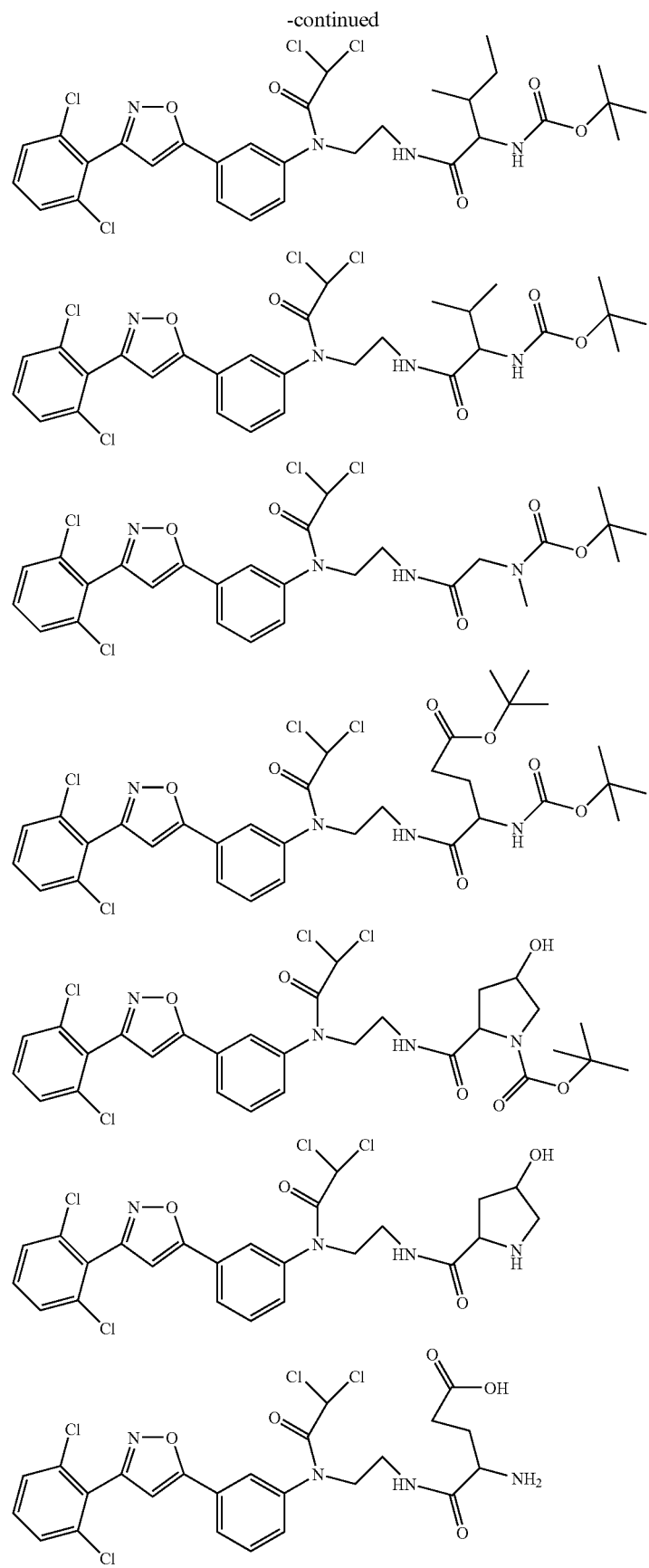

-continued
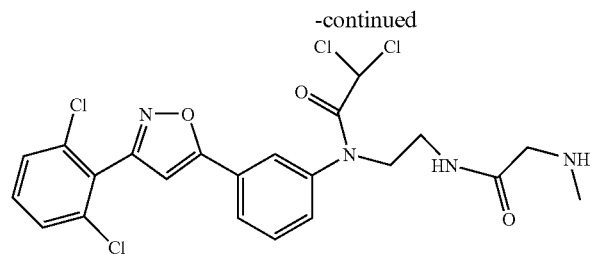
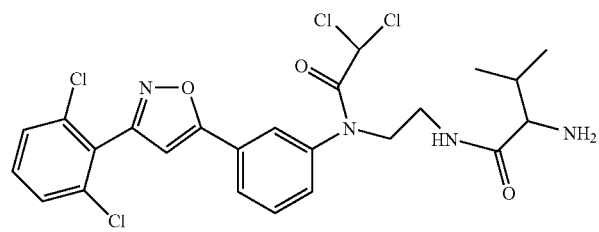
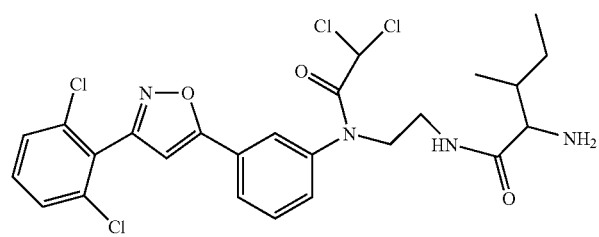
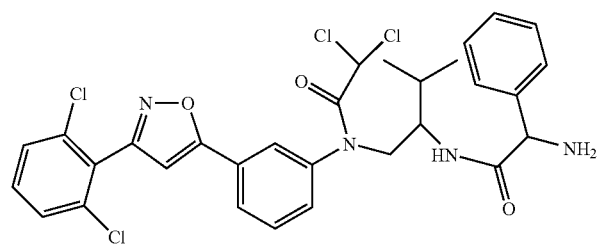
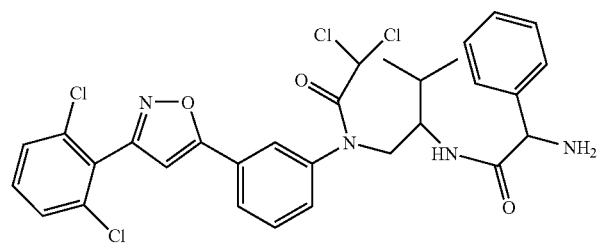
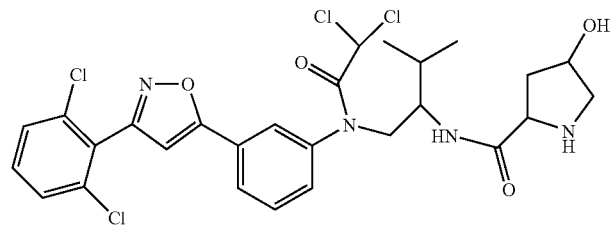
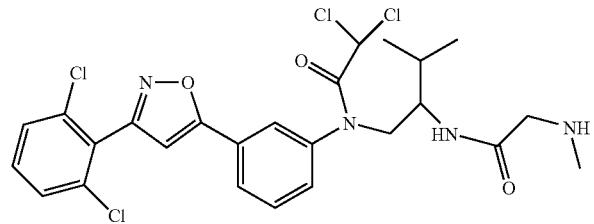

-continued
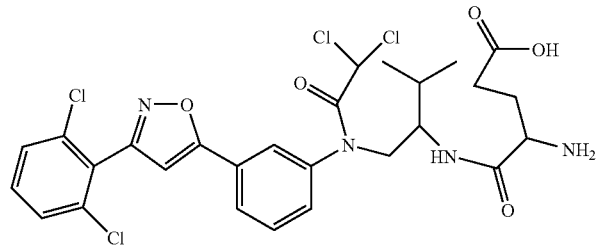
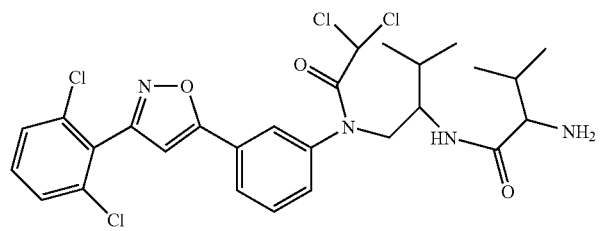
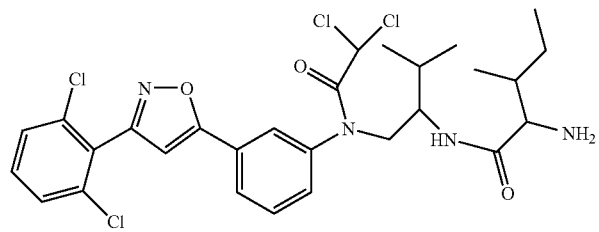
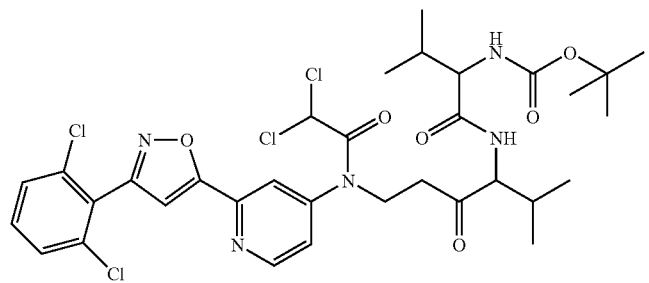
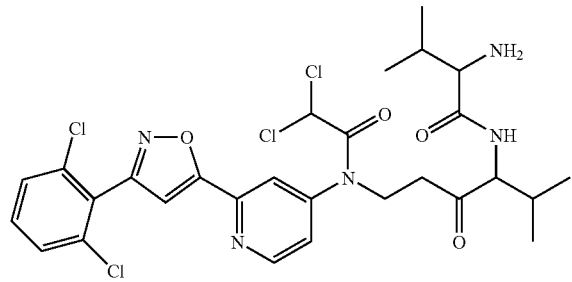
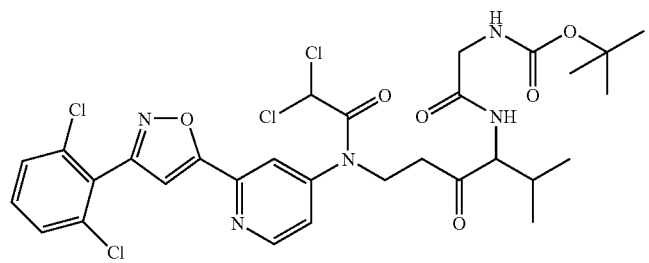

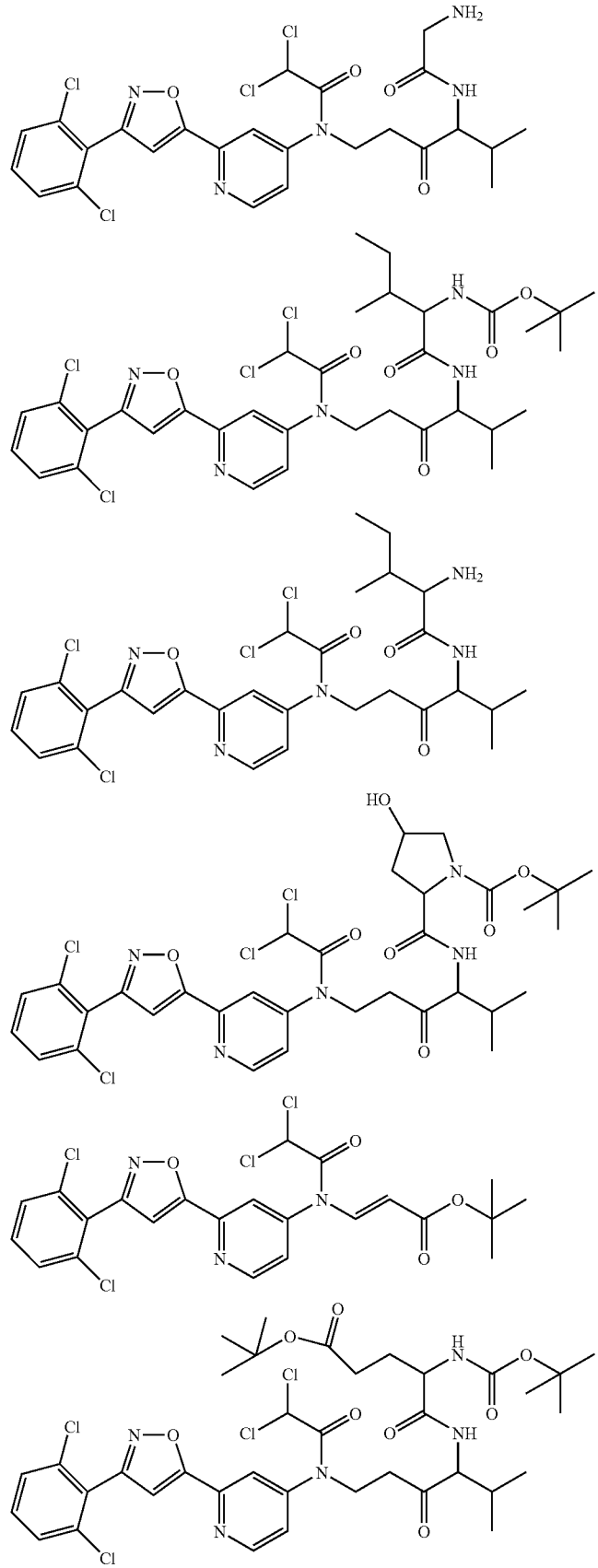

-continued
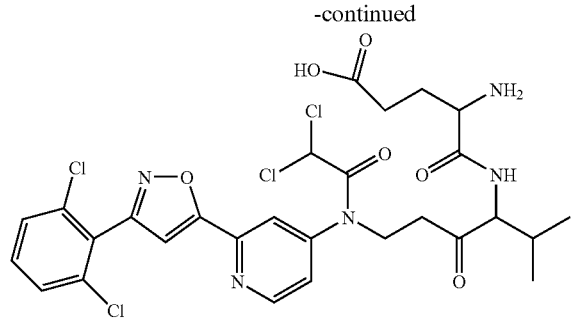
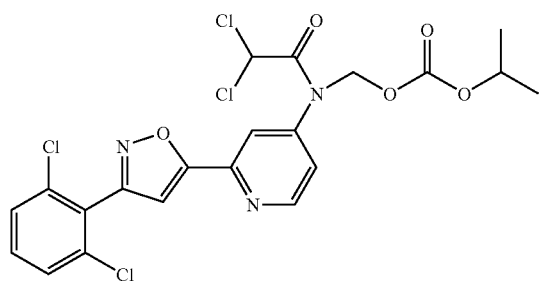
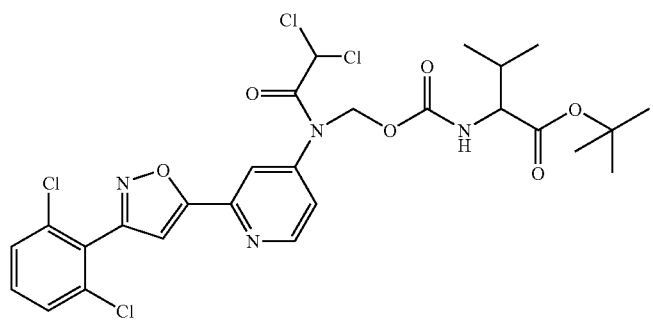
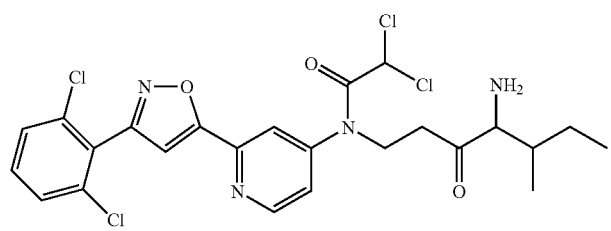
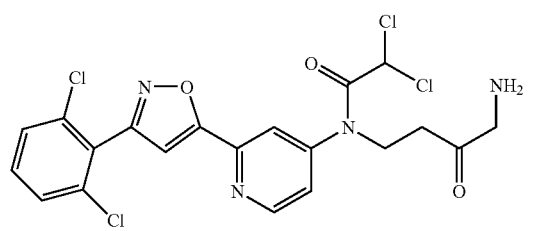
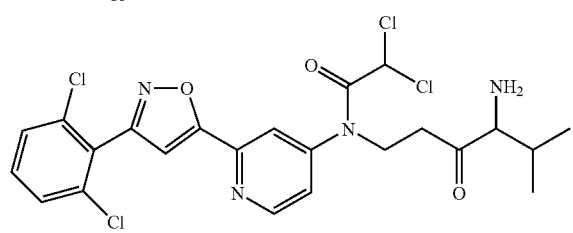

-continued
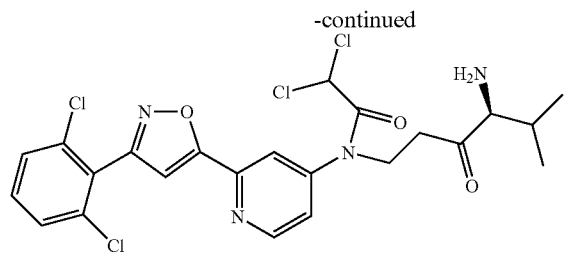
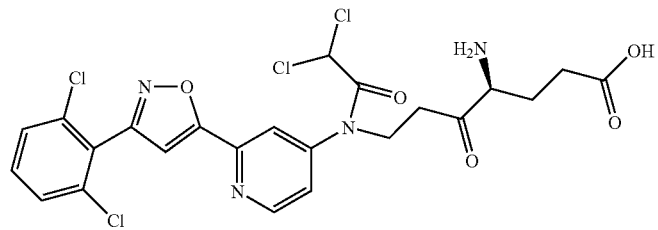
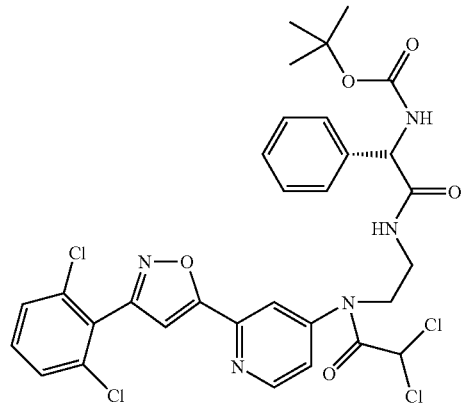
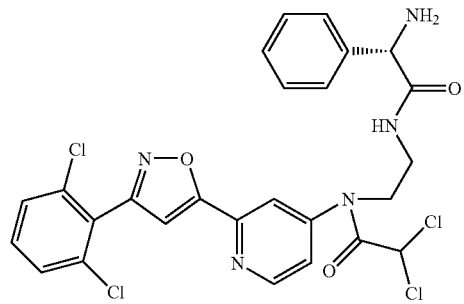
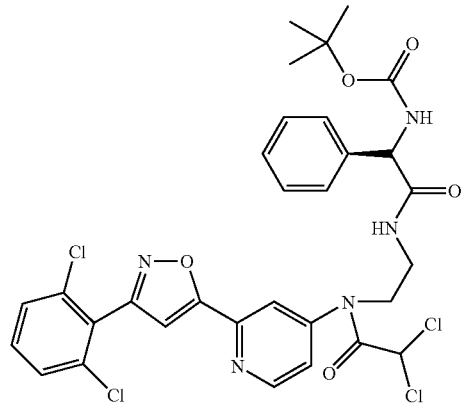

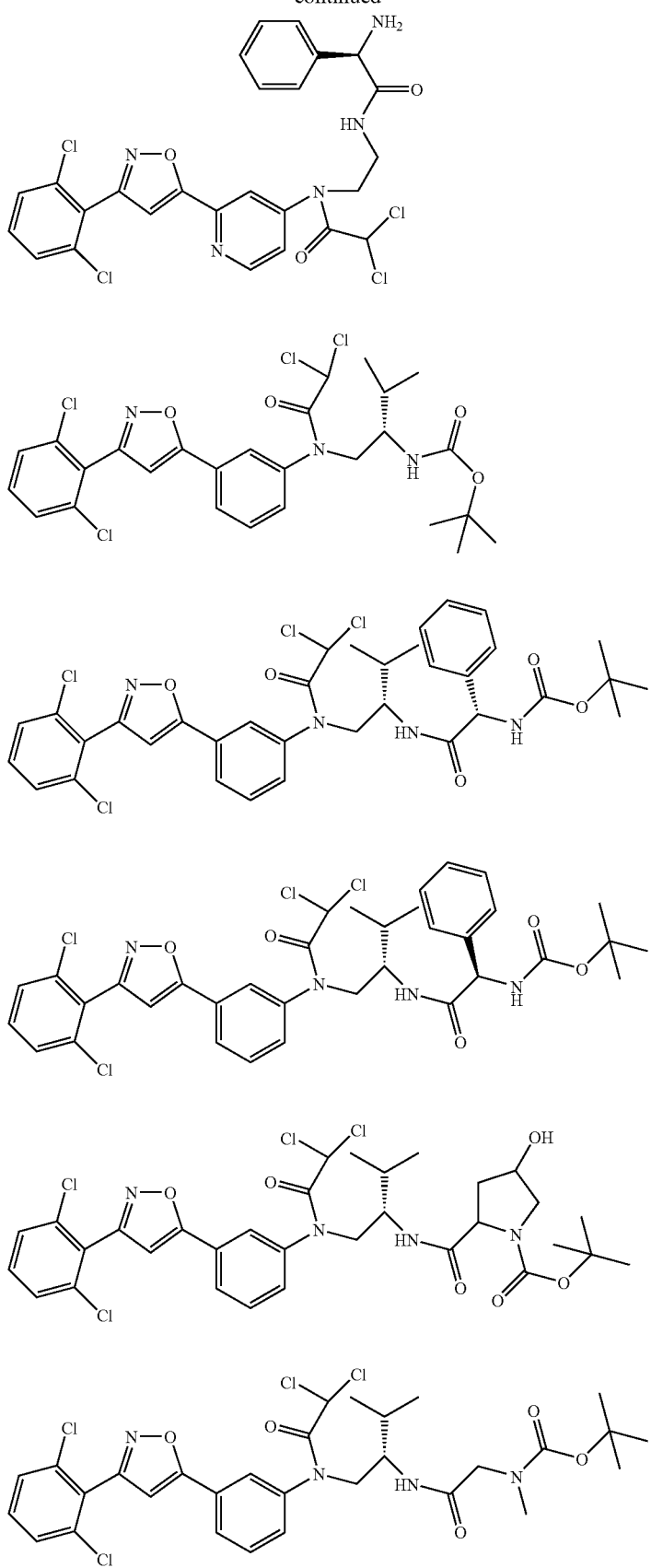

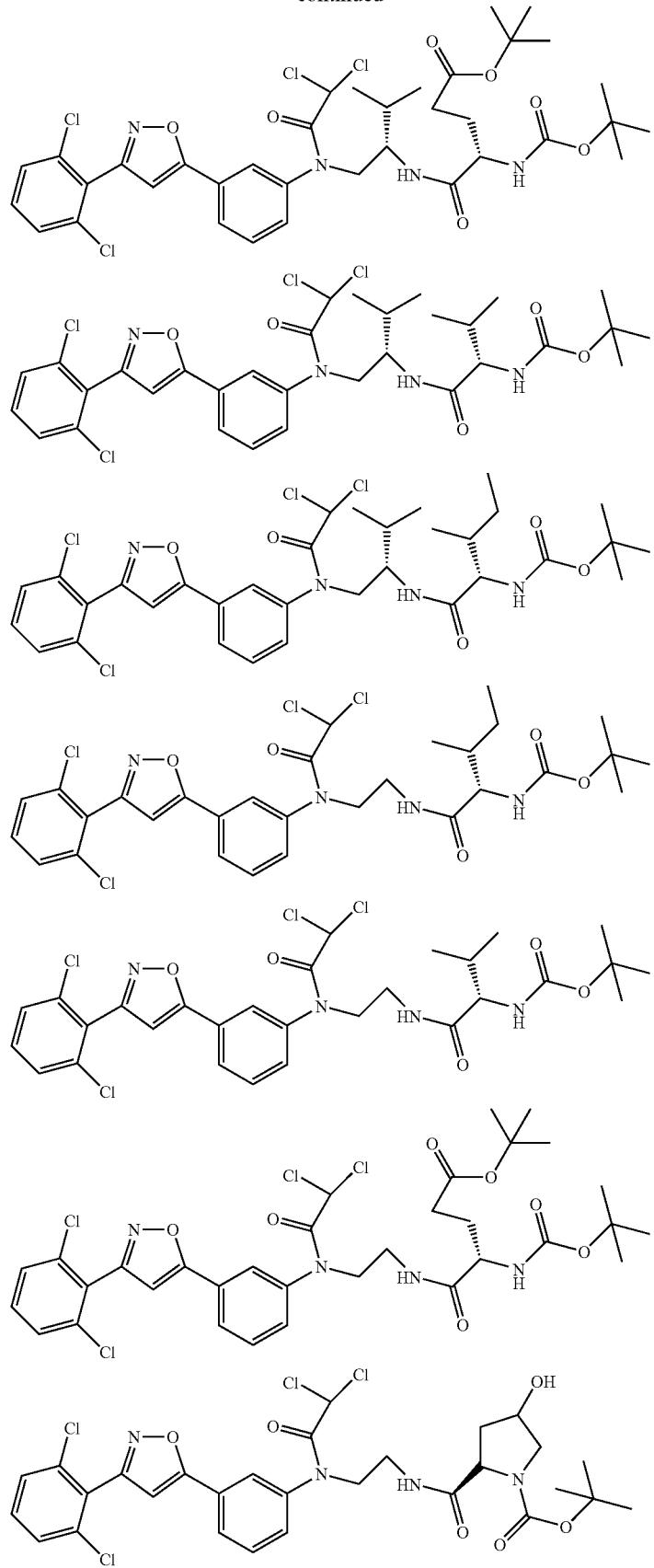

-continued
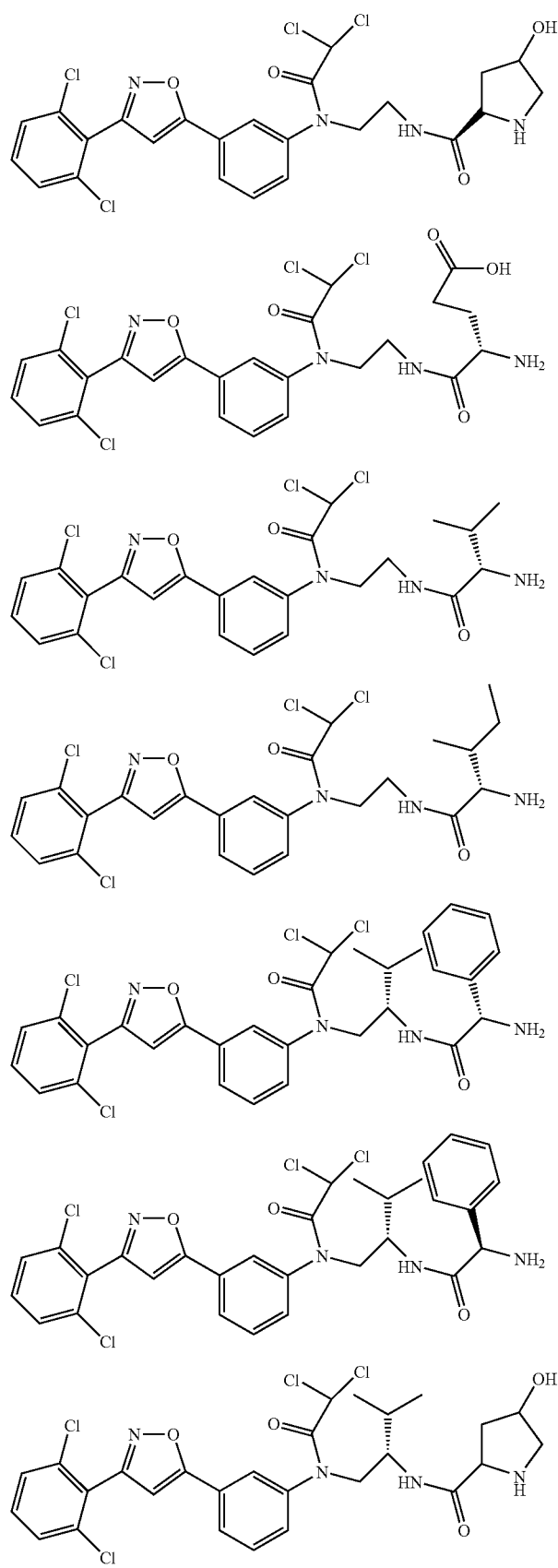

-continued
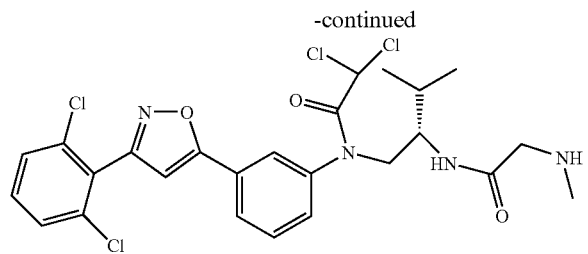
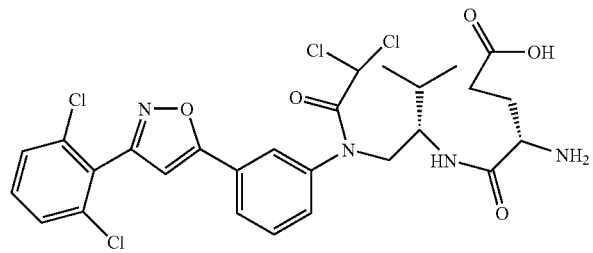
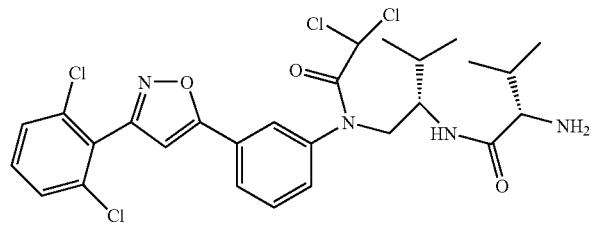
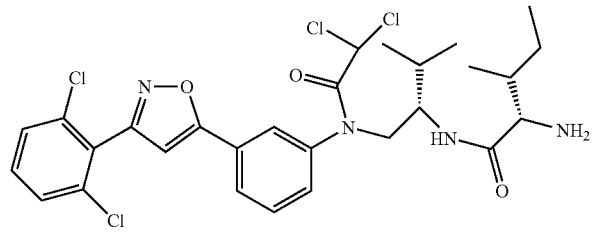
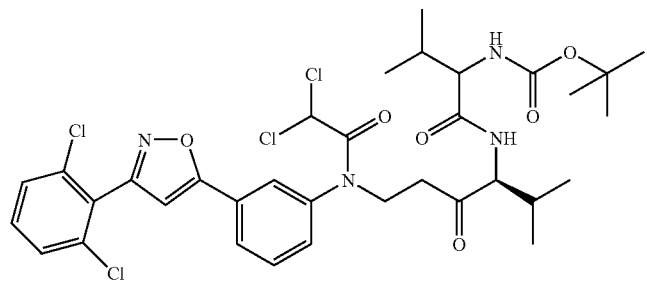
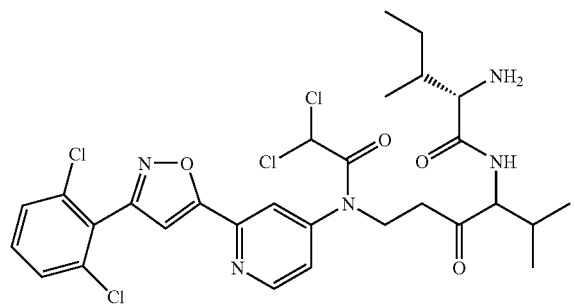

-continued
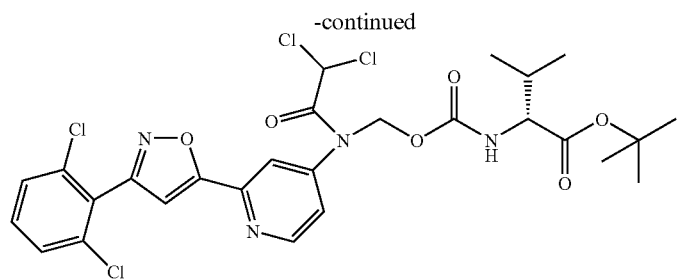
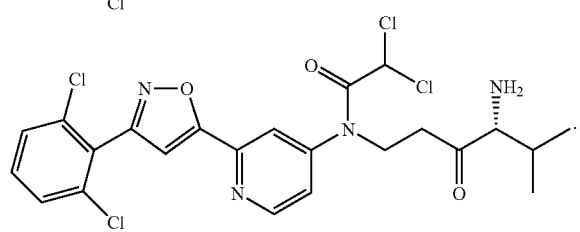
24. A composition comprising a pharmaceutically acceptable vehicle and a compound according to claim 1.
* * * * *